US007375220B2

(12) United States Patent
Bornemann et al.

(10) Patent No.: US 7,375,220 B2
(45) Date of Patent: May 20, 2008

(54) METHOD OF TREATING DISEASES AND CONDITIONS ASSOCIATED WITH AN ALTERED LEVEL OF AMYLOID β PEPTIDES AND NEW ENOLCARBOXAMIDE COMPOUNDS

(75) Inventors: Klaus Bornemann, Setzingen (DE); Guenter Trummlitz, Warthausen (DE); Edward S. Lazer, Trumbull, CT (US); Clara K. Miao, Easton, CT (US); Bernd Beck, Biberach an der Riss (DE); Frank Sams-Dodd, Biberach (DE); Dagmar Kugler, Schemmerhofen (DE); Klaus Klinder, Oggelshausen (DE); Cornelia Dorner-Ciossek, Ravensburg (DE); Marcus Kostka, Biberach (DE)

(73) Assignees: Boehringer Ingelheim Vetmedica GmbH, Ingelheim (DE); Boehringer Ingelheim Pharmaceuticals, Inc., Ridgefield, CT (US)

( * ) Notice: Subject to any disclaimer, the term of this patent is extended or adjusted under 35 U.S.C. 154(b) by 110 days.

(21) Appl. No.: 11/132,815

(22) Filed: May 19, 2005

(65) Prior Publication Data
US 2006/0040928 A1    Feb. 23, 2006

(30) Foreign Application Priority Data
May 19, 2004 (EP) .................................. 04011894

(51) Int. Cl.
*C07D 279/16* (2006.01)
*A61K 31/5415* (2006.01)
(52) U.S. Cl. ..................... 544/49; 514/226.5
(58) Field of Classification Search .................. 544/49; 514/226.5
See application file for complete search history.

(56) References Cited

U.S. PATENT DOCUMENTS

| 3,891,637 A | 6/1975 | Lombardino |
| 4,090,020 A | 5/1978 | Binder et al. |
| 4,175,085 A | 11/1979 | Binder et al. |
| 4,187,303 A | 2/1980 | Hromatka et al. |
| 4,683,306 A | 7/1987 | Suh et al. |
| 5,387,742 A | 2/1995 | Cordell |
| 5,612,486 A | 3/1997 | McConlogue et al. |
| 5,720,936 A | 2/1998 | Wadsworth et al. |
| 5,811,633 A | 9/1998 | Wadsworth et al. |
| 5,850,003 A | 12/1998 | McLonlogue et al. |
| 5,877,015 A | 3/1999 | Hardy et al. |
| 5,877,399 A | 3/1999 | Hsiao et al. |

FOREIGN PATENT DOCUMENTS

| JP | 05286941 | 2/1993 |
| WO | 9843630 A1 | 10/1998 |
| WO | 0115744 A1 | 3/2001 |
| WO | 0178721 A1 | 10/2001 |
| WO | 03040691 A2 | 5/2003 |
| WO | 03088811 A2 | 10/2003 |

OTHER PUBLICATIONS

M. Pfeifer, et al., "Cerebral Hemorrhage After Passive Anti-AB Immunotherapy", downloaded from www.sciencemag.org on Jul. 16, 2007.
Liana G. Apostolova, MD, et al., Conversion of Mild Cognitive Impairment to Alzheimer Disease Predicted by Hippocampal Atrophy Maps, downloaded from www.archneurol.com on Jul. 16, 2007.
Wiseman, Edward H., et al., Dioxoisoquinoline-4-Carboxanilides, Novel Non-Steroidal Anti-Inflammatory Agents with a species-specific effect on Basal Metabolism, Journal of Pharmacology and Experimental Therapeutics, vol. 172, No. 1, 1970, pp. 138-153.
Kadin, Saul B., et al., Dioxoisoquinoline-4-carboxanilides—a new class of nonsteroidal antiinflammatory agents, Nature, vol. 222, (Apr. 19, 1969) pp. 275-276.
Tanaka, Akira, et al., "Preparation of pyridine-2, 6-dione derivatives as allergy inhibitors", XP002367471, retrieved from STN Database accession No. 1994:217300 abstract.
International Search Report and Written Opinion of International Application No. PCT/EP2005/005229, filed May 13, 2005.

*Primary Examiner*—Kahsay T Habte
(74) *Attorney, Agent, or Firm*—Michael P. Morris; Mary-Ellen M. Devlin

(57) ABSTRACT

A method of treating or preventing of a disease or condition associated with an increased level of isoforms of amyloid β peptides (Aβ) and/or with a changed ratio of levels of Aβ isoforms and/or with the formation of plaques containing amyloid β peptide (Aβ) isoforms in a mammal comprising administering to said mammal an therapeutically effective amount of a compound selected from the formulas Ia, Ib

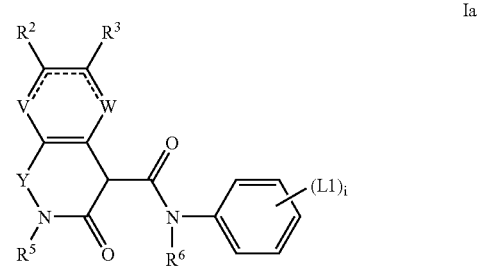

Ia

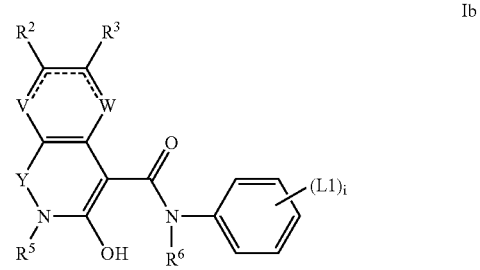

Ib wherein V, W, Y, $R^2$, $R^3$, $R^5$, $R^6$, L1 and i are defined as in claim 1.

4 Claims, No Drawings

METHOD OF TREATING DISEASES AND CONDITIONS ASSOCIATED WITH AN ALTERED LEVEL OF AMYLOID β PEPTIDES AND NEW ENOLCARBOXAMIDE COMPOUNDS

The invention relates to a method of treating or preventing of a disease or condition associated with an increased level of one or more isoforms of amyloid β peptides (Aβ) and/or with a changed ratio of levels of Aβ isoforms and/or with the formation of plaques containing one or more amyloid β peptide (Aβ) isoforms in a mammal. Furthermore this invention relates to the use of at least one compound selected from the formula Ia and Ib as defined herein for the manufacture of a medicament for preventing or treating of a disease or condition associated with an increased level of one or more isoforms of amyloid β peptides (Aβ) and/or with a changed ratio of levels of Aβ isoforms and/or with the formation of plaques containing one or more amyloid β peptide (Aβ) isoforms in a mammal. In addition, this invention is related to a pharmaceutical composition comprising at least one compound selected from the formula Ia and Ib as defined herein and at least one pharmaceutically acceptable carrier or diluent. Furthermore the present invention is related to the use of said compounds for modulating the activity of γ-secretase. In addition the present invention is related to the use of said compounds for the manufacture of a medicament for modulating the activity of γ-secretase. The present invention is also related to the new compounds selected from the group of formulas I.3a, I.3b, I.4a, I.4b, IIa, IIb, I.2.2a, I.2.2b, I.5.1a, I.5.1b, I.6.1a, and I.6.1b, which are active in lowering levels of amyloid β peptides.

Alzheimer's disease (AD) is a progressive degenerative disease of the brain primarily associated with aging. There also exists a hereditary form called familial Alzheimer's disease (FAD). The non-hereditary form of Alzheimer which is associated with aging is also called sporadic Alzheimer. In the following the term Alzheimers's disease or AD also encompasses said hereditary form. Clinical presentation of AD is characterized by loss of memory, cognition, reasoning, judgement, and orientation. As the disease progresses, motor, sensory, and linguistic abilities are also affected until there is global impairment of multiple cognitive functions. These cognitive losses occur gradually, but typically lead to severe impairment and death in the range of four to twelve years.

Alzheimer's disease is characterized by two major pathologic observations in the brain: neurofibrillary tangles (NFT) and beta amyloid (or neuritic) plaques, comprised predominantly of an aggregate of a peptide fragment known as amyloid β, A beta or Aβ. Individuals with AD exhibit characteristic beta-amyloid deposits in the brain (beta amyloid plaques) and in cerebral blood vessels (beta amyloid angiopathy) as well as neurofibrillary tangles. Neurofibrillary tangles occur not only in Alzheimer's disease but also in other dementia-inducing disorders. On autopsy, large numbers of these lesions are generally found in areas of the human brain important for memory and cognition.

Smaller numbers of these lesions in a more restricted anatomical distribution are found in the brains of most aged humans who do not have clinical AD.

Amyloidogenic plaques and vascular amyloid angiopathy also characterize the brains of individuals with Trisomy 21 (Down's Syndrome), Hereditary Cerebral Hemorrhage with Amyloidosis of the Dutch-Type (HCHWA-D), and other neurodegenerative disorders. Beta-amyloid is a neurotoxic peptide that exists in several isoforms, now believed to be a causative precursor or factor in the development of disease. Deposition of A beta in areas of the brain responsible for cognitive activities is a major factor in the development of AD. Beta-amyloid plaques are predominantly composed of amyloid beta peptide (A beta, also sometimes designated betaA4). A beta peptide is derived by sequential proteolysis of the amyloid precursor protein (APP) and is comprised of about 34 to 42 amino acids. Several proteases called secretases are involved in the processing of APP. Aβ consists predominantly of two forms, $A\beta_{40}$ and $A\beta_{42}$. Although $A\beta_{40}$ is the predominant form, evidence suggests that $A\beta_{42}$ is the pathogenic form. In addition to $A\beta_{40}$, and $A\beta_{42}$, the processing of APP generates other Aβ forms such as $A\beta_{39}$, $A\beta_{38}$, $A\beta_{37}$, and $A\beta_{34}$.

Cleavage of APP at the N-terminus of the A beta peptide by beta-secretase (BACE) and at the C-terminus by one or more gamma-secretases constitutes the beta-amyloidogenic pathway, i.e., the pathway by which A beta is formed. Cleavage of APP by alpha-secretase produces alpha-sAPP, a secreted form of APP that does not result in beta-amyloid plaque formation. This alternate pathway precludes the formation of A beta peptide.

An aspartyl protease has been identified as the enzyme responsible for processing of APP at the beta-secretase cleavage site. The beta-secretase enzyme has been disclosed using varied nomenclature, including BACE, Asp2, and Memapsin2.

Gamma-secretase is a multiprotein complex that consists of at least four membrane-bound proteins: presenilin (PS), nicastrin, APH-1, and PEN-2. All of these components are required for proper maturation and activity of the complex while the enzymatic core of this activity may reside within presenilin itself. The gamma-secretase activity displays a flexibel sequence specificity. Therefore, A beta peptides of varying lengths, such as $A\beta_{38}$, $A\beta_{40}$, $A\beta_{42}$ are generated.

It has been found that mutations in PS1 and PS2 which cause familial Alzheimer's disease (FAD) also alter APP processing and cause overproduction of $A\beta_{42}$ peptides such that the ratio of levels of $A\beta_{40}$ to $A\beta_{42}$ is changed (See also literature cited by Sisodia S S and George-Hyslop P H, 2002. γ Secretase, notch, Aβ and Alzheimer's Disease: where do the presenilins fit in? Nature Reviews Neuroscience, 3, 281-290).

Several lines of evidence indicate that progressive cerebral deposition of beta-amyloid peptide (A beta) plays a seminal role in the pathogenesis of AD and can precede cognitive symptoms by years or decades. See, for example, Selkoe, 1991, Neuron 6: 487-498. Release of A beta from neuronal cells grown in culture and the presence of A beta in cerebrospinal fluid (CSF) of both normal individuals and AD patients has been demonstrated. See, for example, Seubert et al., 1992, Nature 359: 325-327.

Various pharmaceutical agents have been proposed for the treatment of Alzheimer's disease but without any real success.

In the WO 98/20864, the use of non-steroidal antiinflammatory compounds for the prevention and the treatment of glutamate receptor-mediated neuronal damages is described. Among many other compounds piroxicam, tenoxicam and meloxicam are mentioned as NSAIDs. The disease Alzheimer is listed as belonging to the group of glutamate receptor-mediated neuronal damages.

In the EP 0 642 336 A, the use of non-steroidal antiinflammatory substances which have the ability to inhibit prostaglandin synthesis in the human being is described for the treament of dementia.

In the WO 01/78721, a method of preventing, delaying or reversing the progression of Alzheimer's disease by the administration of Aβ42 lowering agents is described. Suitable Aβ42 lowering agents are meclofenamic acid, flufenamic acid, fenoprofen, flurbiprofen, carprofen, indomethacin, sulindac sulfide, ibuprofen, ketoprofen, etc. which belong to the group of nonsteroidal antiinflammatory drugs (NSAIDs). On the other hand not all NSAIDs show a Aβ42 lowering activity. According to the table 3 as depicted in the WO 01/78721 meloxicam, piroxicam and isoxicam, which all belong to the class of the enol carboxamides, do not lower or even increase the Aβ42 level.

Evidence has been provided that specific compounds which belong to the class of NSAIDs may interact with gamma-secretase, either directly or indirectly:

Eriksen J L et al., 2003. NSAIDs and enantiomers of flurbiprofen target γ-secretase and lower Aβ42 in vivo., J. Clin. Invest. 112, 3, 440-449;

Weggen S et al., 2003. Evidence that nonsteroidal anti-inflammatory drugs decrease amyloid β42 production by direct modulation of γ-secretase activity. J. Biol. Chem. 278 (34), 31831-31837;

Takahashi Y et al., 2003. Sulindac Sulfide is a noncompetitive γ-secretase inhibitor that preferentially reduces Aβ42 generation, J. Biol. Chem. 278 (20), 18664-18670;

Weggen S et al., 2001. A subset of NSAIDs lower amyloidogenic Aβ42 independently of cyclooxygenase activity. Nature 414, 212-216;

Zhou Y et al., 2003. Nonsteroidal anti-inflammatory drugs can lower amyloidogenic Aβ42 by inhibiting Rho, Science, 302, 1215-1217.

At present there are no non symptomatic effective treatments for halting, preventing, or reversing the progression of Alzheimer's disease. Therefore, there is an urgent need for pharmaceutical agents with sufficient plasma and/or brain stability capable of slowing the progression of Alzheimer's disease and/or preventing it in the first place.

SUMMARY OF THE INVENTION

Surprisingly, it has been found that compounds selected from the formula Ia and Ib as defined in the following have an activity to reduce or inhibit the formation of isoforms of amyloid β peptides (Aβ), to change the ratio of levels of isoforms of Aβ and/or to modulate the activity of γ-secretase.

Therefore, the present invention relates to a method of treating or preventing of a disease or condition associated with an increased level of one or more isoforms of amyloid β peptides (Aβ) and/or with a changed ratio of levels of Aβ isoforms and/or with the formation of plaques containing one or more amyloid β peptide (Aβ) isoforms in a mammal comprising administering to said mammal a therapeutically effective amount of at least one compound selected from the formulas Ia, Ib

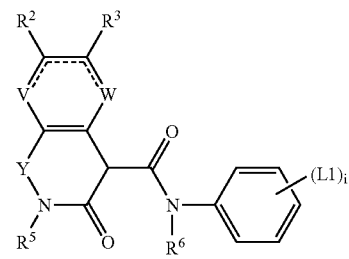

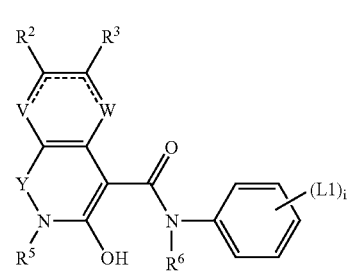

wherein

---- represents a single or a double bond, such that the ring containing the groups V and W is a phenyl, a furanyl or a thiophenyl ring;

V is defined as —CR$^1$= or Q, and
in case W is Q, then V is a single bond;

W is defined as =CR$^4$— or Q, and
in case V is Q, then W is a single bond;

Q is O or S;

Y is —(C=O)— or —(SO$_2$)—;

R$^1$, R$^4$ are each independently selected from the group consisting of H, F, Cl, Br, CN, CF$_3$, C$_{1-4}$-alkyl and C$_{1-4}$-alkoxy; and R$^2$, R$^3$ are each independently selected from the group consisting of H, F, Cl, Br, CN, CF$_3$, C$_{1-4}$-alkyl and C$_{1-4}$-alkoxy; or in case V is —CR$^1$= and W is =CR$^4$—, the substituents R$^2$ and R$^3$ may be linked together forming with the C-atoms to which they are attached to a C$_{5-7}$-cycloalkyl, C$_{5-7}$-cycloalkenyl or a phenyl group, wherein the cycloalkyl, cycloalkenyl or phenyl ring may be substituted with one or more substituents L2; or in case V is —CR$^1$= and W is =CR$^4$—, the substituents R$^1$ and R$^2$ may be linked together forming with the C-atoms to which they are attached to a C$_{5-7}$-cycloalkyl, C$_{5-7}$-cycloalkenyl or a phenyl group, wherein the cycloalkyl, cycloalkenyl or phenyl ring may be substituted with one or more substituents L2;

R$^5$ is selected from the group consisting of H, C$_{1-4}$-alkyl, C$_{3-6}$-cycloalkyl, C$_{3-6}$-cycloalkyl-C$_{1-3}$-alkyl, phenyl and phenyl-C$_{1-3}$-alkyl, wherein a cycloalkyl or phenyl ring may be substituted with one or more substituents independently selected from the group consisting of F, Cl, Br, CN, CF$_3$, C$_{1-4}$-alkyl, C$_{1-4}$-alkoxy, C$_{1-4}$-alkylcarbonyl;
R$^6$ is H or C$_{1-4}$-alkyl;
L1 is each independently selected from the group consisting of C$_{1-4}$-alkyl, C$_{1-3}$-alkoxy, F, Cl, Br, CN, NO$_2$ and CF$_3$;
L2 is each independently selected from the group consisting of C$_{1-4}$-alkyl, F, Cl, Br, CN and CF$_3$;
i is 0, 1, 2, 3, 4 or 5;

or a pharmaceutically acceptable salt thereof.

Compounds which can be described by a general formula Ia or Ib were tested in view of their COX-2/COX-1 selectivity in comparison with the nonsteroidal antiinflammatory drug meloxicam (E. S. Lazer et al., J. Med. Chem. 1997, 40, 980-989). Furthermore thienothiazine derivatives are described in the U.S. Pat. No. 4,175,085, U.S. Pat. No. 4,187,303 and U.S. Pat. No. 4,090,020 as being useful as anti-inflammatroy, analgesic and anti-rheumatic agents. In addition 3,4-dihydro-2H-1,2-benzothiazine 1,1-dioxide derivatives and their use as anti-inflammatory agents are described in the U.S. Pat. No. 3,591,584.

As the compounds according to this invention belong to the NSAID group of enol carboxamides and show a structural similarity with meloxicam, it is completely surprising that these compounds exhibit a lowering activity on Aβ isoforms and/or modulate the activity of γ-secretase. Analysing the results as disclosed in the WO 01/78721 with regard to enol carboxamides and especially with regard to meloxicam, the person skilled in the art would not have expected to identify other members of the group of the enol carboxamides as effective agents to lower the level of Aβ isoforms.

Therefore, the compounds, compositions, and methods of the present invention are effective to inhibit the production of amyloid β peptides (Aβ) and to treat or prevent human or veterinary diseases or conditions associated with a pathological form of amyloid β peptides (Aβ), in particular of Aβ$_{42}$.

The compounds, compositions, and methods of the invention are useful for treating humans who have Alzheimer's Disease (AD), for helping prevent or delay the onset of AD, for treating patients with mild cognitive impairment (MCI), and preventing or delaying the onset of AD in those patients who would otherwise be expected to progress from MCI to AD, for treating Down's syndrome, for treating Hereditary Cerebral Hemorrhage with Amyloidosis of the Dutch Type, for treating cerebral beta-amyloid angiopathy and preventing its potential consequences such as single and recurrent lobar hemorrhages, for treating other degenerative dementias, including dementias of mixed vascular and degenerative origin, for treating dementia associated with Parkinson's disease, dementia associated with progressive supranuclear palsy, dementia associated with cortical basal degeneration, and diffuse Lewy body type AD.

According to another embodiment those compounds and compositions used in a method according to this invention are preferred which exhibit a COX inhibiting activity, especially a COX-2 inhibiting activity, in particular those which inhibit COX-2 selectively. Such compounds and compositions are expected to be particularly useful for treating and/or preventing those inflammatory diseases or inflammatory conditions associated with an increased level of one or more isoforms of amyloid β peptides (Aβ) and/or with a changed ratio of levels of Aβ isoforms and/or with the formation of plaques containing one or more amyloid β peptide (Aβ) isoforms in a mammal. Furthermore such compounds and compositions are expected to be particularly useful for a combined treatment and/or prevention of an inflammatory disease or inflammatory condition and a disease or condition associated with an increased level of one or more isoforms of amyloid β peptides (Aβ) and/or with a changed ratio of levels of Aβ isoforms and/or with the formation of plaques containing one or more amyloid β peptide (Aβ) isoforms. For example, such compounds and compositions are expected to be useful for treating humans who are diagnosed to have for example both Alzheimer's disease (AD) and a disease associated with inflammatory conditions, in particular Parkinson's disease.

Therefore, in another aspect the present invention describes the use of at least one compound selected from the formula Ia and Ib as defined hereinbefore and hereinafter, or a pharmaceutically acceptable salt thereof, for the manufacture of a medicament for preventing or treating of one or more diseases or conditions associated with an increased level of one or more amyloid β peptides (Aβ) and/or with a changed ratio of levels of Aβ isoforms and/or with the formation of plaques containing one or more amyloid β peptides (Aβ) in a mammal.

In a further aspect the present invention relates to the use of at least one compound selected from the formulas Ia, Ib as defined hereinbefore and hereinafter, or a pharmaceutically acceptable salt thereof, for modulating the activity of γ-secretase.

Therefore the present invention also relates to the use of at least one compound selected from the formulas Ia, Ib as defined hereinbefore and hereinafter, or a pharmaceutically acceptable salt thereof, for the manufacture of a medicament for modulating the activity of γ-secretase.

In addition the present invention relates to a pharmaceutical composition comprising at least one compound selected from the formula Ia and Ib as defined hereinbefore and hereinafter, or a pharmaceutically acceptable salt thereof, and at least one pharmaceutically acceptable carrier or diluent.

The inhibitory activities of the compounds of the formula Ia and Ib of the present invention are readily demonstrated, for example, using one or more of the assays described herein or known in the art.

A further aspect of the present invention is related to new compounds selected from the group of formulas I.3a, I.3b, I.4a, I.4b

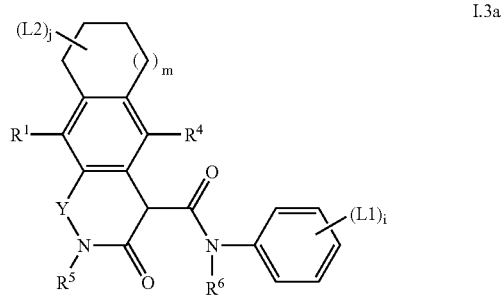

I.3a

-continued

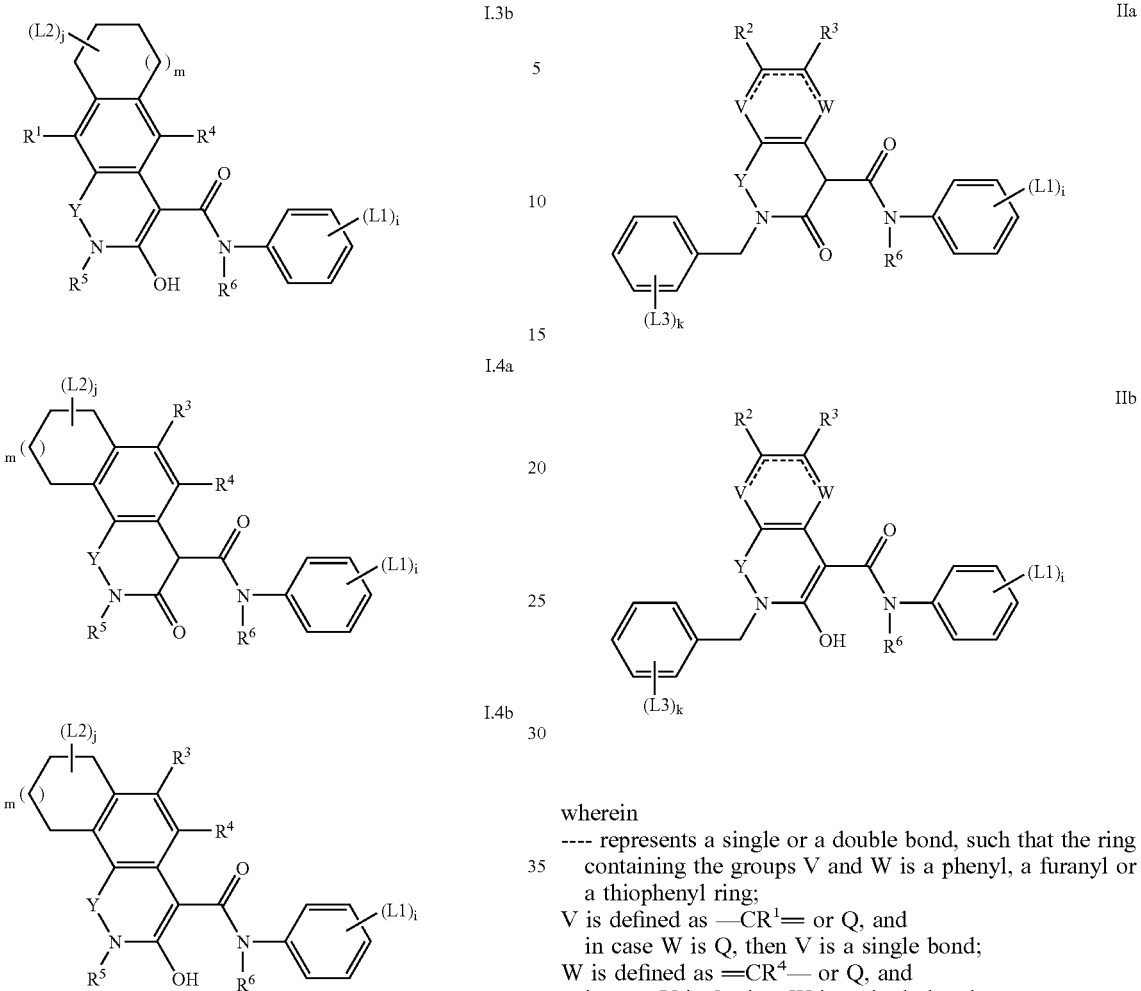

Y is —(C=O)— or —(SO$_2$)—;

R$^1$, R$^3$,

R$^4$ are each independently selected from the group consisting of H, F, Cl, Br, CN, CF$_3$, C$_{1-4}$-alkyl and C$_{1-4}$-alkoxy;

R$^5$ is selected from the group consisting of H, C$_{1-4}$-alkyl, C$_{3-6}$-cycloalkyl, C$_{3-6}$-cycloalkyl-C$_{1-3}$-alkyl, phenyl and phenyl-C$_{1-3}$-alkyl, wherein the phenyl ring of the phenyl or the phenyl-alkyl group may be substituted with one or more substituents independently selected from the group consisting of F, Cl, Br, CN, CF$_3$, C$_{1-4}$-alkyl, C$_{1-4}$-alkyl-carbonyl;

R$^6$ is H or C$_{1-4}$-alkyl;

L1 is each independently selected from the group consisting of C$_{1-4}$-alkyl, C$_{1-3}$-alkoxy, F, Cl, Br, CN, NO$_2$ and CF$_3$;

L2 is each independently selected from the group consisting of C$_{1-4}$-alkyl, F, Cl, Br, CN and CF$_3$;

i is 0, 1, 2, 3, 4 or 5;

j is 0, 1, 2 or 3;

m is 0, 1 or 2;

or a pharmaceutically acceptable salt thereof.

Another further aspect of the present invention is a compound selected from the formulas IIa, IIb wherein ---- represents a single or a double bond, such that the ring containing the groups V and W is a phenyl, a furanyl or a thiophenyl ring;

V is defined as —CR$^1$= or Q, and
  in case W is Q, then V is a single bond;

W is defined as =CR$^4$— or Q, and
  in case V is Q, then W is a single bond;

Q is O or S;

Y is —(C=O)— or —(SO$_2$)—;

R$^1$, R$^4$ are each independently selected from the group consisting of H, F, Cl, Br, CN, CF$_3$, C$_{1-4}$-alkyl and C$_{1-4}$-alkoxy; and R$^2$, R$^3$ are each independently selected from the group consisting of H, F, Cl, Br, CN, CF$_3$, C$_{1-4}$-alkyl and C$_{1-4}$-alkoxy; or in case V is —CR$^1$= and W is =CR$^4$—, the substituents R$^2$ and R$^3$ may be linked together forming with the C-atoms to which they are attached to a C$_{5-7}$-cycloalkyl, C$_{5-7}$-cycloalkenyl or a phenyl group, wherein a cycloalkyl, cycloalkenyl or phenyl ring may be substituted with one or more substituents L2; or in case V is —CR$^1$= and W is =CR$^4$—, the substituents R$^1$ and R$^2$ may be linked together forming with the C-atoms to which they are attached to a C$_{5-7}$-cycloalkyl, C$_{5-7}$-cycloalkenyl or a phenyl group, wherein a cycloalkyl, cycloalkenyl or phenyl ring may be substituted with one or more substituents L2;

R$^6$ is H or C$_{1-4}$-alkyl;

L1 is each independently selected from the group consisting of C$_{1-4}$-alkyl, C$_{1-3}$-alkoxy, F, Cl, Br, CN, NO$_2$ and CF$_3$;

L2, L3 is each independently selected from the group consisting of C$_{1-4}$-alkyl, F, Cl, Br, CN and CF$_3$;

i is 0, 1, 2, 3, 4 or 5;

k is 1, 2, 3, 4 or 5;

or a pharmaceutically acceptable salt thereof.

Another further aspect of the present invention is a compound selected from the formulas I.2.2a, I.2.2b

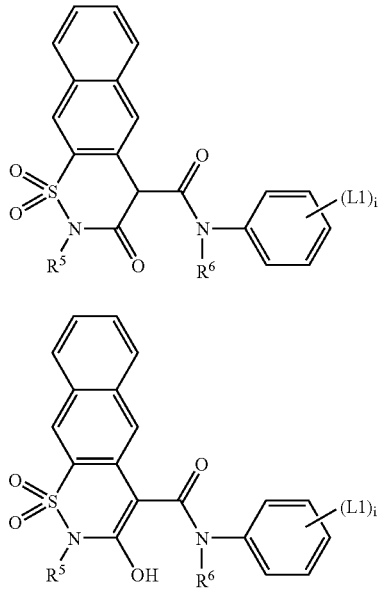

wherein
R⁵ is selected from the group consisting of H, $C_{1-4}$-alkyl, $C_{3-6}$-cycloalkyl, $C_{3-6}$-cycloalkyl-$C_{1-3}$-alkyl, phenyl and phenyl-$C_{1-3}$-alkyl, wherein the phenyl ring of the phenyl or the phenyl-alkyl group may be substituted with one or more substituents independently selected from the group consisting of F, Cl, Br, CN, $CF_3$, $C_{1-4}$-alkyl, $C_{1-4}$-alkoxy, $C_{1-4}$-alkylcarbonyl;

R⁶ is H or $C_{1-4}$-alkyl;

L1 is each independently selected from the group consisting of $C_{1-4}$-alkyl, $C_{1-3}$-alkoxy, F, Cl, Br, CN, $NO_2$ and $CF_3$, with the proviso that L1 is not Cl in para-position if index i is 1 and R⁵ is methyl;

i is 0, 1, 2, 3, 4 or 5;

or a pharmaceutically acceptable salt thereof.

Another further aspect of the present invention is a compound selected from the formulas I.5.1a, I.5.1b, I.6.1a and I.6.1b

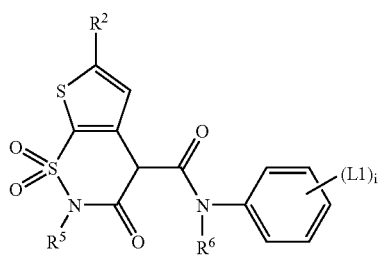

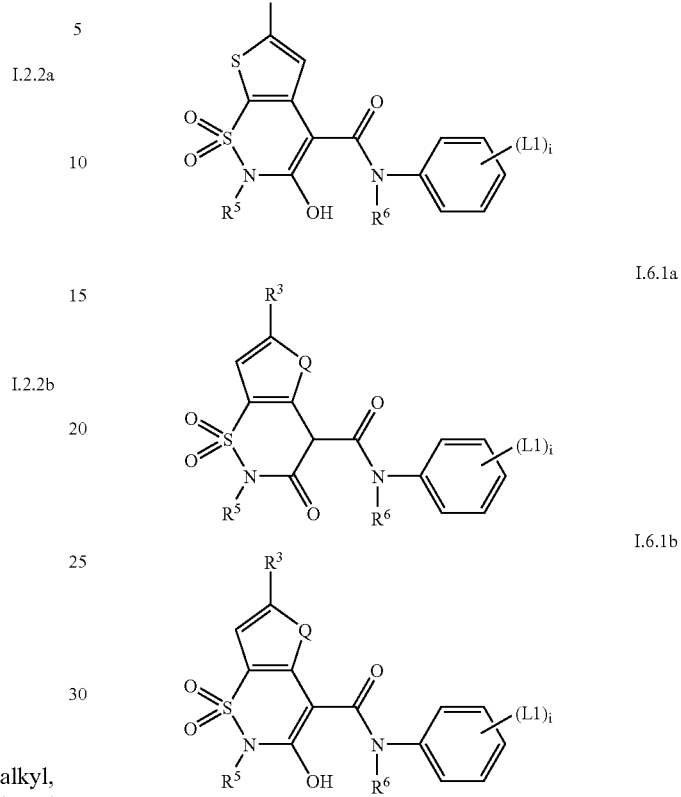

wherein
Q is O or S;
R², R³ are independently selected from the group consisting of F, Br, CN, $CF_3$, $C_{1-4}$-alkyl and $C_{1-4}$-alkoxy;
R⁵ is selected from the group consisting of H, $C_{1-4}$-alkyl, $C_{3-6}$-cycloalkyl, $C_{3-6}$-cycloalkyl-$C_{1-3}$-alkyl, phenyl and phenyl-$C_{1-3}$-alkyl, wherein the phenyl ring of the phenyl or the phenyl-alkyl group may be substituted with one or more substituents independently selected from the group consisting of F, Cl, Br, CN, $CF_3$, $C_{1-4}$-alkyl, $C_{1-4}$-alkoxy, $C_{1-4}$-alkylcarbonyl;
R⁶ is H or $C_{1-4}$-alkyl;
L1 is each independently selected from the group consisting of $C_{1-4}$-alkyl, $C_{1-3}$-alkoxy, F, Cl, Br, CN, $NO_2$ and $CF_3$, with the proviso that L1 is not Cl in para-position if index i is 1 and R⁵ is methyl;
i is 0, 1, 2, 3, 4 or 5;
or a pharmaceutically acceptable salt thereof.

These new compounds of the formulas I.3a, I.3b, I.4a, I.4b, IIa, IIb, I.2.2a, I.2.2b, I.5.1a, I.5.1b, I.6.1a, and I.6.1b belong to the group of compounds as described by the formulas Ia and Ib and thus also possess valuable Aβ lowering activity, in particular $A\beta_{42}$ lowering activity, a γ-secretase modulating activity and/or an activity to change the ratio of levels of isoforms of Aβ.

DETAILED DESCRIPTION OF THE INVENTION

The term "compound of the invention" refers to a compound selected from the formula Ia and Ib as defined hereinbefore and hereinafter.

The term "mammal" refers to rats, mice, guinea pigs, hares, dogs, cats, sheep, horses, pigs, cattle, cows, monkeys and also humans. In particular the term "mammal" refers to humans.

The terms "level of Aβ," "level of isoforms of Aβ," "Aβ level," etc., refer to a level of the specified Aβ isoform as determined for example in plasma fluid, brain fluid, cerebrospinal fluid (CSF) or in neurons or glia. Suitable methods for the determination of levels of Aβ are known by the person skilled in the art and are described in the scientific literature. For example suitable methods are ELISA and mass spectrometry.

The terms "increased level of Aβ," "increased level of isoforms of Aβ," etc., refer to those levels of isoforms of Aβ as described above which are elevated in an individual diagnosed having or developing a disease or conditions according to this invention, in particular with diagnosed Alzheimer's disease, compared to individuals diagnosed not having or developing such a disease or condition.

In the following the groups and substituents V, W, Q, Y, $R^1$, $R^2$, $R^3$, $R^4$, $R^5$, $R^6$, L1, L2, L3, and the indizes i, j, and k are defined as hereinbefore and hereinafter.

Substituents and groups which appear twice or more in a formula may have the same or different meanings as defined.

According to a first embodiment of the present invention the compound administered is chosen from the formulas I.1a, I.1b, preferably from the formula I.1a,

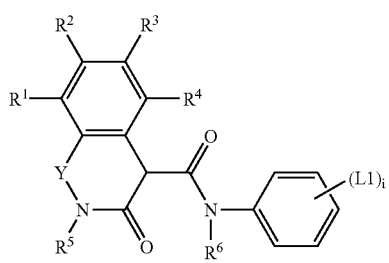

I.1a

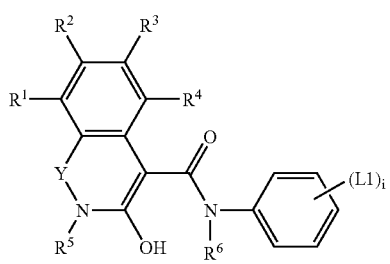

I.1b wherein the group Y, the substituents $R^1$, $R^4$, $R^5$, $R^6$ and L1 and the index i are defined as hereinbefore and hereinafter, and $R^2$, $R^3$ are each independently selected from the group consisting of H, F, Cl, Br, CN, $CF_3$, $C_{1-4}$-alkyl and $C_{1-4}$-alkoxy; or or a pharmaceutically acceptable salt thereof.

According to a second embodiment of the present invention the compound administered is chosen from the formulas I.2a, I.2b, preferably from the formula I.2a,

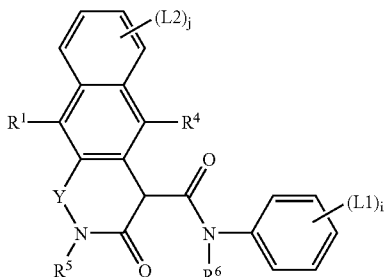

I.2a

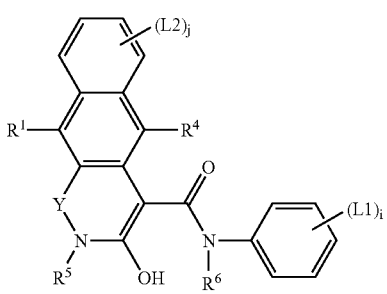

I.2b wherein the group Y, the substituents $R^1$, $R^4$, $R^5$, $R^6$, L1 and L2 and the index i are defined as hereinbefore and hereinafter, wherein j is 0, 1, 2, 3 or 4;

or a pharmaceutically acceptable salt thereof.

According to a third embodiment of the present invention the compound administered is chosen from the formulas I.3a, I.3b, I.4a, I.4b

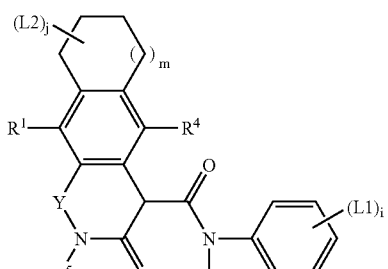

I.3a

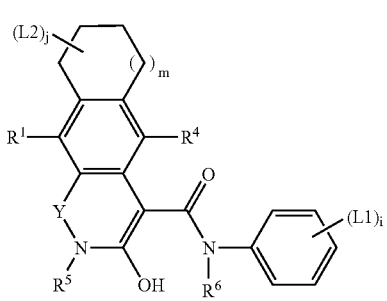

I.3b

-continued

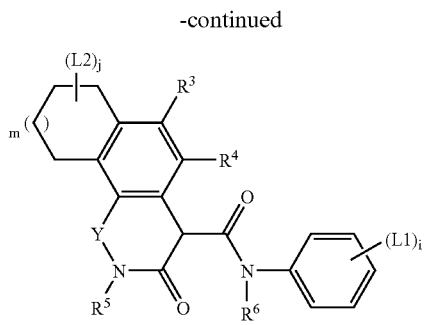

I.4a

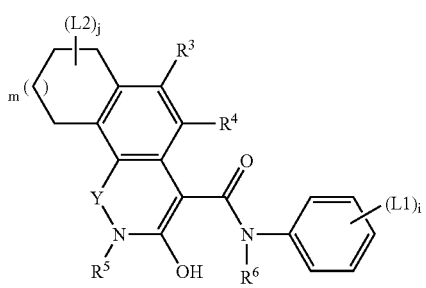

I.4b wherein the group Y, the substituents $R^1$, $R^3$, $R^4$, $R^5$, $R^6$, L1 and L2 and the index i are defined as hereinbefore and hereinafter, j is 0, 1, 2 or 3; and m is 0, 1 or 2;

or a pharmaceutically acceptable salt thereof.

The index j is preferably 0, 1 or 2, in particular 0 or 1. Most preferably the index j is 0.

The index m is preferably 0 or 1, most preferably 1.

In said third embodiment the compounds of the formulas I.3a and I.3b, in particular of I.3a are preferred.

According to a fourth embodiment of the present invention the compound administered is chosen from the formulas I.5a, I.5b, I.6a, I.6b

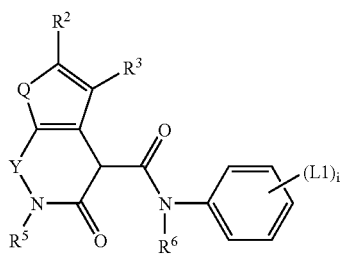

I.5a

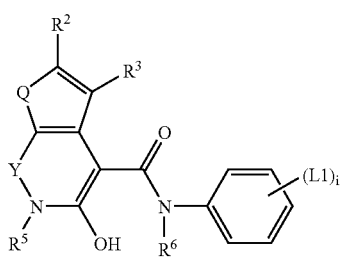

I.5b

-continued

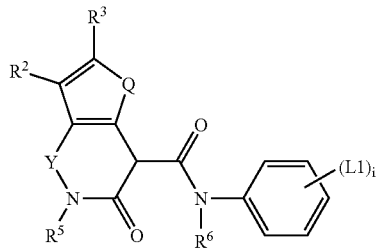

I.6a

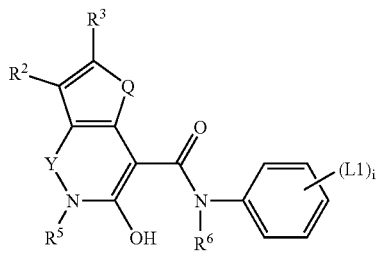

I.6b wherein the groups Q and Y, the substituents $R^5$, $R^6$ and L1 and the index i are defined as hereinbefore and hereinafter, $R^2$, $R^3$ are each independently selected from the group consisting of H, F, Cl, Br, CN, $CF_3$, $C_{1-4}$-alkyl and $C_{1-4}$-alkoxy; or or a pharmaceutically acceptable salt thereof.

In the fourth embodiment the compounds of the formulas I.5a and I.5b, in particular of I.5a are preferred.

In said fourth embodiment the preferred meaning of the group Q is S.

In the method according to this invention those compounds are preferably administered in which the group Y is a sulfonyl group.

In the first embodiment of the present invention the group Y is a sulfonyl or a carbonyl group.

In the method according to this invention those compounds are preferably administered in which the group $R^5$ is selected from the group consisting of H, methyl, ethyl, cyclopropyl, phenyl and phenylmethyl, wherein the phenyl ring in the phenyl group or phenylmethyl group may be substituted with one, two or more substituents selected from the group consisting of F, Cl, Br, CN, $CF_3$, $C_{1-4}$-alkyl, $C_{1-4}$-alkoxy or $C_{1-4}$-alkyl-carbonyl.

Preferred meanings of the group $R^5$ are H, methyl, ethyl, cyclopropyl, phenyl and phenylmethyl, wherein the phenyl ring in the phenyl group or phenylmethyl group is unsubstituted or is substituted with one, two or three substituents selected from the group consisting of F, Cl, Br, CN, $CF_3$ and methyl.

In the method according to this invention those compounds are preferably administered in which the group $R^6$ is H or methyl, most preferably H.

Therefore in the method according to the first embodiment preferred compounds are selected from the formulas I.1.1a, I.1.1b, in particular of the formula I.1.1a

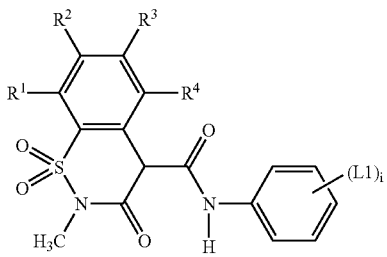

I.1.1a

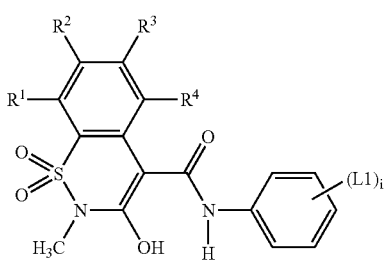

I.1.1b wherein the substituents $R^1$, $R^4$ and L1 and the index i are defined as hereinbefore and hereinafter, $R^2$, $R^3$ are each independently selected from the group consisting of H, F, Cl, Br, CN, $CF_3$, $C_{1-4}$-alkyl and $C_{1-4}$-alkoxy;

or a pharmaceutically acceptable salt thereof.

In the method according to the second embodiment preferred compounds are selected from the formulas I.2.1a, I.2.1b, in particular of the formula I.2.1a

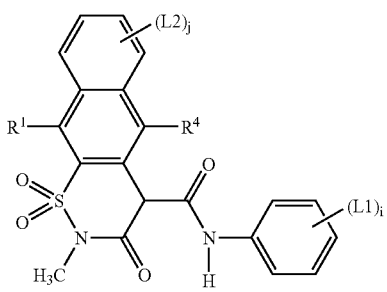

I.2.1a

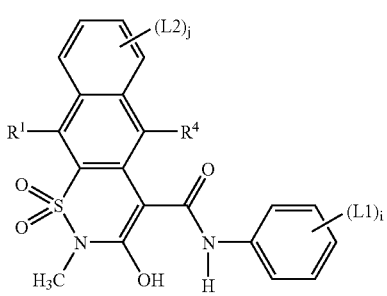

I.2.1b wherein the substituents $R^1$, $R^4$, L1 and L2 and the index i are defined as hereinbefore and hereinafter, wherein j is 0, 1, 2, 3 or 4;

or a pharmaceutically acceptable salt thereof.

In the method according to the third embodiment preferred compounds are selected from the formulas I.3.1a, I.3.1b, in particular of the formula I.3.1a

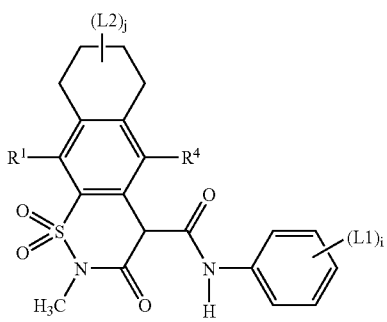

I.3.1a

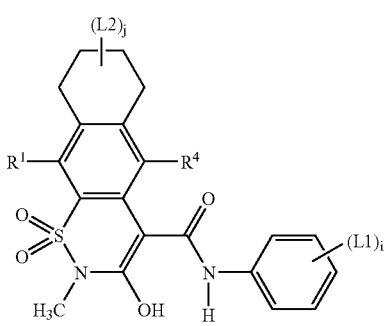

I.3.1b wherein the substituents $R^1$, $R^4$, L1, L2 and the index i are defined as hereinbefore and hereinafter, j is 0, 1, 2 or 3 or a pharmaceutically acceptable salt thereof.

In the method according to this invention those compounds with substituents $R^1$, $R^2$, $R^3$ and/or $R^4$ are preferably administered in which said prevalent groups $R^1$, $R^2$, $R^3$, $R^4$ are selected from the group consisting of H, F, Cl and methyl.

Furthermore In the method according to this invention preferred meanings of the substituents L1 and where applicable also L2 and/or L3 are F, Cl, Br, CN, $CF_3$.

In the compounds administered according to the present invention the index i is preferably 0, 1, 2 or 3; most preferably 0, 1 or 2; in particular 1 or 2.

In the compounds administered according to the present invention the index j, where applicable, is preferably 0, 1 or 2; most preferably 0 or 1; in particular 0.

In the following table examples of compounds according to the formula Ia, Ib are listed:

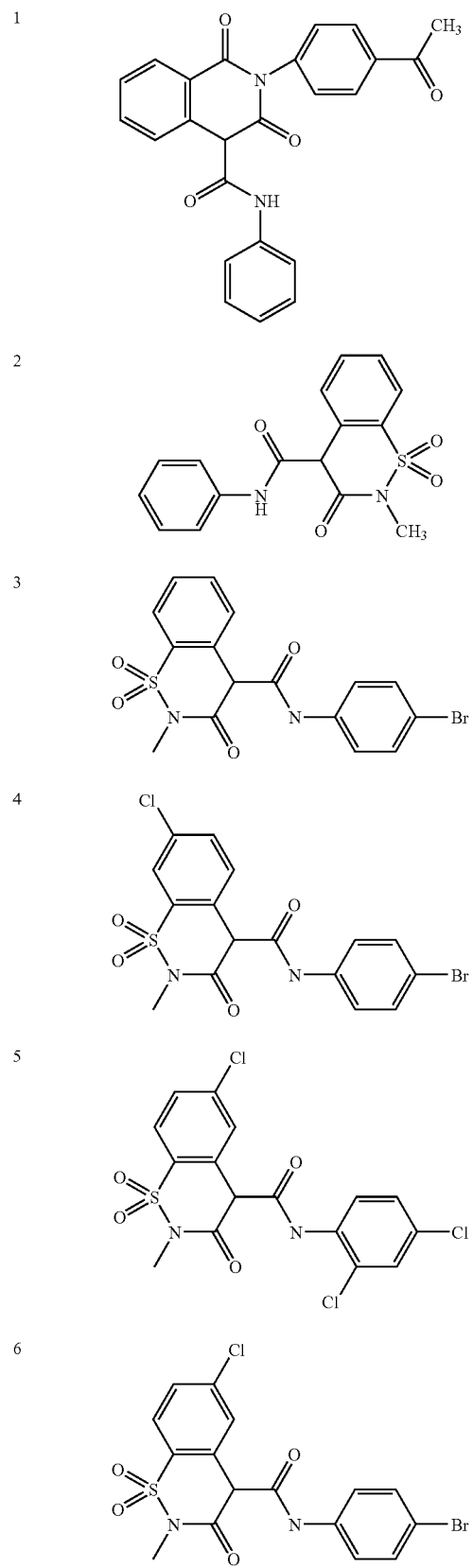
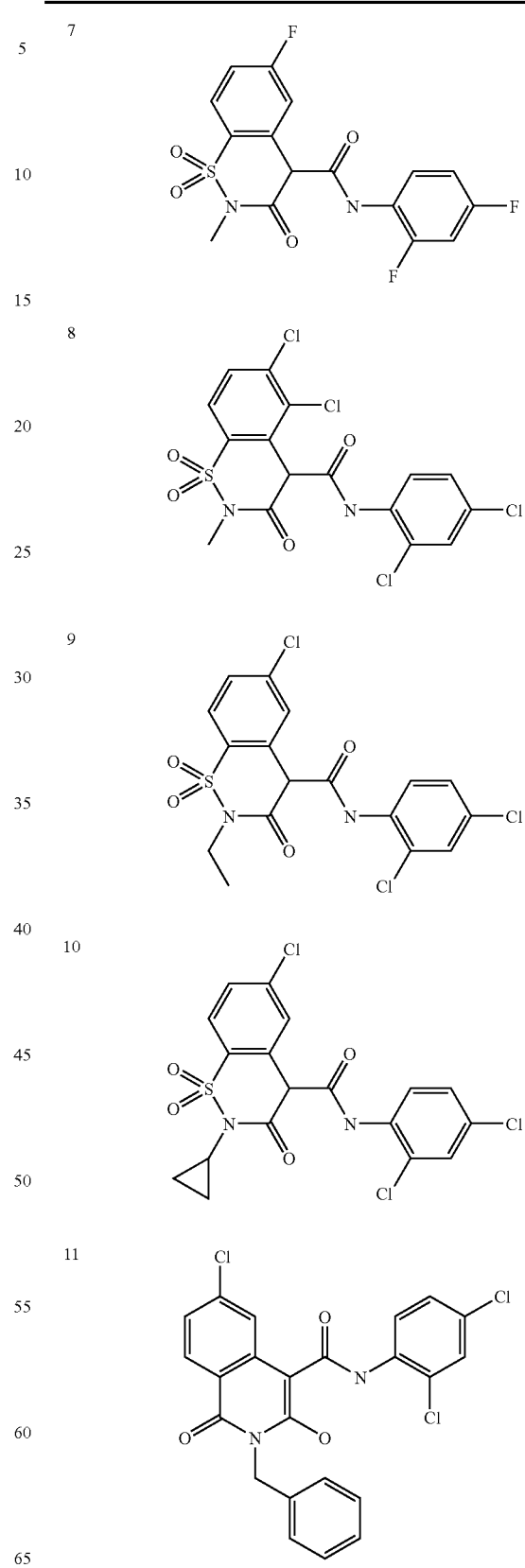

-continued
| | |
|---|---|
| 12 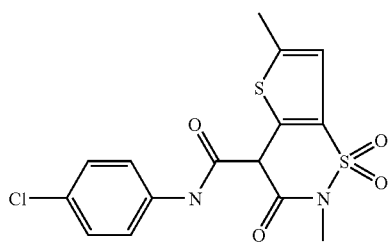 | 17 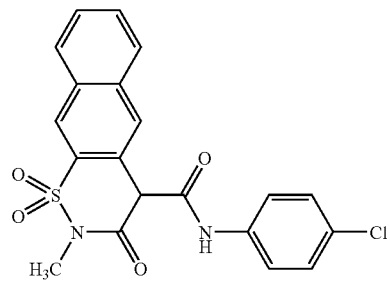 |
| 13 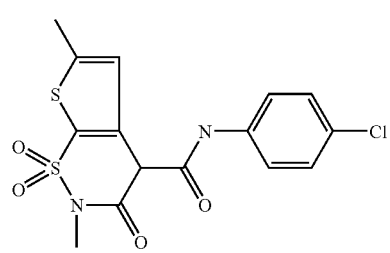 | 18 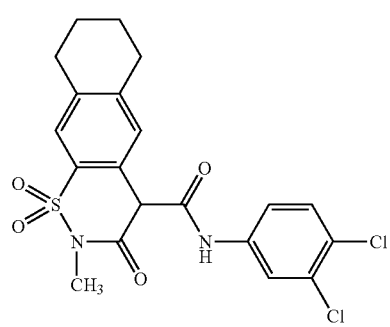 |
| 14 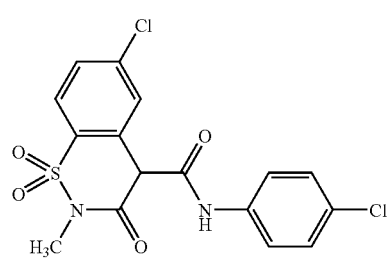 | 19 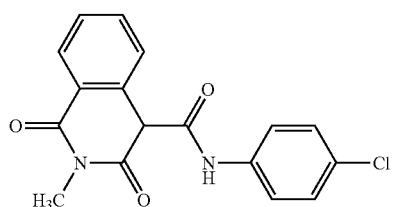 |
| 15 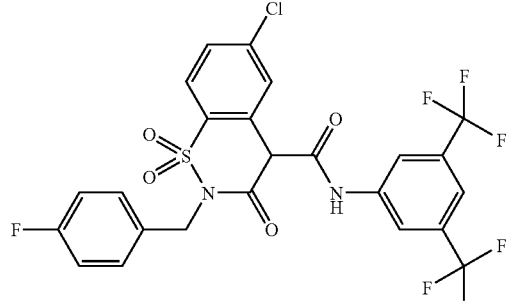 | 20 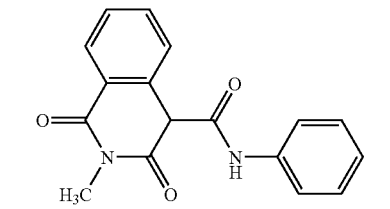 |
| | 21 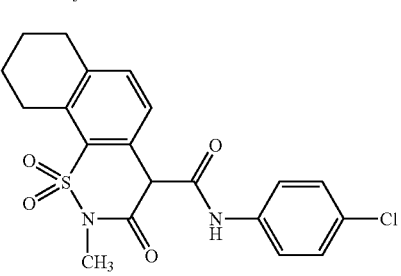 |
| 16 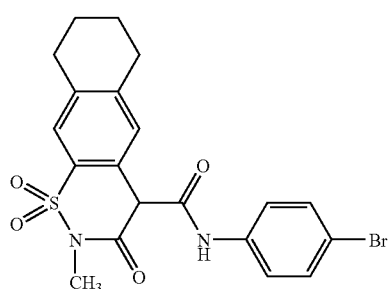 | 22 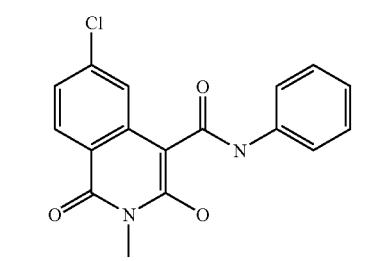 |

-continued
23 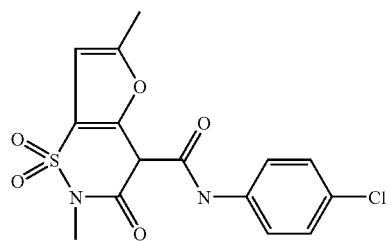
24 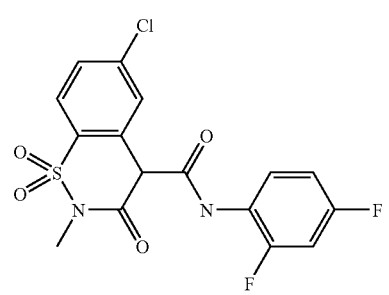
25 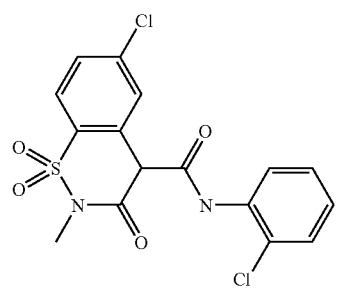
26 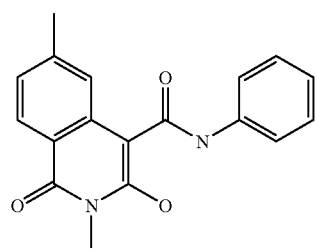
27 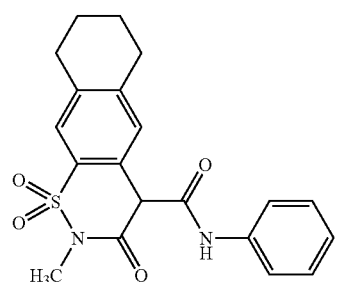
-continued
28 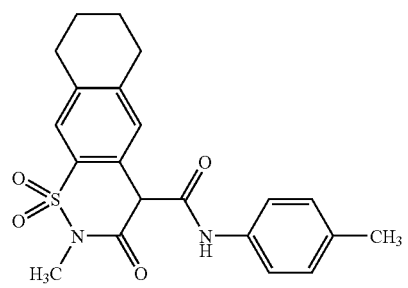
29 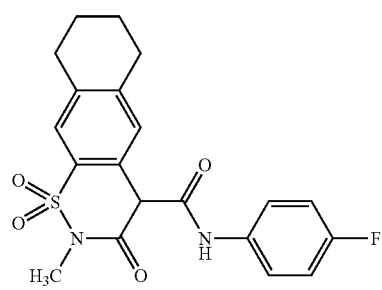
30 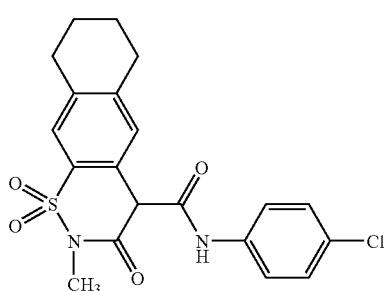
31 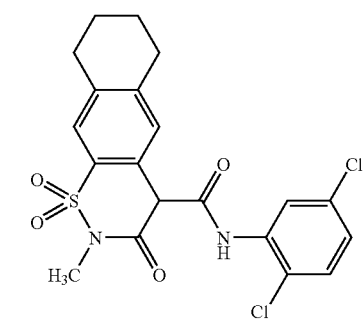
32 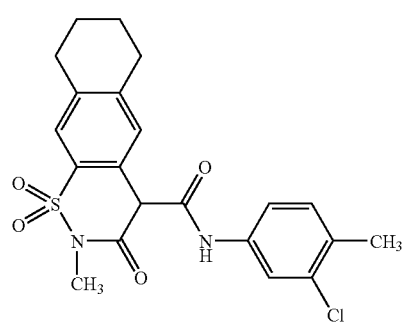

| | |
|---|---|
| 33 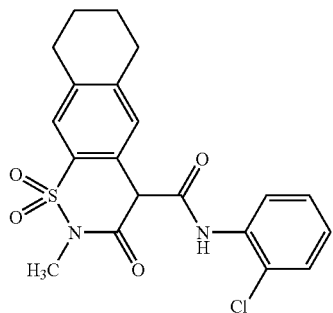 | 37 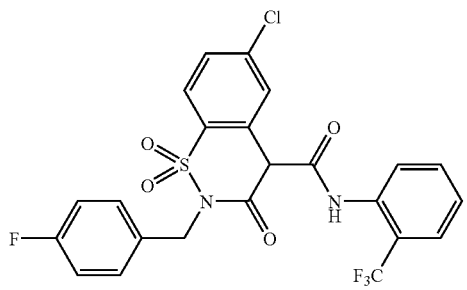 |
| 34 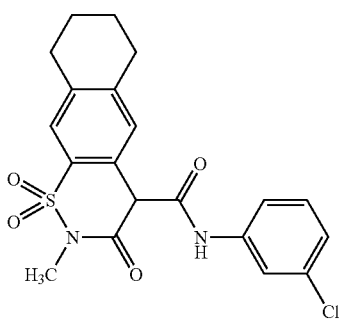 | 38 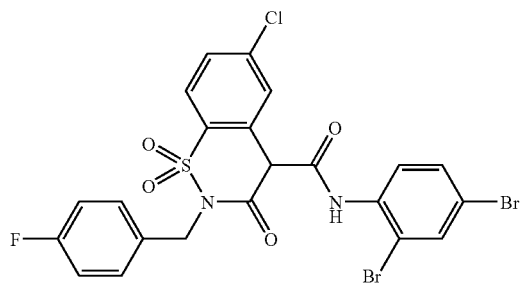 |
| 35 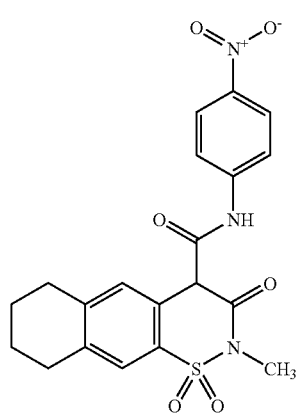 | 39 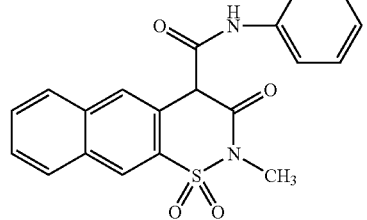 |
| | 40 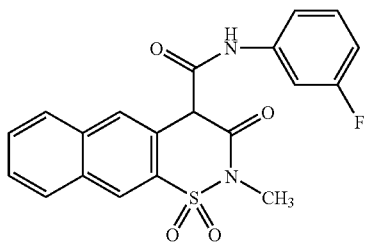 |
| | 41 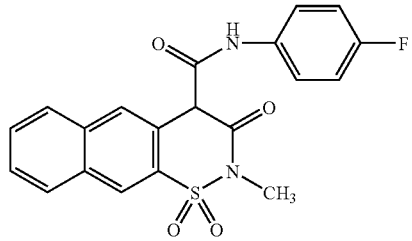 |
| 36 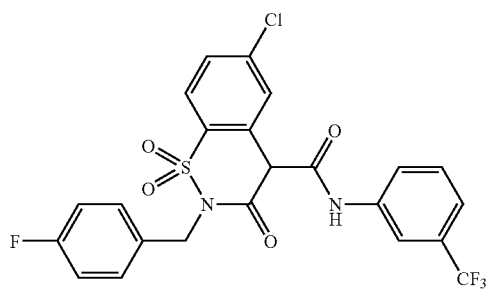 | 42 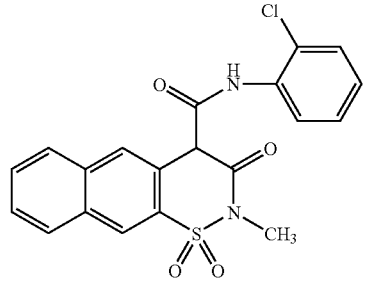 |

-continued
43 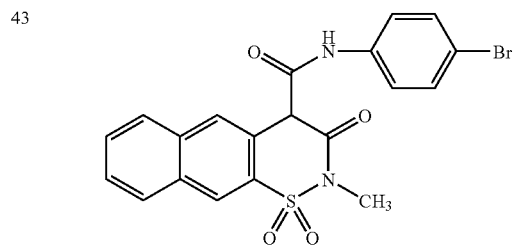
44 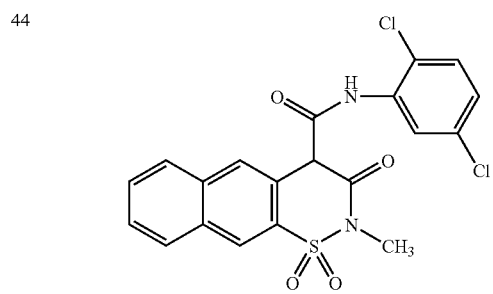
45 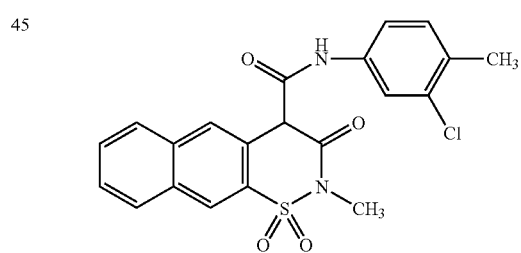
46 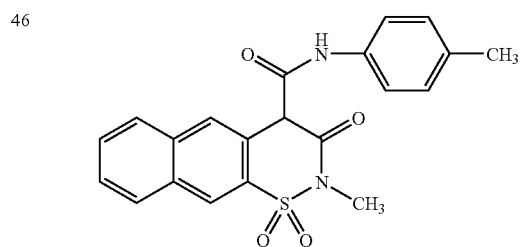
47 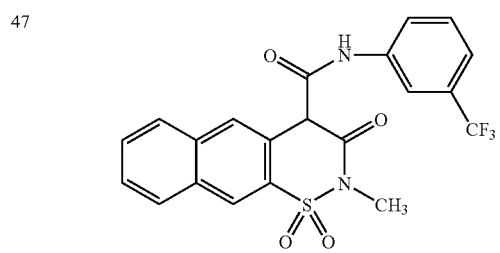
48 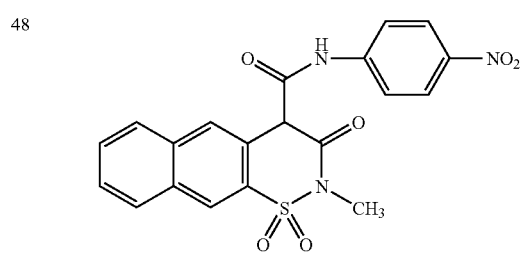
-continued
49 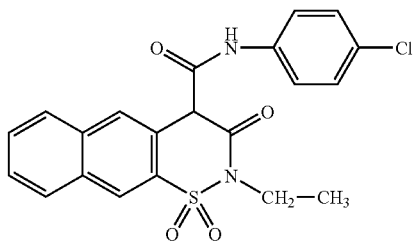
50 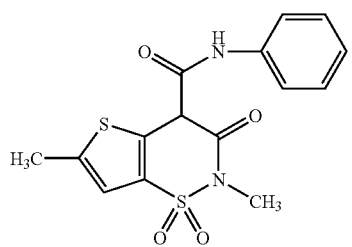
51 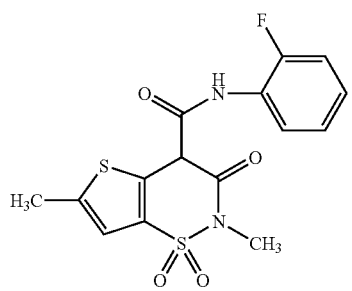
52 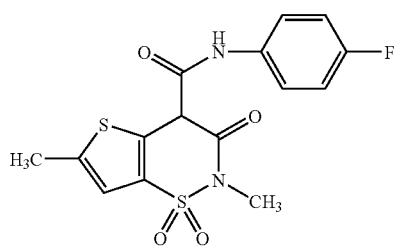
53 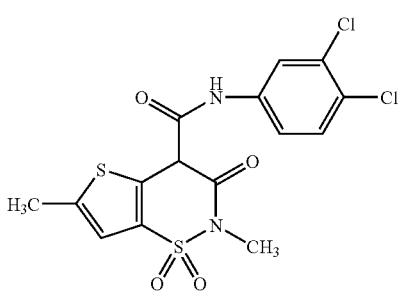
54 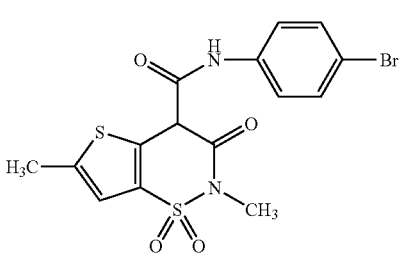

| | | | |
|---|---|---|---|
| 55 | 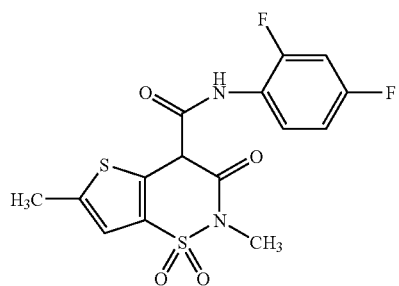 | 61 | 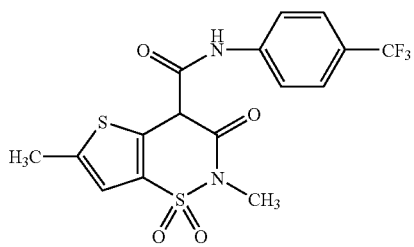 |
| 56 | 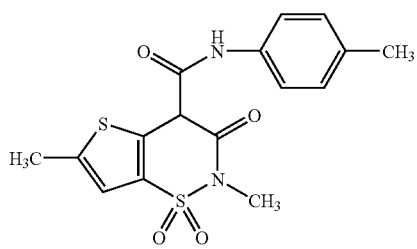 | 62 | 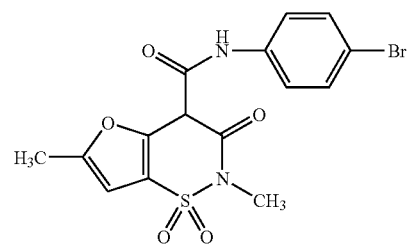 |
| 57 | 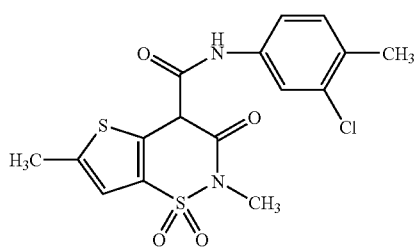 | 63 | 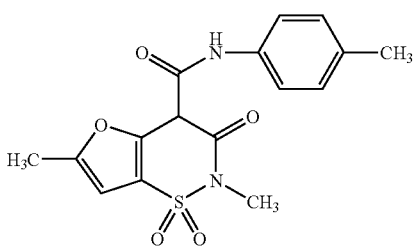 |
| 58 | 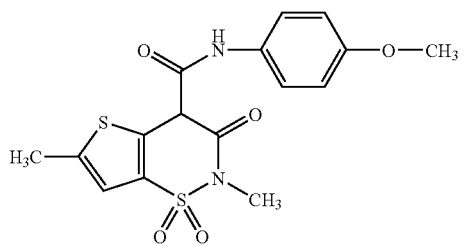 | 64 | 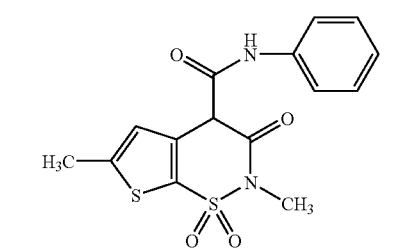 |
| 59 | 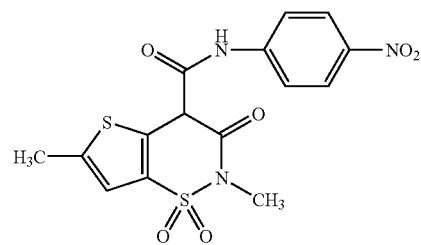 | 65 | 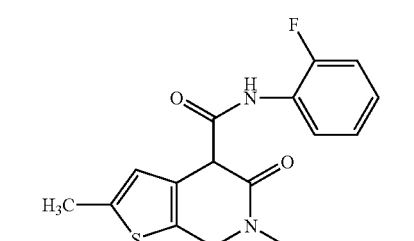 |
| 60 | 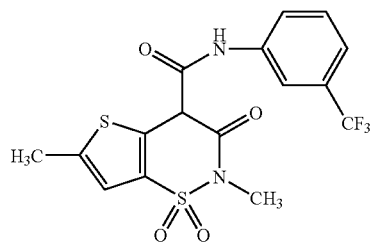 | 66 | 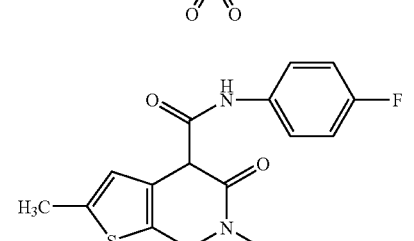 |

-continued

67
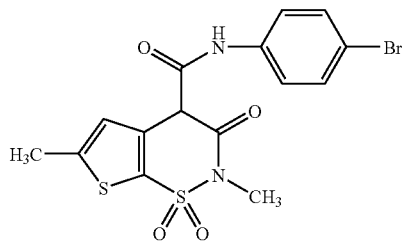

68
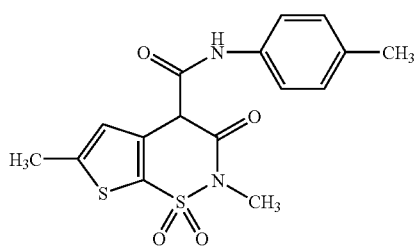

69
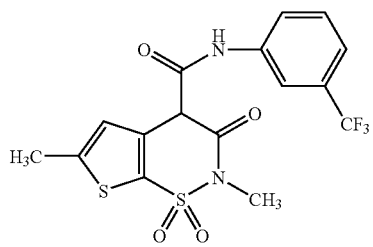

70
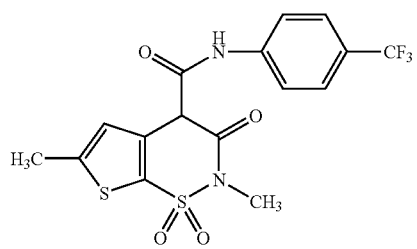

In the above table the compounds (1) to (23), in particular (1) to (18) are preferred.

The method according to the present invention is advantageously suited to treat or prevent a disease or condition which is associated with an increased level of a pathogenic isoform of Aβ, in particular of Aβ$_{42}$, or with a changed ratio of levels of Aβ isoforms, in particular by a changed ratio of a level of Aβ$_{40}$ to Aβ$_{42}$, or with the formation of plaques containing one or more isoforms of Aβ, in particular fibrillar Aβ isoforms, especially of Aβ$_{42}$.

Diseases or conditions which according to this invention can advantageously be treated or prevented are selected from the group consisting of diseases associated with the formation of diffuse and senile plaques, amyloidosis associated with the formation of Aβ isoforms, brain amyloidosis, vascular amyloidosis, age related amyloidosis, and central or peripheral amyloid diseases.

Further diseases or conditions which according to this invention can advantageously be treated or prevented are selected from the group consisting of Alzheimer's disease, Down's syndrome, MCI ("Mild Cognitive Impairment"), Heriditary Cerebral Hemorrhage with Amyloidosis of the Dutch-Type, Cerebral Amyloid Angiopathy, Traumatic Brain Injury, Stroke, Dementia, Dementia of Alzheimer type (DAT), age associated memory impairment (AAMI), Parkinson's Disease and Parkinson's Syndrome, and diffuse Lewy body type AD.

The method according to this invention is particularly of advantage in the treatment or prevention of Alzheimer's disease.

Furthermore the method of this invention is particularly suitable in the treatment or prevention of patients diagnosed both with Alzheimer's disease and a disease associated with inflammatory conditions, in particular Parkinson's disease, when a compound or composition according to this invention is administered which exhibits a COX-2 inhibiting activity, in particular which inhibits COX-2 selectively.

Accordingly the present invention is also related to the use of at least one compound selected from the formulas Ia, Ib as defined hereinbefore and hereinafter for the manufacture of a medicament for treating or preventing of a disease or condition associated with an increased level of one or more isoforms of amyloid β peptides (Aβ) and/or with a changed ratio of levels of Aβ isoforms and/or with the formation of plaques containing one or more amyloid β peptide (Aβ) isoforms in a mammal.

The present invention is also related to new compounds which possess valuable Aβ lowering activity, in particular Aβ$_{42}$ lowering activity, a γ-secretase modulating activity and/or an activity to change the ratio of levels of isoforms of Aβ.

According to a first embodiment the new compound is selected from the group of formulas I.3a, I.3b, I.4a, I.4b, in particular I.3a and I.4a I.3a
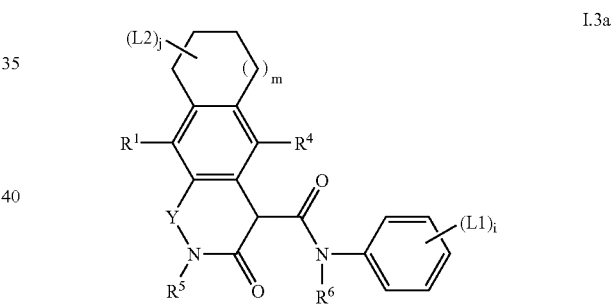

I.3b
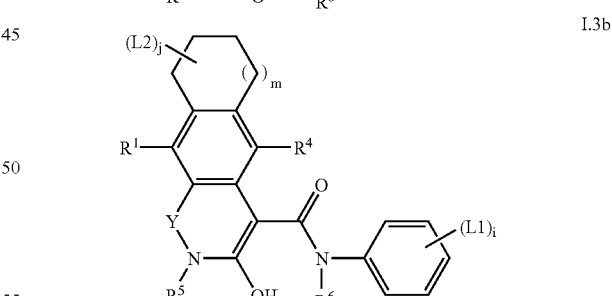

I.4a
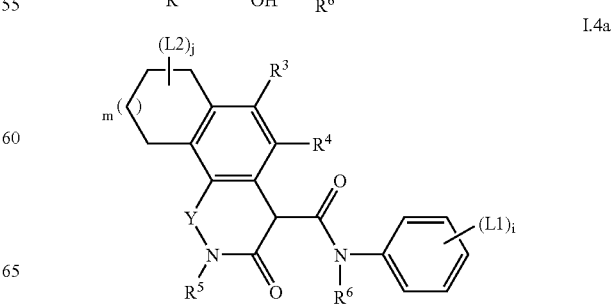

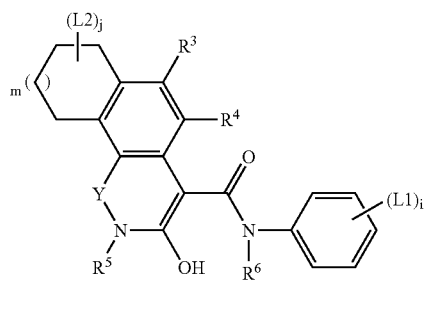

I.4b

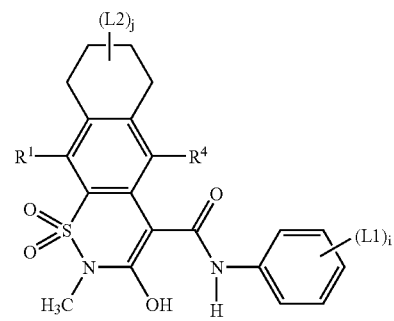

I.3.1b wherein the groups and substituents Y, $R^1$, $R^3$, $R^4$, $R^5$, $R^6$, L1, L2 and the indices i, j and m are defined as hereinbefore.

A preferred meaning of the group Y is sulfonyl.

Preferred meanings of the groups $R^1$ and $R^4$ or $R^3$ and $R^4$ are independently of each other H, F, Cl and methyl.

The substituent $R^5$ is preferably selected from the group consisting of H, methyl, ethyl, cyclopropyl, phenyl and phenylmethyl, wherein the phenyl ring in the phenyl group or phenylmethyl group is unsubstituted or substituted with 1, 2 or 3 substituents independently of each other selected from F, Cl, Br, $C_{1-4}$-alkyl and $C_{1-4}$-alkyl-carbonyl.

Most preferably $R^5$ is methyl.

A preferred meaning of the substituent $R^6$ is H.

Preferred meanings of the substituents L1 and L2 are independently of each other F, Cl, Br, CN, $CF_3$ and methyl, whereby L1 may also be $NO_2$. Most preferably L1 is selected from the group consisting of F, Cl, Br, $CH_3$ and $NO_2$.

The index i is preferably 0, 1, 2 or 3; most preferably 0, 1 or 2; in particular 1 or 2.

The index j is preferably 0, 1 or 2; most preferably 0 or 1; in particular j is 0.

The index m is preferably 0 or 1; most preferably 1.

Therefore the compounds of the formulas I.3a and I.3b are preferably described by the formulas I.3.1a, I.3.1b, in particular I.3.1a

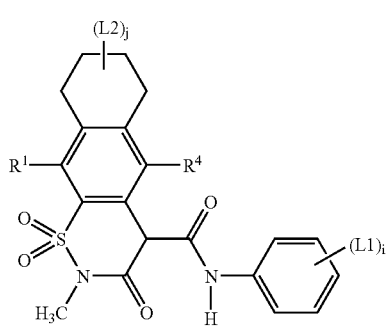

I.3.1a wherein the substituents $R^1$, $R^4$, L1 and L2 and the index i and j are defined as hereinbefore, including their pharmaceutically acceptable salts.

Examples of preferred compounds of the formulas I.3a, I.3b, I.4a, I.4b are (16)

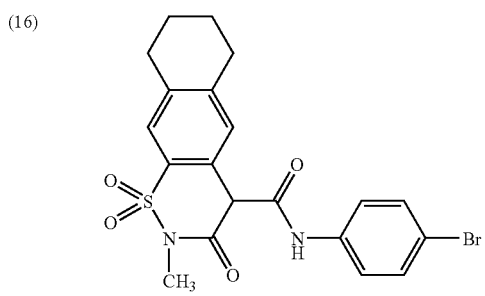

(18)

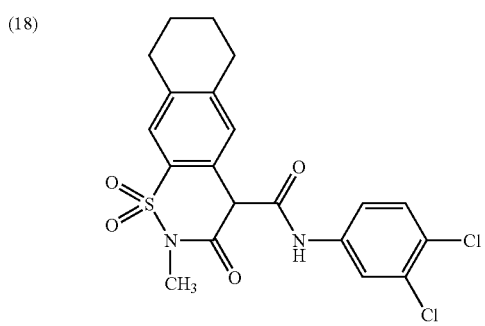

(21)

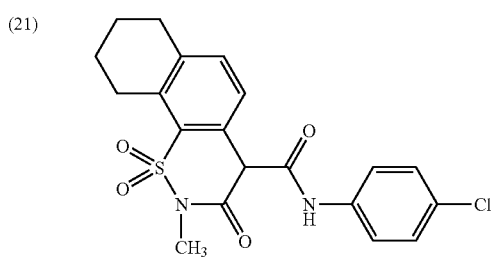

(27) 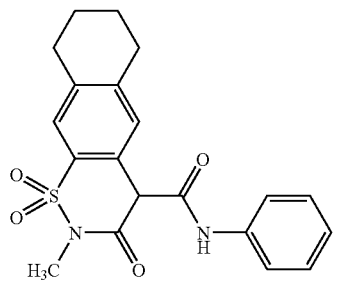
(28) 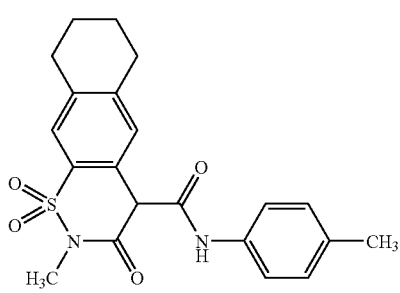
(29) 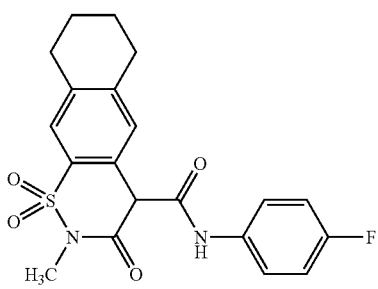
(30) 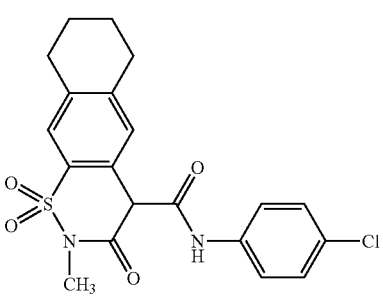
(31) 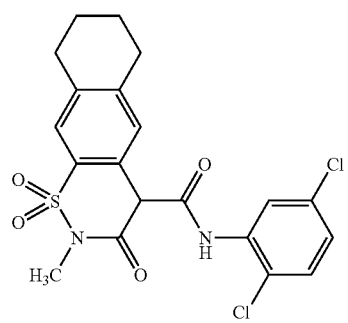
(32) 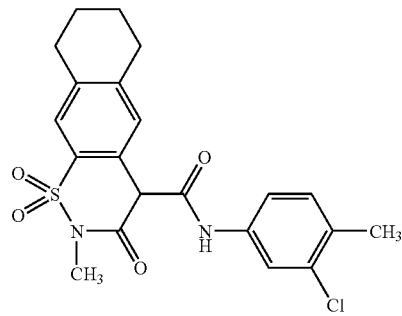
(33) 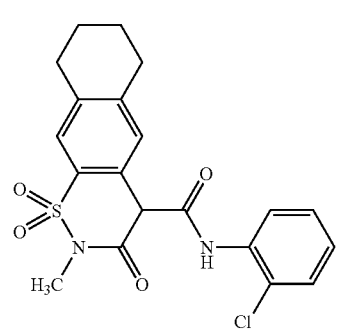
(34) 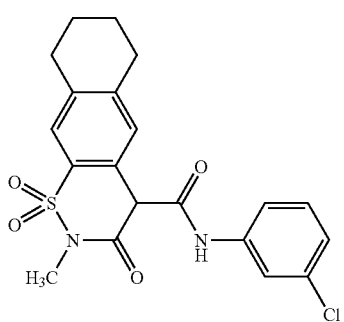
(35) 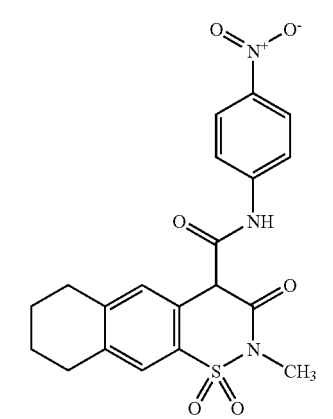
including their pharmaceutically acceptable salts.
According to a second embodiment the new compound is selected from the group of formulas IIa, IIb, in particular IIa

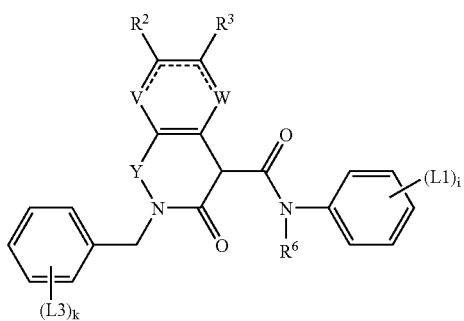

IIa

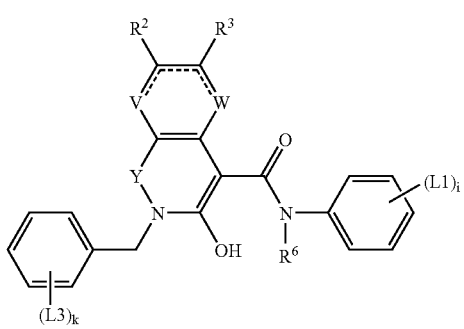

IIb wherein the groups V, W, Y, $R^2$, $R^3$, $R^6$, L1, L3 and the indices i and k are defined as hereinbefore, including their pharmaceutically acceptable salts.

Preferred compounds according to this embodiment are described by the formulas II.1a, II.1b, in particular II.1a

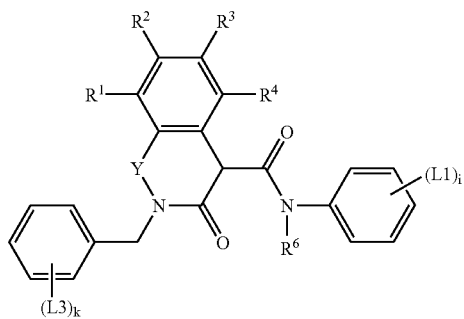

II.1a

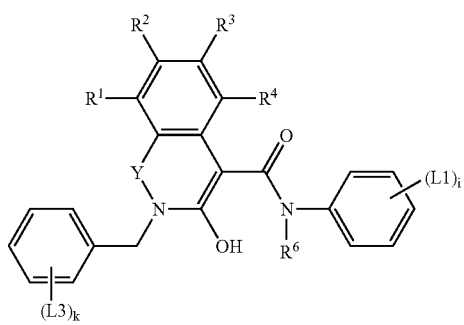

II.1b wherein the groups Y, $R^1$, $R^4$, $R^2$, $R^3$, $R^6$, L1, L3 and the indices i and k are defined as hereinbefore, including their pharmaceutically acceptable salts.

A preferred meaning of the group Y is sulfonyl.

A preferred meaning of the substituent $R^6$ is H.

Preferred meanings of the groups $R^1$, $R^2$, $R^3$, $R^4$ are independently of each other selected from the group consisting of H, F, Cl and methyl.

Preferred meanings of the substituents L1 and L3 are independently of each other F, Cl, Br, CN, $CF_3$ and methyl, whereby L1 may also be $NO_2$. Most preferably L3 is selected from the group consisting of F, Cl and Br. Most preferably L1 is selected from the group consisting of Cl, Br, $CH_3$ and $CF_3$.

The index i is preferably 0, 1, 2 or 3; most preferably 0, 1 or 2; in particular 1 or 2.

The index k is preferably 1, 2 or 3; most preferably 1 or 2.

A preferred example of a compound according to this second embodiment is (15)

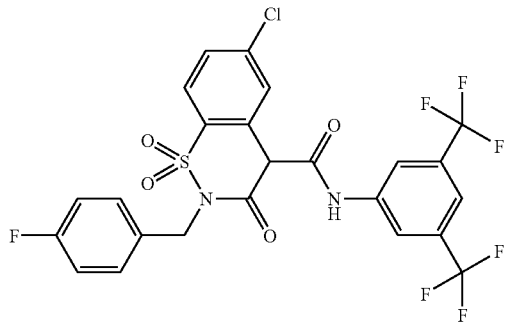

(36)

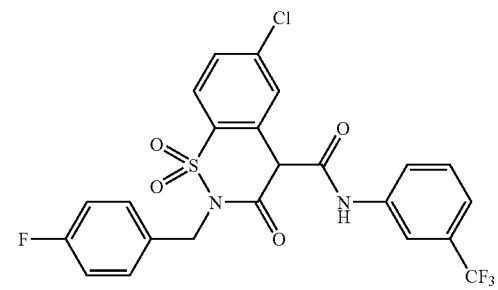

(37)

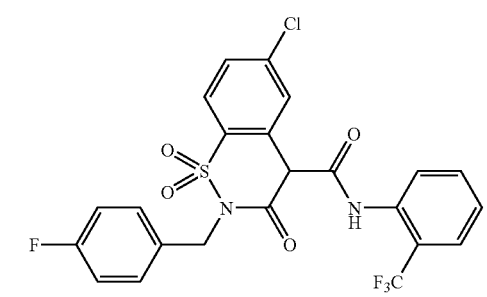

-continued

(38)
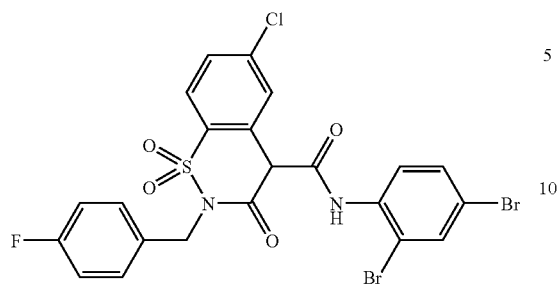

According to a third embodiment the new compound is selected from the group of formulas I.2.2a, I.2.2b, in particular I.2.2a I.2.2a
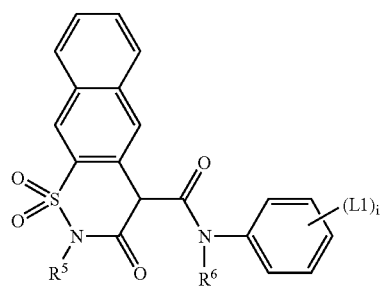

I.2.2b
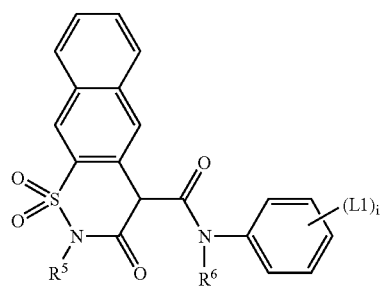

wherein the groups $R^5$, $R^6$, L1 and the index i are defined as for formulas I.2.2a and I.2.2b hereinbefore, including their pharmaceutically acceptable salts.

The substituent $R^5$ is preferably selected from the group consisting of H, $C_{1-4}$-alkyl, phenyl and phenyl-$C_{1-3}$-alkyl, wherein the phenyl ring of the phenyl or the phenyl-alkyl group may be substituted with one or more substituents independently selected from the group consisting of F, Cl, Br, CN, $CF_3$, $C_{1-4}$-alkyl, $C_{1-4}$-alkoxy, $C_{1-4}$-alkylcarbonyl.

More preferably $R^5$ is $C_{1-4}$-alkyl, most preferably $R^5$ is methyl or ethyl, in particular methyl.

A preferred meaning of $R^6$ is H.

Preferred meanings of the substituent L1 are independently of each other methyl, F, Cl, Br, $NO_2$ and $CF_3$, with the proviso that L1 is not Cl in para-position if index i is 1 and $R^5$ is methyl.

The index i is preferably 0, 1, 2 or 3, most preferably 0, 1 or 2, in particular 1 or 2.

Therefore the compounds of the formulas I.2.2a, I.2.2b are preferably described by the formulas I.2.3a, I.2.3b, I.2.4a, I.2.4b in particular I.2.3a, I.2.4a I.2.3a
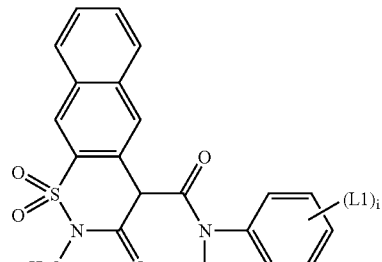

I.2.3b
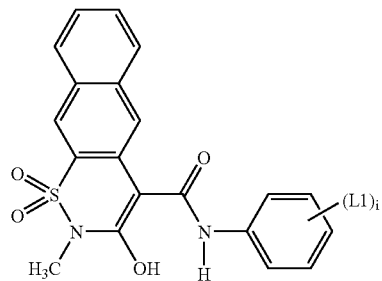

I.2.4a
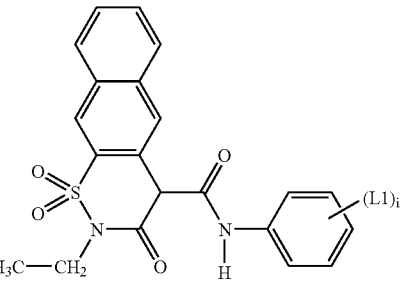

I.2.4b
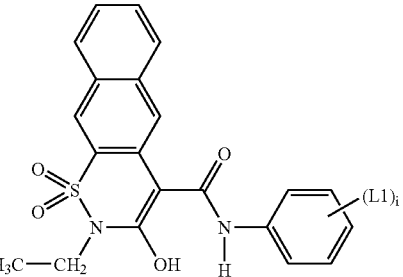

wherein the substituent L1 and the index i are defined as for formulas I.2.2a and I.2.2b hereinbefore, including their pharmaceutically acceptable salts.

Examples of preferred compounds of the formulas I.2.2a and I.2.2b are

39
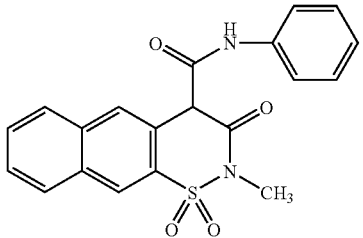

| | |
|---|---|
| 40 | 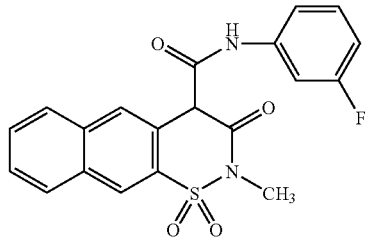 |
| 41 | 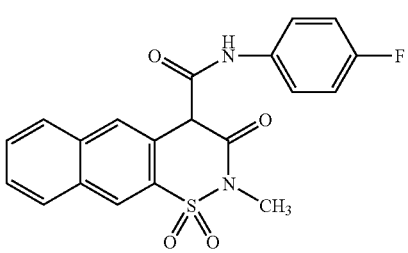 |
| 42 | 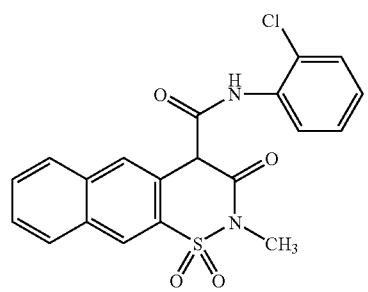 |
| 43 | 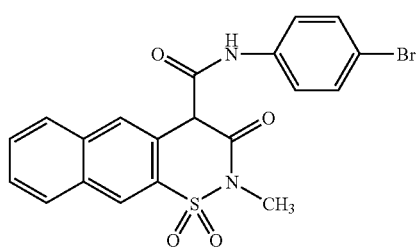 |
| 44 | 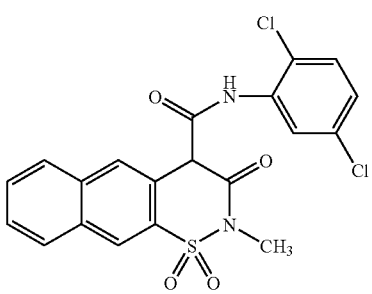 |
| 45 | 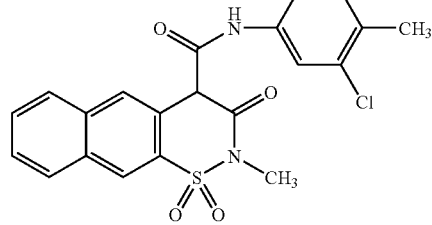 |
| 46 | 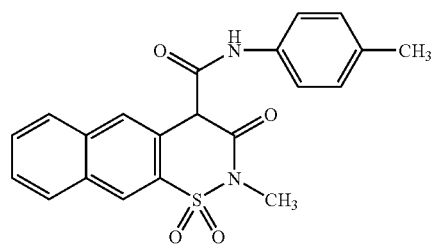 |
| 47 | 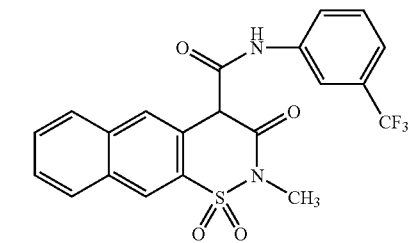 |
| 48 | 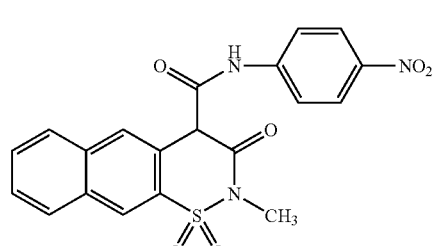 |
| 49 | 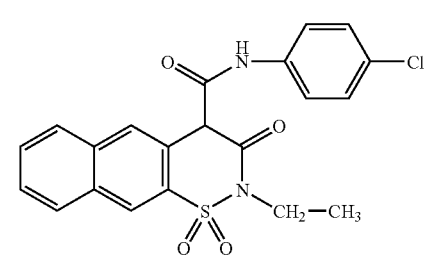 |
According to a forth embodiment the new compound is selected from the group of formulas I.5.1a, I.5.1b, I.6.1a, I.6.1b, in particular I.5.1a, I.6.1a
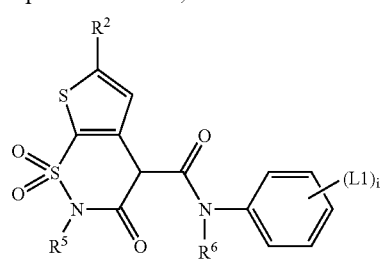
I.5.1a -continued

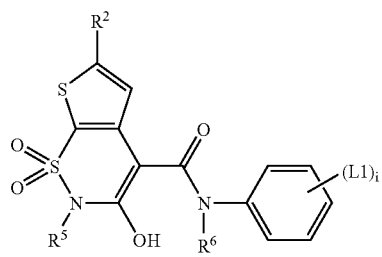
I.5.1b

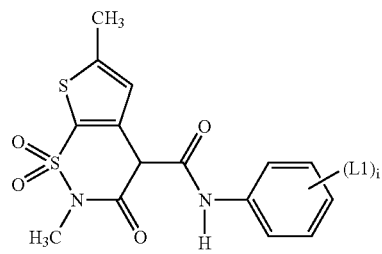
I.5.2a

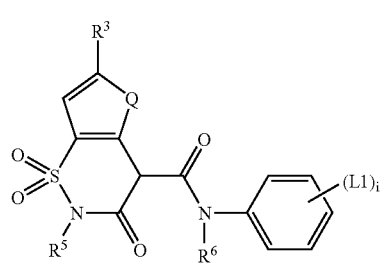
I.6.1a

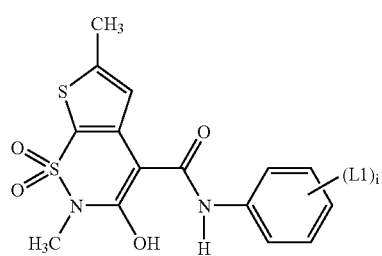
I.5.2b

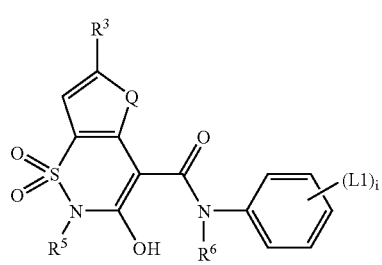
I.6.1b

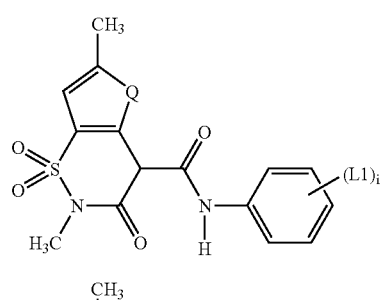
I.6.2a

I.6.2b wherein the groups Q, $R^2$, $R^3$, $R^5$, $R^6$, L1 and the index i are defined as for formulas I.5.1a, I.5.1b, I.6.1a, I.6.1b hereinbefore, including their pharmaceutically acceptable salts.

Preferably the meaning of substituent $R^2$, $R^3$ is $C_{1-4}$-alkyl, most preferably $R^2$, $R^3$ is methyl or ethyl.

The substituent $R^5$ is preferably selected from the group consisting of H, $C_{1-4}$-alkyl, phenyl and phenyl-$C_{1-3}$-alkyl, wherein the phenyl ring of the phenyl or the phenyl-alkyl group may be substituted with one or more substituents independently selected from the group consisting of F, Cl, Br, CN, $CF_3$, $C_{1-4}$-alkyl, $C_{1-4}$-alkoxy, $C_{1-4}$-alkylcarbonyl.

More preferably $R^5$ is $C_{1-4}$-alkyl, most preferably $R^5$ is methyl.

A preferred meaning of $R^6$ is H.

Preferred meanings of the substituent L1 are independently of each other methyl, methoxy, F, Cl, Br, $NO_2$ and $CF_3$, with the proviso that L1 is not Cl in para-position if index i is 1 and $R^5$ is methyl.

The index i is preferably 0, 1, 2 or 3, most preferably 0, 1 or 2, in particular 1 or 2.

Therefore the compounds of the formulas I.5.1a, I.5.1b, I.6.1a, I.6.1b are preferably described by the formulas I.5.2a, I.5.2b, I.6.2a, I.6.2b in particular I.5.2a, I.6.2a wherein the groups Q, L1 and the index i are defined as for formulas I.5.1a, I.5.1b, I.6.1a, I.6.1b hereinbefore, including their pharmaceutically acceptable salts.

Examples of preferred compounds of the formulas I I.5.1a, I.5.1b, I.6.1a, I.6.1b are

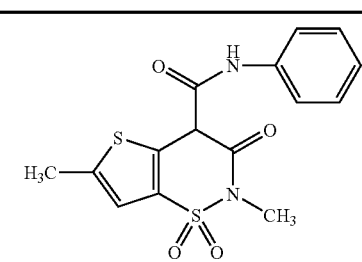
50

-continued
51
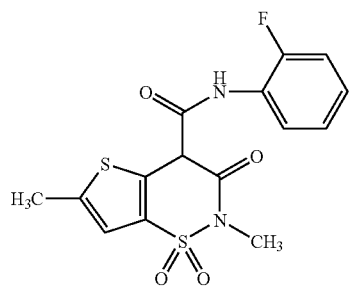
52
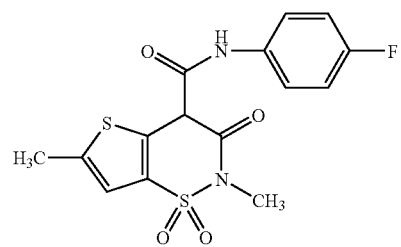
53
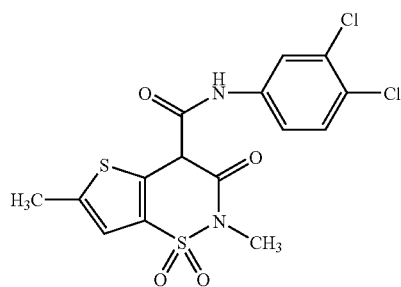
54
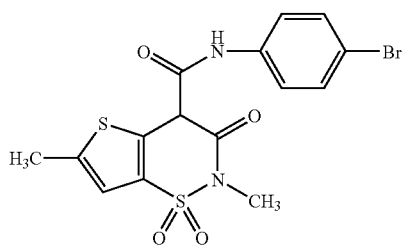
55
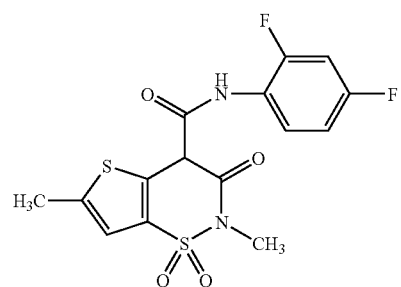
56
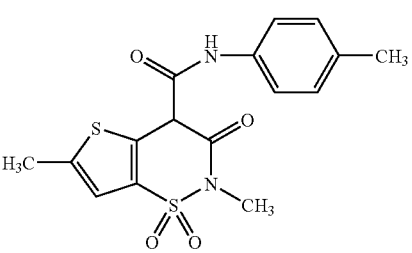
-continued
57
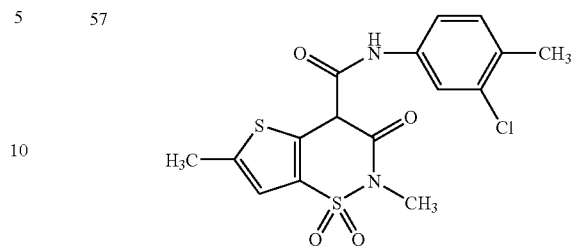
58
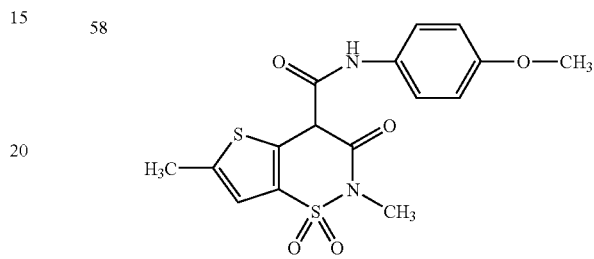
59
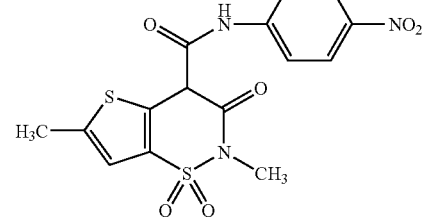
60
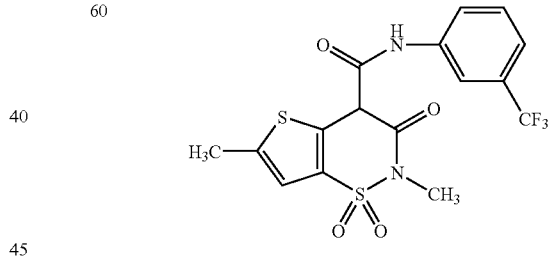
61
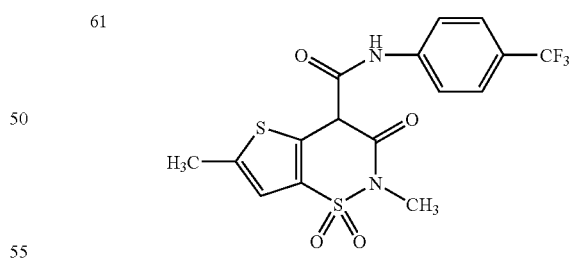
62
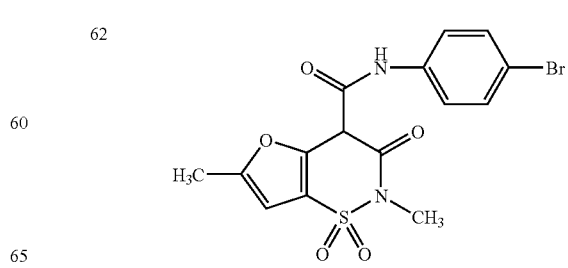

-continued

63
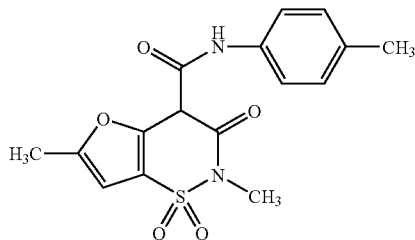

64
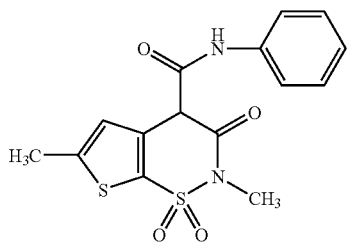

65
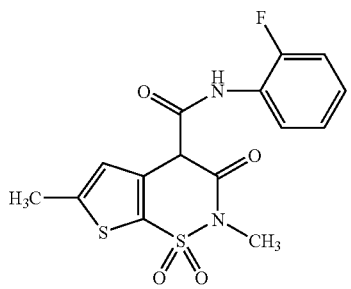

66
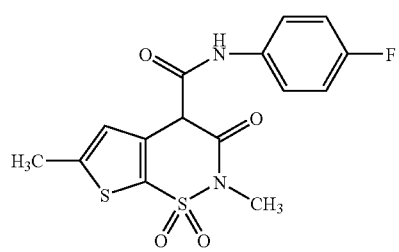

67
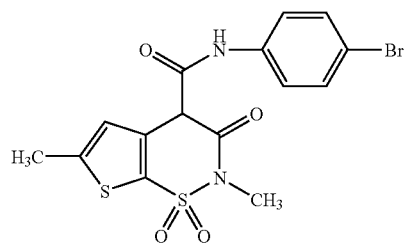

68
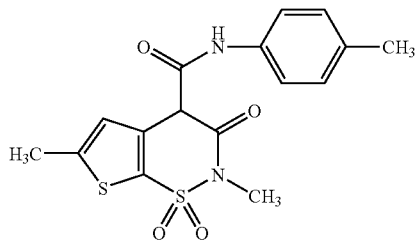

-continued

69
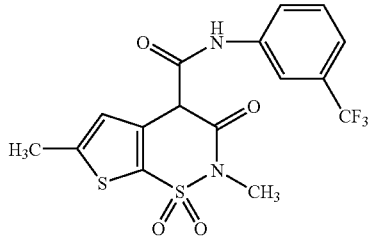

70
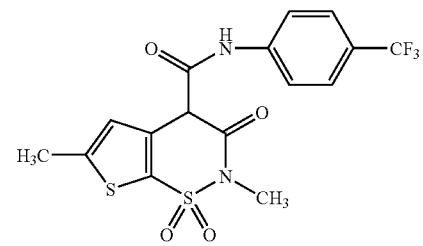

The present invention is also related to a pharmaceutical composition comprising at least one compound selected from the formulas Ia, Ib as defined hereinbefore and at least one pharmaceutically acceptable carrier or diluent. For this purpose, such a compound may be formulated, optionally together with other active substances as described hereinafter, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, granules, solutions, emulsions, syrups, aerosols for inhalation, ointments or suppositories.

Some expressions used hereinbefore and below to describe the compounds according to the invention will now be defined more fully.

The term halogen denotes an atom selected from among F, Cl, Br and I, particularly F, Cl and Br.

The term $C_{1-n}$-alkyl, where n has a value of 3 to 8, denotes a saturated, branched or unbranched hydrocarbon group with 1 to n C atoms. Examples of such groups include methyl, ethyl, n-propyl, iso-propyl, butyl, iso-butyl, sec-butyl, tert-butyl.

A ring structure which is depicted as

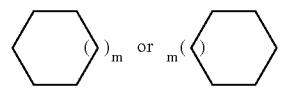

with m being 0, 1 or 2 indicates a cyclopentyl (m=0), a cyclohexyl (m=1) or a cycloheptyl (m=2) ring.

As used herein, the designation whereby a bond to a substituent, for example L, is drawn as emanating from the center of a ring, such as for example,

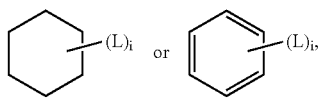

means that the ring is i-times substituted with the same or different substituents L which are attached to any free position on the ring that would otherwise be substituted by a hydrogen atom, unless specified otherwise.

The compounds according to this invention which are selected from the group of formulas Ia and Ib are made by methods well known to those skilled in the art from starting compounds known to those skilled in the art. The process chemistry is well known to those skilled in the art. Suitable reaction schemes and methods of synthesis are described for example in Lazer et al., J. Med. Chem. 1997, 40, 980-989 and in Lombardino et al., J. Med. Chem. 1971, 14, 973-977. Further synthesis methods of 3,4-dihydro-2H-1,2-benzothiazine 1,1-dioxide derivatives are described by Suh et al. in the U.S. Pat. No. 4,683,306 and by Lombardino in the U.S. Pat. No. 3,891,637.

An advantageous synthesis of the compounds according to this invention is described by the following reaction schemes.

Reaction scheme 1a:

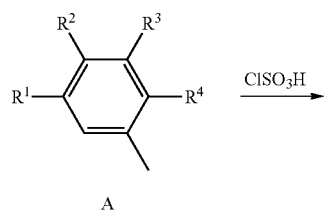

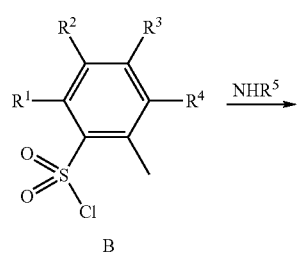

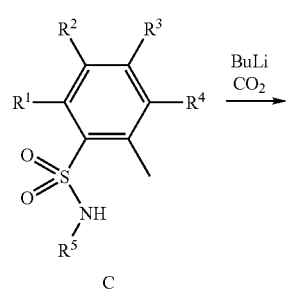

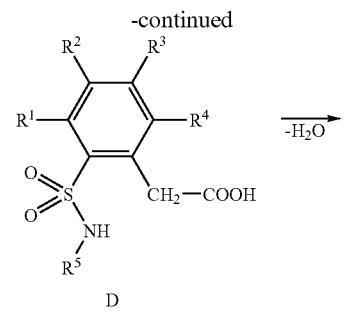

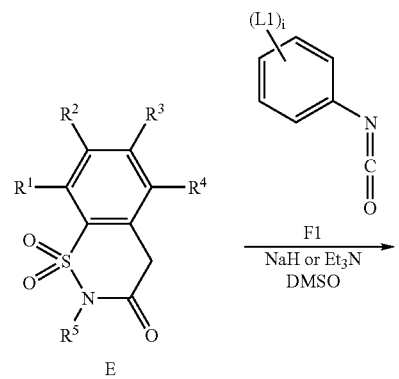

In the first step of the reaction scheme 1 a methyl substituted aromatic compound of the formula A wherein the substituents are defined as hereinbefore is sulfonylated to yield a compound B or the corresponding sulfonyl acid derivative. With respect to the synthesis of compounds of the formulas I.3a, I.3b, I.4a, I.4b the corresponding starting materials are for example methylated 1,2,3,4-tetrahydronaphthalene or indane compounds. The sulfonylation is performed advantageously using $ClSO_3H$ or a mixture of $ClSO_3H$ and $SO_2Cl_2$. Preferred reaction temperatures are in the range of −20° C. to +40° C., whereby the reaction is preferably started at lower temperatures and then continued at higher temperatures of the given temperature range. The reaction may be carried out without solvents or preferably with suitable aprotic solvents, more preferably halogenated hydrocarbons, as for example $CH_3Cl$, $CH_2Cl_2$ or $CHCl_3$.

The sulfonyl derivate of the formula B is treated with an amine $NHR^5$, wherein $R^5$ is defined as hereinbefore, to yield the sulfonamide derivate of the formula C. Preferred reaction temperatures are in the range of −20° C. to +40° C., whereby the reaction is preferably started at lower temperatures and then continued at higher temperatures of the given temperature range. Preferred solvents are ethers or alcohols, as for example tetrahydrofuran, methanol, ethanol or propanol.

The sulfonamide derivative C is carboxylated at the methyl substituent. An advantageous carboxylation method employs butyllithium (BuLi) and carbondioxide. The resulting carboxy-compound D is cyclodehydrated to give a dihydro-thiazine-3-one-1,1-dioxide of the formula E. Upon treatment with an optionally substituted phenyl isocyanate of the formula F1, in dimethylsulfoxide (DMSO) in the presence of triethylamine, the compound E is converted to the final product of the formula G1. This reaction is preferably carried out in a temperature range between 10° C. and 50° C. Instead of the tertiary amine base sodium hydride (NaH) may be used whereby the dihydro-thiazine-3-one-1, 1-dioxide of the formula E is reacted with NaH in tetrahydrofuran and then the optionally substituted phenyl isocyanate of the formula F1 is added to yield the final product of the formula G1. Suitable reaction temperatures are in the range of −20° C. and +40° C.

Reaction scheme 1b:

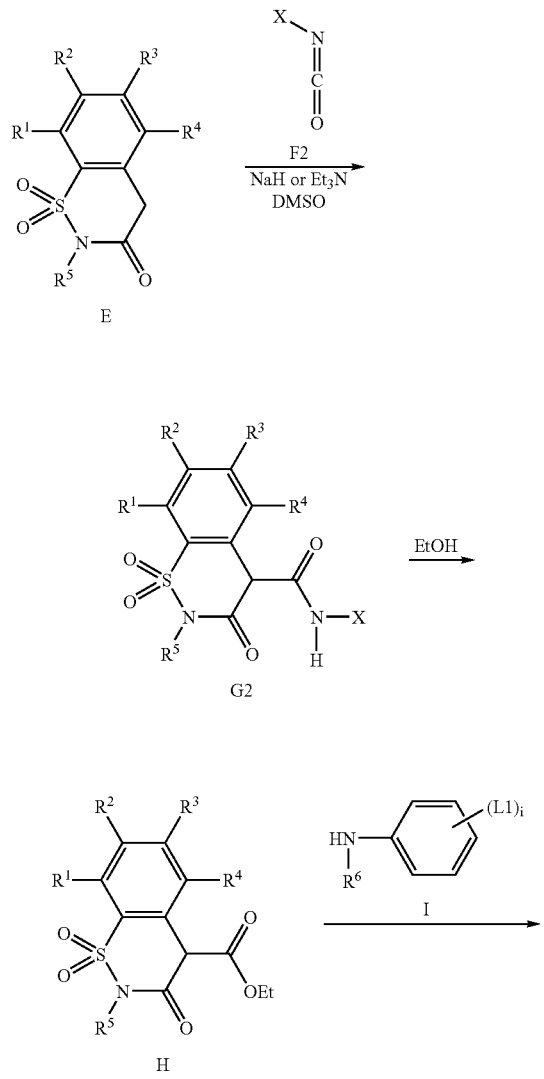

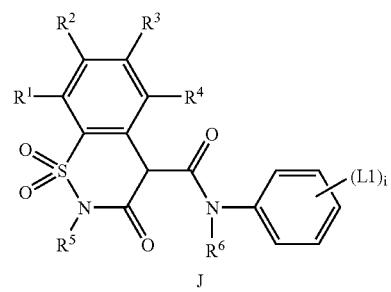

Alternatively, according to the reaction scheme 1b the intermediate product of the formual E is reacted with an isocyanate compound of the formula F2 in the presence of triethylamine or the intermediate product of the formula E is reacted with sodium hydride and afterwards with a isocyanate compound of the formula F2 to yield the amide of the formula G2. In the above formula F2 X represents an optionally substituted alkyl or aryl residue, for example n-butyl. Preferred reaction conditions are given in the description of the reaction scheme 1a.

In order to insert the desired anilide, the amide of the formula G2 is first converted to the corresponding ethyl ester H via ethanolysis, for example, by refluxing in ethanol. The reaction of the ester H with the desired anilide of the formula I yields the product of the formula J. Advantageous reaction conditions, including solvents of the above described steps from the carboxylation to the final reaction with the anilide are described in the literature, for example by Lombardino et al., J. Med. Chem. 1971, 14, 973-977.

Further synthesis methods of the compounds according to this invention are described in the experimental section.

The method of the present invention relates to the treatment or prevention of a disease or condition in a mammal characterized by an increased level of one or more amyloid β peptide isoforms, e.g., as soluble peptides as well as in the form of beta-amyloid plaques, in particular by a pathological form of amyloid β peptide or fibrillar Aβ isoforms, such as Aβ$_{42}$, and therefore the present invention allows for helping to prevent or delay the onset of such a disease or condition.

Furthermore the method of the present invention relates to the treatment or prevention of a disease or condition in a mammal characterized by a changed ratio of levels of Aβ isoforms, in particular by a changed ratio of a level of Aβ$_{40}$ to Aβ$_{42}$, and therefore the present invention allows for helping to prevent or delay the onset of such a disease or condition. The term "changed ratio" means that the ratio of an individual who is diagnosed to have the disease or condition is measurably different from the ratio of an individual who is diagnosed not to have the disease or condition. For example in patients diagnosed with sporadic Alzheimer disease the ratio of a level of Aβ$_{40}$ to Aβ$_{42}$ is decreased, i.e. the level of the Aβ$_{42}$ isoform is more elevated than the level of the Aβ$_{40}$ isoform, compared with an individual not affected by Alzheimers disease. As a further example, in a human not affected by Alzheimer's disease the ratio of the Aβ$_{40}$-level to the Aβ$_{42}$-level is about 10 to 1 whereas in an individual affected by AD, in particular AD caused by PS1 mutation, the ratio is shifted to about 3 to 1 or even 1 to 1 or even lower.

For example, the methods and therefore the compounds of the invention are useful for treating Alzheimer's disease, for helping to prevent or delay the onset of Alzheimer's disease, for treating patients with MCI (mild cognitive impairment) and preventing or delaying the onset of Alzheimer's disease in those who would progress from MCI to AD, for treating Down's syndrome, for treating humans who have Hereditary Cerebral Hemorrhage with Amyloidosis of the Dutch-Type, for treating cerebral amyloid angiopathy and preventing its potential consequences, i.e., single and recurrent lobar hemorrhages, for treating other degenerative dementias, including dementias of mixed vascular and degenerative origin, dementia associated with Parkinson's disease, dementia associated with progressive supranuclear palsy, dementia associated with cortical basal degeneration, and diffuse Lewy body type Alzheimer's disease. The methods, compounds and compositions of the invention are particularly useful for treating or preventing Alzheimer's disease. When treating or preventing these diseases, the compounds of the invention can either be used individually or in combination, as is best for the patient.

As used herein, the term "treatment" means that the compounds of the invention can be used in humans with at least a tentative diagnosis of disease. The compounds of the invention will delay, slow, or reverse the progression of the disease thereby giving the individual a more useful life span.

The term "prevention" means that the compounds of the present invention are useful when administered to a patient who has not been diagnosed as possibly having the disease at the time of administration, but who would normally be expected to develop the disease or be at increased risk for the disease. The compounds of the invention will slow the development of disease symptoms, delay the onset of the disease, or prevent the individual from developing the disease at all.

Prevention also includes administration of the compounds of the invention to those individuals thought to be predisposed to the disease due to age, familial history, genetic or chromosomal abnormalities, and/or due to the presence of one or more biological markers for the disease, such as a known genetic mutation of APP or APP cleavage products in brain tissues or fluids.

The compounds of the invention are administered in a therapeutically effective amount. The therapeutically effective amount will vary depending on the particular compound used and the route of administration, as is known to those skilled in the art.

The compounds of the invention can be administered orally, parenterally, (IV, IM, depo-IM, SQ, and depo SQ), sublingually, intranasally, inhalative, intrathecally, topically, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as tablets, capsules, or elixirs for oral administration or in sterile solutions or suspensions for parenteral administration or aerosols for inhalative administration. Typically the compounds described above are formulated into pharmaceutical compositions using techniques and procedures well known in the art.

About 1 to 2000 mg, in particular 1 to 500 mg of a compound or mixture of compounds of the invention or a physiologically acceptable salt thereof is admixed with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 1 to about 1000 mg, more preferably about 1 to about 200 mg of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

Pharmaceutical acceptable carriers or diluents suitable for administration of the compounds provided herein include any such carriers or diluents known to those skilled in the art to be suitable for the particular mode of administration. In addition, the active materials can also be mixed with other active materials that do not impair the desired action, or with materials that supplement the desired action, or have another action.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance, and bioavailability.

The compounds may be formulated as the sole pharmaceutically active ingredient in the composition or may be combined with one or more different active ingredients.

The concentration of the compound is effective for delivery of an amount upon administration that lessens or ameliorates at least one symptom of the disorder for which the compound is administered. Typically, the compositions are formulated for single dosage administration.

The compounds and compositions of the invention can be enclosed in multiple or single dose containers. The compounds and compositions according to the invention can be provided in kits, for example, including component parts that can be assembled for use. For example, a compound according to this invention in lyophilized form and a suitable diluent may be provided as separated components for combination prior to use. A kit may include a compound according to this invention and a second therapeutic agent for co-administration. The compound and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampules, vials and the like for parenteral administration; and patches, medipads, creams, and the like for topical administration, and optionally pre-filled inhalators for inhalative administration.

The concentration of active compound in the drug composition will depend on absorption, inactivation, and excretion rates of the active compound, the dosage schedule, and amount administered as well as other factors known to those of skill in the art.

It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed method and composition.

Oral compositions will generally include an inert diluent or an edible carrier and may be compressed into tablets or enclosed in capsules. For the purpose of oral therapeutic administration, the active compound or compounds can be incorporated with excipients and used in the form of tablets, capsules, lozenges, or troches.

Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Methods for preparation of such formulations are known to those skilled in the art.

The oral dosage forms are administered to the patient 1, 2, 3, or 4 times daily. It is preferred that the compounds of the invention be administered either three or fewer times, more preferably once or twice daily. Hence, it is preferred that the compounds of the invention be administered in oral dosage form.

An administered amount therapeutically effective, especially when administered orally, to modulate gamma-secretase activity, in particular such as to lower the level of $A\beta_{42}$ or to increase the ratio of the $A\beta_{40}$-level to the $A\beta_{42}$-level;

to inhibit A beta production, in particular to inhibit $A\beta_{42}$-production;

to inhibit A beta deposition, in particular deposition of fibrillar $A\beta$ isoforms, e.g. of $A\beta_{42}$; or to treat or prevent a neurodegenerative disorder, in particular AD is preferably from about 0.1 mg/day to about 2000 mg/day, more preferably 0.1 mg/day to about 200 mg/day, in particular 0.5 mg/day to about 50 mg/day. It is understood that while a patient may be started at one dose, that dose may be varied over time as the patient's condition changes.

Given a particular compound of the invention and a desired dosage form, one skilled in the art would know how to prepare and administer the appropriate dosage form.

It should be apparent to one skilled in the art that the exact dosage and frequency of administration will depend on the particular compounds of the invention administered, the particular condition being treated, the severity of the condition being treated, the age, weight, general physical condition of the particular patient, and other medication the individual may be taking as is well known to administering physicians who are skilled in this art.

Without being bound to any theory, there are indications suggesting that the compounds of the invention are suitable to modulate cleavage of APP at the gamma (γ) secretase cleavage site, or a mutant thereof, or at a corresponding site of a different isoform, such as APP751 or APP770, or a mutant thereof (sometimes (referred to as the "gamma secretase site"). While not wishing to be bound to a particular theory, modulation of γ-secretase activity is thought to inhibit the production of toxic beta amyloid peptide (Aβ beta). Inhibitory activity is demonstrated in one of a variety of inhibition assays, whereby cleavage of an APP substrate in the presence of a γ-secretase enzyme is analyzed in the presence of the inhibitory compound, under conditions normally sufficient to result in cleavage at the γ-secretase cleavage site. Reduction of APP cleavage at the γ-secretase cleavage site compared with an untreated or inactive control is correlated with inhibitory activity. Assay systems that can be used to demonstrate efficacy of the compounds of the invention are known, for example Aβ specific ELISA to quantify Aβ-levels are described by Eriksen et al., 2003 and Weggen et al., 2001.

The enzymatic activity of γ-secretase and the production of A beta can be analyzed in vitro or in vivo, using natural, mutated, and/or synthetic APP substrates, natural, mutated, and/or recombinant enzyme, and the test compound. The analysis may involve primary or secondary cells expressing native, mutant, and/or recombinant APP and enzyme, animal models expressing native or mutated APP and enzyme, or may utilize transgenic and non-transgenic animal models expressing the substrate and enzyme. Detection of enzymatic activity can be done by analysis of one or more of the cleavage products, for example, by an in vitro assay, in particular an Aβ secretion assay, fluorometric or chromogenic assay, HPLC, or other means of detection. Inhibitory compounds are determined as those having the ability to decrease the amount of gamma-secretase cleavage product produced in comparison to a control, where gamma-secretase mediated cleavage in the reaction system is observed and measured in the absence of inhibitory compounds.

Preferably the assay is carried out as follows:

Cell culture and drug treatment: U373 astrocytoma cells expressing human wtAPP695 were used for screening compounds. Cells were cultured in 96 well plates in DMEM medium, additionally supplemented with 10% FCS and 1% glutamine, until they have grown to a confluent cell layer. The cells were then incubated for 17 hours in the presence of the various NSAID-analogues in DMEM medium. Afterwards, 100 µl of the supernatant had been removed and measured with the ELISA as described below to determine the $A\beta_{42}$ peptide concentrations. The cells were washed, incubated again for 4 hours with the compound, before measuring the $A\beta_{40}$ levels. AlamarBlue assays (Serotec, Oxford, United Kingdom) were conducted to determine cytotoxicity.

Sandwich ELISA for Aβ:

Monoclonal 6E10 against $A\beta_{1-17}$ (Signet Laboratories, Inc., Dedham, Mass., USA) was used to capture $A\beta_{40}$; SGY 3160 against $A\beta_{1-16}$ (Mayo Medical Ventures, Rochester, Minn., USA) to capture $A\beta_{42}$. Both antibodies were diluted in PBS at a concentration of 8 µg/ml to coat a 96 well plate. Blocking was completed with 1% Block ACE (blocking reagent) (Dainippon Seiyaku, Asaka, Japan) in PBS for 2 hrs. The plates were then washed with PBST and the cell supernatants, diluted 1:1.5 in EC buffer (0.1 M $NaH_2PO_4$, 0.1 M $Na_2HPO_4$, 2 mM EDTA, 0.4 M NaCl, 0.2% BSA, 0.05% CHAPS, 0.4% Block ACE, 0.05% $NaN_3$ pH 7.0) have been added into the wells, before the plates were stored at 4° C. over night. Detector antibodies (alkaline phosphatase-coupled ROβ40 and ROβ42 against $A\beta_{40}$ and $A\beta_{42}$, respectively) were loaded onto the wells at 0.1 µg/ml in ACE Block for 2 hrs. The reporter system used was the Tropix ELISA-Light chemiluminescent detection system (Applied Biosystems (Tropix), Bedford, Mass., USA).

In addition mass spectrometric methods can be employed for the determination of levels of isoforms of Aβ (see e.g. Eriksen et al., 2003; Weggen et al., 2003; Weggen et al., 2001).

Various animal models can be used to analyze gamma-secretase activity and/or processing of APP to release A beta, as described above. For example, transgenic animals over-expressing APP substrate can be used to demonstrate inhibitory activity of the compounds of the invention. Certain transgenic animal models have been described, for example, in U.S. Pat. Nos. 5,877,399; 5,612,486; 5,387,742; 5,720,936; 5,850,003; 5,877,015 and 5,811,633, and in Games et. al., 1995, Nature 373: 523. Preferred are animals that exhibit characteristics associated with the pathophysiology of AD. Administration of the compound inhibitors of the invention to the transgenic mice described herein provides an alternative method for demonstrating the inhibitory activity of the compounds. Administration of the compounds in a pharmaceutically effective carrier and via an administrative route that reaches the target tissue in an appropriate therapeutic amount is also preferred.

Unless defined otherwise, all scientific and technical terms used herein have the same meaning as commonly understood by one of skill in the art to which this invention belongs. All patents and publications referred to herein are hereby incorporated by reference for all purposes. The definitions and explanations below are for the terms as used throughout this entire document including both the specification and the claims.

Without further elaboration, it is believed that one skilled in the art can, using the preceding description, practice the present invention to its fullest extent.

The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

All temperatures are in degrees Celsius.

EXAMPLE 1

3,4,6,7,8,9-Hexahydro-2-methyl-3-oxo-2H-naphtho[2,3-e]-1,2-thiazine-4-carboxanilide 1,1-dioxide

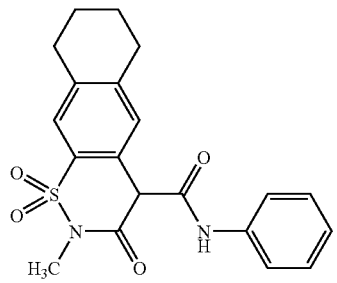

A solution of 5 g (19 mmol) 3,4,6,7,8,9-hexahydro-2-methyl-3-oxo-2H-naphtho[2,3-e]-1,2-thiazine 1,1-dioxide in 100 mL tetrahydrofuran was added to a suspension of 0.7 g (29 mmol) sodium hydride in 50 mL tetrahydrofuran at −5° C. under $N_2$. After termination of the hydrogen formation 5.7 g (48 mmol) phenylisocyanate dissolved in 50 mL tetrahydrofuran were added at −5° C. After stirring at room temperature (approx. 20° C.) the resulting mixture was quenched with ice/water and by addition of dilute HCl and then extracted with $CH_2Cl_2$ (2 times). The combined $CH_2Cl_2$ extracts were washed, dried and concentrated to give 6 g crude product. This material was recrystallized from ethanol to give 3.6 g 3,4,6,7,8,9-hexahydro-2-methyl-3-oxo-2H-naphtho[2,3-e]-1,2-thiazine-4-carboxanilide 1,1-dioxide.

Yield: 54%

Melting point: 203-204° C.

Structure was confirmed by elementary analysis ($C_{20}H_{20}N_2O_4S$: C,H,N,S) and IR- and NMR-spectroscopy.

Preparation of the Starting Material:

To a solution of 124 g (0.84 mol) 2-methyl-5,6,7,8-tetrahydro-naphthalene in 600 mL $CHCl_3$ 294 g (2.52 mol) chlorosulfonic acid at 0° C. were added. After 2 hrs at room temperature the solution was slowly poured onto ice. The organic phase was washed, dried and concentrated to give 231.4 g 2-methyl-5,6,7,8-tetrahydro-naphthalene-2-sulfonic acid chloride used directly for the subsequent reaction.

231.4 g (0.84 mol) of the above sulfonic acid chloride were added to a solution of 57.5 g (1.8 mol) methylamine in 1.2 L ethanol at +5° C. followed by 192 g (1.9 mol) triethylamine. The mixture was stirred at +5° C. for 2 hrs and allowed to come to room temperature over 2 hrs. The reaction mixture was concentrated and the residue taken up in ether, washed, dried, and concentrated. Recrystallization of the residue from cyclohexane gave 136.1 g 2-methyl-5,6,7,8-tetrahydro-naphthalene-3-sulfonic acid methylamide.

100 mL of a 1.5 molare (150 mmol) butyl lithium in hexane were added to a solution of 18 g (75 mmol) 2-methyl-5,6,7,8-tetrahydro-naphthalene-3-sulfonic acid methylamide in 200 mL tetrahydrofuran at −20° C. The resulting mixture was allowed to come to room temperature and was poured onto a mixture of ether and solid $CO_2$. After addition of water the resulting mixture was acidified with dilute HCl and then extracted with $CH_2Cl_2$. The $CH_2Cl_2$ solution was washed, dried and concentrated. Recrystallization from ether/petroleum ether gave 15.8 g 3-(N-methyl-sulfamoyl)-5,6,7,8-tetrahydro-naphthalene-2-acetic acid (melting point: 153-155° C.).

This naphthalene-2-acetic acid (14.7 g, 52 mmol) was refluxed 12 hrs in 250 mL xylene with the addition of 0.2 g p-toluene-sulfonic acid. The reaction mixture was cooled, filtered, washed with water and concentrated. 13.5 g crude product were yielded.

EXAMPLE 2

3,4,6,7,8,9-Hexahydro-2-methyl-3-oxo-2H-naphtho[2,3-e]-1,2-thiazine-4-(4-methyl)carboxanilide 1,1-dioxide

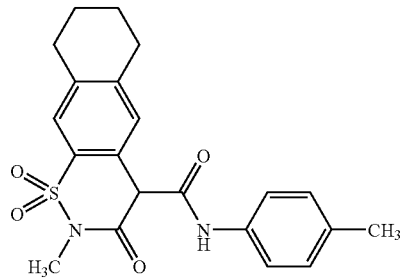

A solution of 2 g (7,5 mmol) 3,4,6,7,8,9-hexahydro-2-methyl-3-oxo-2H-naphtho[2,3-e]-1,2-thiazine 1,1-dioxide in 100 mL tetrahydrofuran was added to a suspension of 0.27 g (11.3 mmol) sodium hydride in 50 mL tetrahydrofuran was added at −5° C. under $N_2$. After termination of the hydrogen formation 2.5 g (18.8 mmol) p-methyl-phenylisocyanate dissolved in 50 mL tetrahdrofuran were added at −5° C. After stirring at room temperature the resulting mixture was quenched with ice/water and by addition of dilute HCl and then extracted with $CH_2Cl_2$ (2 times). The combined $CH_2Cl_2$ extracts were washed, dried and concentrated to give the crude product. This material was recrystallized from ethanol to give 1.6 g 3,4,6,7,8,9-hexahydro-2-methyl-3-oxo-2H-naphtho[2,3-e]-1,2-thiazine-4-(4-methyl)carboxanilide 1,1-dioxide.

Yield: 54%

Melting point: 207-209° C.

Structure was confirmed by elementary analysis ($C_{21}H_{22}N_2O_4S$: C,H,N,S) and IR- and NMR-spectroscopy.

EXAMPLE 3

3,4,6,7,8,9-Hexahydro-2-methyl-3-oxo-2H-naphtho[2,3-e]-1,2-thiazine-4-(4-fluor)carboxanilide 1,1-dioxide

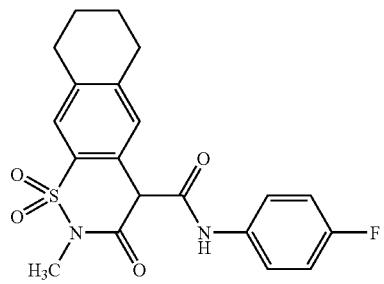

0.76 g (7.5 mmol) triethylamin were added to a solution of 2 g (7.5 mmol) 3,4,6,7,8,9-hexahydro-2-methyl-3-oxo-2H-naphtho[2,3-e]-1,2-thiazine 1,1-dioxide and 1.03 g (7.5 mmol) p-fluor-phenylisocyanate dissolved in 50 mL DMSO (dimethyl sulfoxide) at room temperature. After stirring for 1 hr the resulting mixture was quenched with dilute HCl in an ice bath and then extracted with ether (2 times). The combined ether extracts were washed, dried and concentrated to give 2.3 g crude product. This material was recrystallized from ethanol to give 1.7 g 3,4,6,7,8,9-hexahydro-2-methyl-3-oxo-2H-naphtho[2,3-e]-1,2-thiazine-4-(4-fluor)carboxanilide 1,1-dioxide.

Yield: 56%

Melting point: 202-203° C.

Structure was confirmed by elementary analysis ($C_{20}H_{19}FN_2O_4S$: C,H,N,S) and IR- and NMR-spectroscopy.

EXAMPLE 4

3,4,6,7,8,9-Hexahydro-2-methyl-3-oxo-2H-naphtho[2,3-e]-1,2-thiazine-4-(4-chloro)carboxanilide 1,1-dioxide

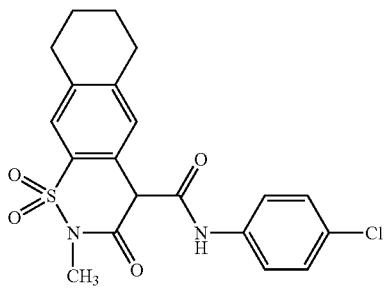

Prepared from 3,4,6,7,8,9-hexahydro-2-methyl-3-oxo-2H-naphtho[2,3-e]-1,2-thiazine 1,1-dioxide and p-chloro-phenylisocyanate analogous to example 1 and recrystallized from ethanol.

Yield: 56%

Melting point: 203-205° C.

Structure was confirmed by elementary analysis ($C_{20}H_{19}ClN_2O_4S$: C,H,N,S) and UV-, IR- and NMR-spectroscopy.

EXAMPLE 5

3,4,6,7,8,9-Hexahydro-2-methyl-3-oxo-2H-naphtho[2,3-e]-1,2-thiazine-4-(2,5-dichloro)carboxanilide 1,1-dioxide

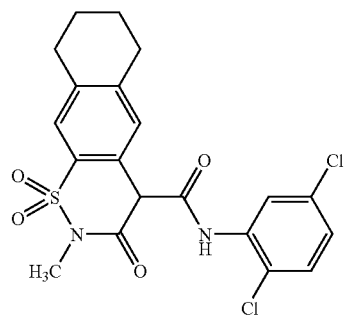

Prepared from 3,4,6,7,8,9-hexahydro-2-methyl-3-oxo-2H-naphtho[2,3-e]-1,2-thiazine 1,1-dioxide and 2,5-dichloro-phenylisocyanate analogous to example 3 and recrystallization from ethylacetate Yield: 59%

Melting point: 178-180° C.

Structure was confirmed by elementary analysis ($C_{20}H_{18}Cl_2N_2O_4S$: C,H,N,S) and UV-, IR- and NMR-spectroscopy.

EXAMPLE 6

3,4,6,7,8,9-Hexahydro-2-methyl-3-oxo-2H-naphtho[2,3-e]-1,2-thiazine-4-(3,4-dichloro)carboxanilide 1,1-dioxide

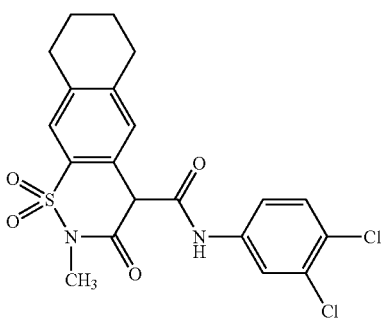

Prepared from 3,4,6,7,8,9-hexahydro-2-methyl-3-oxo-2H-naphtho[2,3-e]-1,2-thiazine 1,1-dioxide and 3,4-dichloro-phenylisocyanate analogous to example 1 and recrystallization from ethylacetate.

Yield: 38%

Melting point: 226-228° C.

Structure was confirmed by elementary analysis ($C_{20}H_{18}Cl_2N_2O_4S$: C,H,N,S) and UV-, IR-, and NMR-spectroscopy.

EXAMPLE 7

3,4,6,7,8,9-Hexahydro-2-methyl-3-oxo-2H-naphtho[2,3-e]-1,2-thiazine-4-(3-chloro-4-methyl)carboxanilide 1,1-dioxide

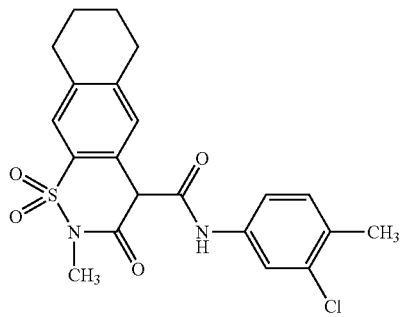

Prepared from 3,4,6,7,8,9-hexahydro-2-methyl-3-oxo-2H-naphtho[2,3-e]-1,2-thiazine 1,1-dioxide and 3-chloro-4-methyl-phenylisocyanate analogous to example 3 and recrystallization from ethanol.

Yield: 76%

Melting point: 207-209° C.

Structure was confirmed by elementary analysis ($C_{21}H_{21}ClN_2O_4S$: C,H,N,S) and UV-, IR- and NMR-spectroscopy.

EXAMPLE 8

3,4,6,7,8,9-Hexahydro-2-methyl-3-oxo-2H-naphtho[2,3-e]-1,2-thiazine-4-(4-bromo)carboxanilide 1,1-dioxide

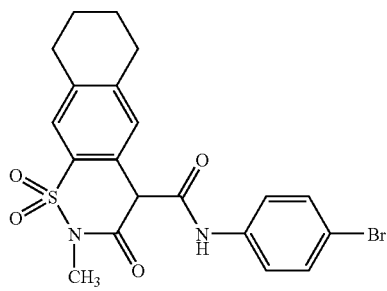

Prepared from 3,4,6,7,8,9-hexahydro-2-methyl-3-oxo-2H-naphtho[2,3-e]-1,2-thiazine 1,1-dioxide and 4-bromo-phenylisocyanate analogous to example 1 and recrystallization from ethanol.

Yield: 33%

Melting point: 198-200° C.

Structure was confirmed by elementary analysis ($C_{20}H_{19}BrN_2O_4S$: C,H,N,S) and UV- and IR-spectroscopy.

EXAMPLE 9

3,4,6,7,8,9-Hexahydro-2-methyl-3-oxo-2H-naphtho[2,3-e]-1,2-thiazine-4-(2-chloro)carboxanilide 1,1-dioxide

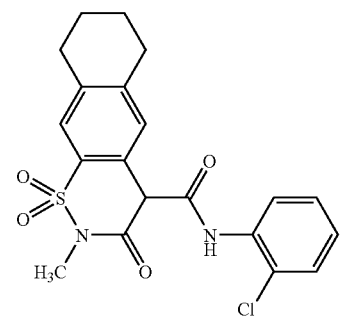

Prepared from 3,4,6,7,8,9-hexahydro-2-methyl-3-oxo-2H-naphtho[2,3-e]-1,2-thiazine 1,1-dioxide and 2-chloro-phenylisocyanate analogous to example 3 and recrystallization from ethanol.

Yield: 42%

Melting point: 172-173° C.

Structure was confirmed by elementary analysis ($C_{20}H_{19}ClN_2O_4S$: C,H,N,S).

EXAMPLE 10

3,4,6,7,8,9-Hexahydro-2-methyl-3-oxo-2H-naphtho[2,3-e]-1,2-thiazine-4-(3-chloro)carboxanilide 1,1-dioxide

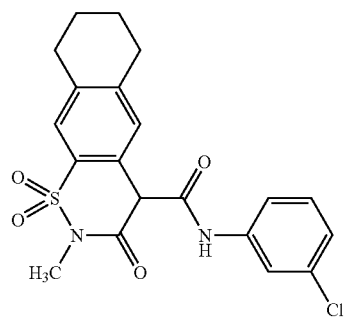

Prepared from 3,4,6,7,8,9-hexahydro-2-methyl-3-oxo-2H-naphtho[2,3-e]-1,2-thiazine 1,1-dioxide and 2-chloro-phenylisocyanate analogous to example 3 and recrystallization from ethanol.

Yield: 57%

Melting point: 182-184° C.

Structure was confirmed by elementary analysis ($C_{20}H_{19}ClN_2O_4S$: C,H,N,S) and UV-, IR- and NMR-spectroscopy.

EXAMPLE 11

3,4,6,7,8,9-Hexahydro-2-methyl-3-oxo-2H-naphtho[2,3-e]-1,2-thiazine-4-(4-nitro)carboxanilide 1,1-dioxide

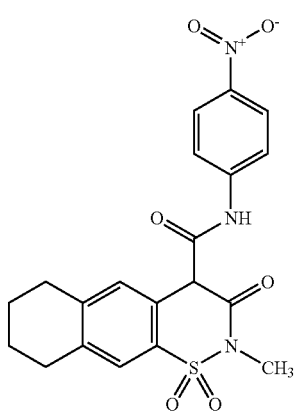

Prepared from 3,4,6,7,8,9-hexahydro-2-methyl-3-oxo-2H-naphtho[2,3-e]-1,2-thiazine 1,1-dioxide and 4-nitrophenylisocyanate analogous to example 1 and recrystallization from ethanol.

Yield: 68%

Melting point: 205-207° C.

Structure was confirmed by elementary analysis ($C_{20}H_{19}N_3O_6S$: C,H,N,S) and IR- and NMR-spectroscopy.

EXAMPLE 12

3,4,6,7,8,9-Hexahydro-2-methyl-3-oxo-2H-naphtho[2,3-e]-1,2-thiazine-4-(4-chloro)carboxanilide 1,1-dioxide

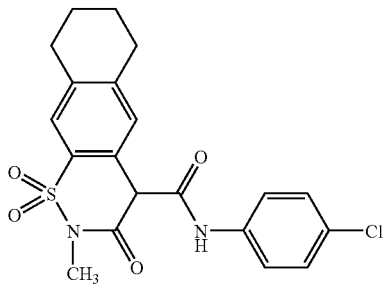

Example 12 describes an alternative synthesis method compared to example 4.

A mixture of 3,4,6,7,8,9-hexahydro-2-methyl-3-oxo-2H-naphtho[2,3-e]-1,2-thiazine-4-carboxylic acid ethylester 1,1-dioxide and 4-chloro-aniline in 75 mL toluene was refluxed under $N_2$ for 2 hrs. Ethanol was collected in a Dean-Stark trap. The remaining toluene was removed from the solution on a rotary evaporator. The residue was treated with methylenechloride and recrystallized from ethanol.

Yield: 87%

Melting point: 203-205° C.

Structure was confirmed by elementary analysis ($C_{20}H_{19}ClN_2O_4S$: C,H,N,S) and UV-, IR- and NMR-spectroscopy.

Preparation of the Starting Material:

0.76 g (7.5 mmol) triethylamin were added to a solution of 2 g (7.5 mmol) 3,4,6,7,8,9-hexahydro-2-methyl-3-oxo-2H-naphtho[2,3-e]-1,2-thiazine 1,1-dioxide and 0.765 g (7.5 mmol) n-butyl-isocyanate dissolved in 50 mL DMSO at room temperature. After stirring for 1 hr the resulting mixture was quenched with dilute HCl in an ice bath and then extracted with ether (2 times). The combined ether extracts were washed, dried and concentrated to give 2.3 g crude product. This material was recrystallized from ethanol to give 2.1 g 3,4,6,7,8,9-hexahydro-2-methyl-3-oxo-2H-naphtho[2,3-e]-1,2-thiazine-4-(n-butyl)carboxamide 1,1-dioxide.

A solution of 2.1 g (6.0 mmol) 3,4,6,7,8,9-hexahydro-2-methyl-3-oxo-2H-naphtho[2,3-e]-1,2-thiazine-4-(n-butyl) carboxamide 1,1-dioxide in 100 mL ethanol was refluxed overnight under $N_2$. Solvent was removed on a rotary evaporator, the residue dissolved in ether. After washing, drying and concentrating the crude product was triturated with petroleum ether/methylenechloride to give 2.0 g 3,4,6,7,8,9-hexahydro-2-methyl-3-oxo-2H-naphtho[2,3-e]-1,2-thiazine-4-carboxylic acid ethylester 1,1-dioxide.

EXAMPLE 13

3,4,7,8,9,10-Hexahydro-2-methyl-3-oxo-2H-naphtho[2,1-e]-1,2-thiazine-4-(4-chloro)carboxanilide 1,1-dioxide

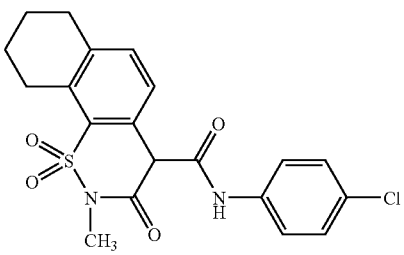

A solution of 500 mg (1.9 mmol) 3,4,7,8,9,10-hexahydro-2-methyl-3-oxo-2H-naphtho[2,3-e]-1,2-thiazine 1,1-dioxide in 100 mL tetrahydrofuran was added to a suspension of 68 mg (2.8 mmol) sodium hydride in 10 mL tetrahydrofuran at −5° C. under $N_2$. After termination of the hydrogen formation 720 mg (4.7 mmol) p-chlorophenylisocyanate dissolved in 5 mL tetrahydrofuran were added at −5° C. After stirring at room temperature the resulting mixture was quenched with ice/water and by addition of dilute HCl and then extracted with ether (2 times). The combined ether extracts were washed, dried and concentrated to give crude product. This material was filtered on a silica gel column using $CHCl_3$ with 2% ethanol as eluant. Recrystallization of the eluated main fraction from cyclohexane/$CHCl_3$ gave 300 mg 3,4,7,8,9,10-hexahydro-2-methyl-3-oxo-2H-naphtho[2,1-e]-1,2-thiazine-4-(4-chloro)carboxanilide 1,1-dioxide.

Yield: 38%

Melting point: 106-108° C.

Structure was confirmed by elementary analysis ($C_{20}H_{19}ClN_2O_4S$: C,H,N,S) and IR- and NMR-spectroscopy.

Preparation of the Starting Material:

A solution of 20 g (0.137 mol) 2-methyl-5,6,7,8-tetrahydro-naphthalene in 200 mL $CHCl_3$ was added to 48 g (0.412 mol) chlorosulfonic acid at 0° C. After 2 hrs at room temperature the solution was slowly poured onto ice. The organic phase was washed, dried and concentrated to give 32 g 2-methyl-5,6,7,8-tetrahydro-naphthalene-sulfonic acid chloride used directly for the subsequent reaction.

32 g (0.137 mol) of the above sulfonic acid chloride were added to a solution of 10 g (0.3 mol) methylamine in 150 mL ethanol at +5° C. The mixture was stirred at +5° C. for 2 hrs and allowed to come to room temperature over 2 hrs. The reaction mixture was concentrated and the residue taken up in ether, washed, dried, and concentrated. After separation of the major reaction product (3-sulfonamide) by crystallisation from cyclohexane the resulting solution was concentrated and filtered on silica gel using cyclohexane/ethylacetate (4:1) as eluant. Recrystallization of the major fraction gave 4.5 g 2-methyl-5,6,7,8-tetrahydro-naphthaline-1-sulfonic acid methylamide.

18.3 mL of a 1.5 molare (40 mmol) butyl lithium in hexane were added to a solution of 4.5 g (19 mmol) sulfonic acid methylamide in 100 mL tetrahydrofuran at −20° C. The resulting mixture was allowed to come to room temperature and was poured onto a mixture of ether and solid $CO_2$. After addition of water the resulting mixture acidified with dilute HCl and the extracted with $CH_2Cl_2$. The $CH_2Cl_2$ solution was washed, dried and concentrated: 3.8 g crude 1-(N-methyl-sulfamoyl)-5,6,7,8-tetrahydro-naphthalene-2-acetic acid was yielded.

This naphthalene-2-acetic acid (3.8 g) was refluxed 12 hrs in 250 mL xylene with the addition of 0.2 g p-toluene-sulfonic acid. The reaction mixture was cooled, filtered, washed with water and concentrated. Filtration on a silica gel column and recrystallization from cyclohexane gave 0.4 g 3,4,7,8,9,10-hexahydro-2-methyl-3-oxo-2H-naphtho[2,1-e]-1,2-thiazine 1,1-dioxide with a melting point: 90-92° C. The structure was confirmed by elementary analysis and IR-, UV- and NMR-spectroscopy.

EXAMPLE 14

6-Chloro-3,4-dihydro-2-(4-fluorobenzyl)-3-oxo-2H-1,2-benzothiazine-4-(2-trifluoromethyl)carboxanilide 1,1-dioxide

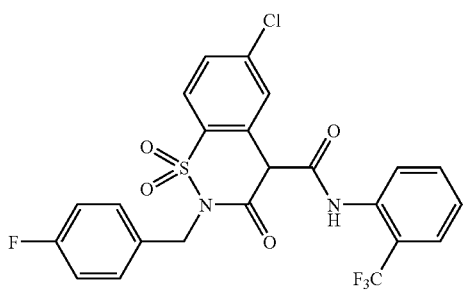

At room temperature 77 mg (0.76 mmol) triethylamin were added to a mixture of 250 mg (0.74 mmol) 6-chloro-3,4-dihydro-2-(4-fluorobenzyl)-3-oxo-2H-1,2-benzothiazine 1,1-dioxide and 142 mg (0.76 mmol) o-trifuoromethyl-phenylisocyanate dissolved in 3 mL DMSO. After stirring for 2.5 hrs the resulting mixture was quenched with dilute HCl in an ice bath and then extracted with methylenechloride (2 times). The combined extracts were washed, dried and concentrated to give 380 mg crude product. This material was recrystallized from methylenechloride/hexane to give 263 mg 6-chloro-3,4-dihydro-2-(4-fluorobenzyl)-3-oxo-2H-1,2-benzothiazine-4-(2-trifuoromethyl)carboxanilide 1,1-dioxide.

Yield: 68%

Melting point: 198-199° C.

Structure was confirmed by elementary analysis ($C_{23}H_{15}F_4ClN_2O_4S$: C,H,N) and mass-spectroscopy.

Preparation of the Starting Material:

25.0 g p-fluorobenzylamine and 15.9 ml triethylamine were added to a solution of 12.4 g (55.6 mmol) 4-chloro-2-methyl-phenylsulfonic acid chloride in 150 ml tetrahydrofuran at 5° C. The mixture was stirred at +5° C. for 20 mins and 3.5 hrs at room temperature. The reaction mixture was poured into water and extracted into methylenechloride, washed, dried, and concentrated to give 16.4 g crude material.

60 ml of a 2.5 molare butyl lithium solution in hexane were added to a solution of 16.4 g (52.4 mmol) 4-chloro-2-methyl-benzosulfon-(4-fluorobenzyl)amide in 225 ml tetrahydrofuran at −5° C. The resulting mixture was allowed to come to room temperature and was poured onto a mixture of ether and solid $CO_2$. After addition of water the resulting mixture acidified with dilute HCl and then extracted with $CH_2Cl_2$. The $CH_2Cl_2$ solution was washed, dried and concentrated. Filtration on a silica gel column gave 11.1 g 5-chloro-1-(N-4-fluorobenzyl-sulfamoyl)-phenyl-acetic acid. This phenyl-acetic acid (2.86 g, 8.8 mmol) was refluxed 12 hrs in 50 mL xylene with the addition of 5 mg p-toluene-sulfonic acid. The reaction mixture was cooled, filtered, washed with water and concentrated. Recrystallization from methylenechloride/hexane gave 1.63 g 6-chloro-3,4-dihydro-2-(4-fluorbenzyl)-3-oxo-2H-1.2-benzothiazine 1.1-dioxide. Melting point 132-133° C. Yield 55%.

EXAMPLE 15

6-Chloro-3,4-dihydro-2-(4-fluorobenzyl)-3-oxo-2H-1,2-benzothiazine-4-(3-trifluoromethyl)carboxanilide 1,1-dioxide

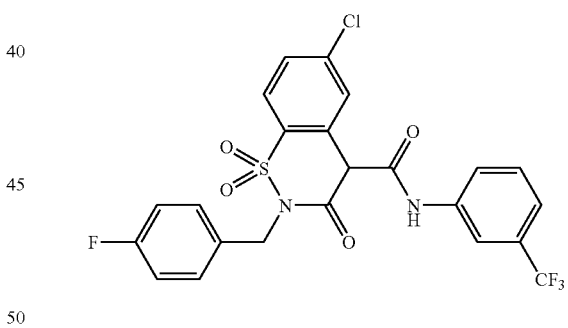

At room temperature 70 mg (0.7 mmol) triethylamin were added to a mixture of 250 mg (0.74 mmol) 6-chloro-3,4-dihydro-2-(4-fluorobenzyl)-3-oxo-2H-1,2-benzothiazine 1,1-dioxide and 130 mg (0.7 mmol) o-trifuoromethyl-phenylisocyanate dissolved in 3 mL DMSO. After stirring for 2.5 hrs the resulting mixture was quenched with dilute HCl in an ice bath and then extracted with methylenechloride (2 times). The combined extracts were washed, dried and concentrated to give 380 mg crude product. This material was recrystallized from methylenechloride/hexane to give 240 mg 6-chloro-3,4-dihydro-2-(4-fluorobenzyl)-3-oxo-2H-1,2-benzothiazine-4-(3-trifluoromethyl)carboxanilide 1,1-dioxide.

Yield: 62%

Melting point: 183-184° C.

Structure was confirmed by elementary analysis ($C_{23}H_{15}F_4ClN_2O_4S$: C,H,N) and mass-spectroscopy.

EXAMPLE 16

6-Chloro-3,4-dihydro-2-(4-fluorobenzyl)-3-oxo-2H-1,2-benzothiazine-4-(3,5-bis(trifluoromethyl))carboxanilide 1,1-dioxide

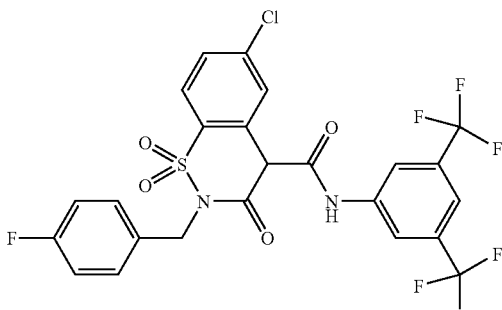

At room temperature 76 mg (0.75 mmol) triethylamin were added to a mixture of 250 mg (0.74 mmol) 6-chloro-3,4-dihydro-2-(4-fluorobenzyl)-3-oxo-2H-1,2-benzothiazine 1,1-dioxide and 192 mg (0.75 mmol) 3,5-bis(trifluoromethyl)-phenylisocyanate dissolved in 3 mL DMSO. After stirring for 2.5 hrs the resulting mixture was quenched with dilute HCl in an ice bath and then extracted with methylenechloride (2 times). The combined extracts were washed, dried and concentrated to give 390 mg crude product. This material was recrystallized from methylenechloride/hexane to give 303 mg 6-chloro-3,4-dihydro-2-(4-fluorobenzyl)-3-oxo-2H-1,2-benzothiazine-4-(3-trifluoromethyl)carboxanilide 1,1-dioxide.

Yield: 69%

Melting point: 233-234° C.

Structure was confirmed by elementary analysis ($C_{23}H_{14}F_4ClN_2O_4S$: C,H,N) and mass-spectroscopy.

EXAMPLE 17

6-Chloro-3,4-dihydro-2-(4-fluorobenzyl)-3-oxo-2H-1,2-benzothiazine-4-(2,4-dibromo)carboxanilide 1,1-dioxide

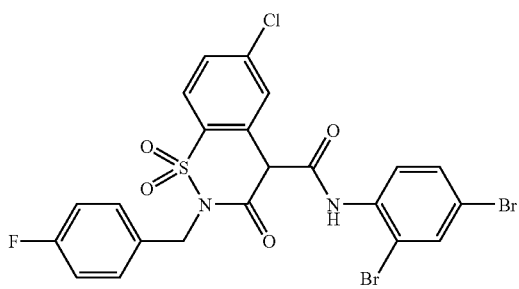

A mixture of 550 mg (1.34 mmol) 6-chloro-3,4-dihydro-2-(4-fluorobenzyl)-3-oxo-2H-1.2-benzothiazine-4-carboxylic acid ethylester 1,1-dioxide and 351 mg 2,4-dibromoaniline in 50 mL toluene was refluxed under $N_2$ for 2 hrs. Ethanol was collected in a Dean-Stark trap. The remaining toluene was removed from the solution on a rotary evaporator. The residue was recrystallized from methylenechloride/hexane to give 484 mg 6-chloro-3,4-dihydro-2-(4-fluorobenzyl)-3-oxo-2H-1,2-benzothiazine-4-(2,4-dibromo)carboxanilide 1,1-dioxide Yield: 62%

Melting point: 222-223° C.

Structure was confirmed by elementary analysis ($C_{22}H_{17}FCl Br_2N_2O_4S$: C,H,N) and NMR- and mass-spectroscopy.

Preparation of the Starting Material:

At room temperature 77 mg (0.76 mmol) triethylamin were added to a mixture of 250 mg (0.74 mmol) 6-chloro-3,4-dihydro-2-(4-fluorobenzyl)-3-oxo-2H-1,2-benzothiazine 1,1-dioxide and 75 mg (0.76 mmol) n-butylisocyanate dissolved in 3 mL DMSO. After stirring for 2.5 hrs the resulting mixture was quenched with dilute HCl in an ice bath and then extracted with methylenechloride (2 times). The combined extracts were washed, dried and concentrated to give 310 mg crude product. This material was recrystallized from methylenechloride/hexane to give 240 mg 6-chloro-3,4-dihydro-2-(4-fluorobenzyl)-3-oxo-2H-1,2-benzothiazine-4-(n-butyl)carboxamide 1,1-dioxide.

A solution of 210 mg 6-chloro-3,4-dihydro-2-(4-fluorbenzyl)-3-oxo-2H-1,2-benzothiazine-4-(n-butyl)carboxamide 1,1-dioxide in 20 mL ethanol was refluxed overnight under $N_2$. The solvent was removed on a rotary evaporator, the residue dissolved in ether. After washing, drying and concentrating the crude product was triturated with petroleum ether/methylenechloride to give 200 mg 6-chloro-3,4-dihydro-2-(4-fluorobenzyl)-3-oxo-2H-1.2-benzothiazine-4-carboxylic acid ethylester 1,1-dioxide.

EXAMPLE 18

3,4-Dihydro-2-methyl-3-oxo-2H-naphtho[2,3-e]-1,2-thiazine-4-carboxanilide 1,1-dioxide

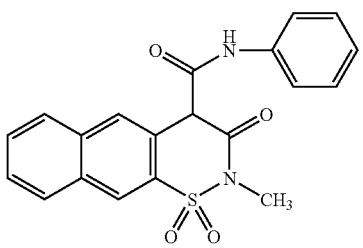

To a solution of 1.3 g (5 mmol) 3,4-dihydro-2-methyl-3-oxo-2H-naphtho[2,3-e]-1,2-thiazine 1,1-dioxide and 0.7 ml (5 mmol) triethylamin dissolved in 10 ml DMSO at room temperature was added 0.6 g (5 mmol) phenylisocyanate. After stirring for 20 hr the resulting mixture was quenched with dilute HCl in an ice bath and then extracted with ether (2 times). The combined ether extracts were washed, dried and concentrated to give 1.9 g crude product. This material was recrystallized from ethanol followed by recrystallization from ethylacetate to give 0.7 g 3,4-dihydro-2-methyl-3-oxo-2H-naphtho[2,3-e]-1,2-thiazine-4-carboxanilide 1,1-dioxide.

Yield: 37%

Melting point: 188-190° C.

Structure was confirmed by elementary analysis ($C_{20}H_{16}N_2O_4S$: C,H,N,S) and IR- and NMR-spectroscopy.

Preparation of the Starting Material:

To a solution of 124 g (0.84 mol) 2-methyl-5,6,7,8-tetrahydro-naphthalene in 600 mL CHCl₃ 294 g (2.52 mol) chlorosulfonic acid at 0° C. were added. After 2 hrs at room temperature the solution was slowly poured onto ice. The organic phase was washed, dried and concentrated to give 231.4 g 2-methyl-5,6,7,8-tetrahydro-naphthalene-2-sulfonic acid chloride used directly for the subsequent reaction. To a solution of 57.5 g (1.8 mol) methylamine in 1.2 L ethanol were added at +5° C. 231.4 g (0.84 mol) of the above sulfonic acid chloride followed by 192 g (1.9 mol) triethylamine. The mixture was stirred at +5° C. for 2 hrs and allowed to come to room temperature over 2 hrs. The reaction mixture was concentrated and the residue taken up in ether, washed, dried, and concentrated. Recrystallization of the residue from cyclohexane gave 136.1 g 2-methyl-5,6,7,8-tetrahydro-naphthalene-3-sulfonic acid methylamide.

This compound was dehydrogenated by use of DDQ (2,3-dichloro-5,6-dicyano-benzoquinone) in 32% yield to 2-methyl-naphthalene-(N-methyl)3-sulfonamide (melting point 139-140° C.).

To a solution of 4.5 g (19 mmol) 2-methyl-naphthalene-3-(N-methyl)sulfonamide in 200 mL tetrahydrofurane at −20° C. was added 100 mL of a 1.5 molare (40 mmol) butyl lithium in hexane. The resulting mixture was allowed to come to room temperature and was poured onto a mixture of ether and solid $CO_2$. After addition of water the resulting mixture acidified with dilute HCl and the extracted with $CH_2Cl_2$. The $CH_2Cl_2$ solution was washed, dried and concentrated. Recrystallization from ethylene chloride gave 2.6 g 3-(N-methyl-sulfamoyl)-naphthalene-2-acetic acid (melting point: 185-186° C.).

This naphthalene-2-acetic acid (2.6 g, 9.4 mmol) was 12 hrs refluxed in 100 mL xylene with the addition of 0.2 g p-toluene-sulfonic acid. The reaction mixture was cooled, filtered, washed with water and concentrated. Recrystallization from ethanol gave 1.5 g (61%) 3,4-dihydro-2-methyl-3-oxo-2H-naphtho[2,3-e]-1,2-thiazine 1,1-dioxide (melting point: 126-127° C.).

EXAMPLE 19

3,4-Dihydro-2-methyl-3-oxo-2H-naphtho[2,3-e]-1,2-thiazine-4-(4-methyl) carboxanilide 1,1-dioxide

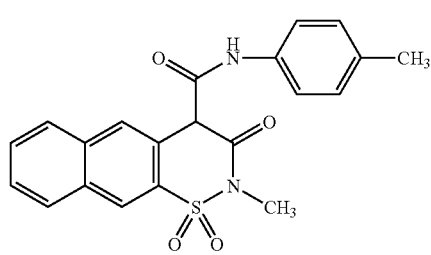

To a suspension of 0.276 g (11.5 mmol) sodium hydride in 20 mL tetrahydrofurane was added at −5° C. under $N_2$ a solution of 2 g (7.6 mmol) 3,4-dihydro-2-methyl-3-oxo-2H-naphtho[2,3-e]-1,2-thiazine 1,1-dioxide in 30 mL tetrahydrofurane. After termination of the hydrogen formation 2.56 g (19.2 mmol) p-methyl-phenylisocyanate dissolved in 50 mL tetrahydrofurane were added at −5° C. After stirring at room temperature the resulting mixture was quenched with ice/water and by addition of dilute HCl and then extracted with $CH_2Cl_2$ (2 times). The combined $CH_2Cl_2$ extracts were washed, dried and concentrated to give 6 g crude product. This material was recrystallized from ethanol to give 2.1 g 3,4-dihydro-2-methyl-3-oxo-2H-naphtho[2,3-e]-1,2-thiazine-4-(4-methyl)carboxanilide 1,1-dioxide.

Yield: 83%

Melting point: 223-225° C.

Structure was confirmed by elementary analysis ($C_{21}H_{18}N_2O_4S$: C,H,N,S) and IR- and NMR-spectroscopy.

EXAMPLE 20

3,4-Dihydro-2-methyl-3-oxo-2H-naphtho[2,3-e]-1,2-thiazine-4-(3-fluoro) carboxanilide 1,1-dioxide

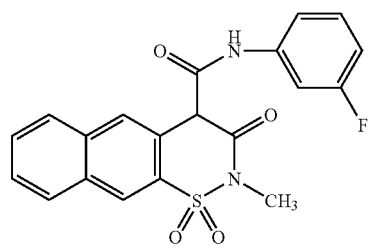

Prepared from 3,4-dihydro-2-methyl-3-oxo-2H-naphtho[2,3-e]-1,2-thiazine 1,1-dioxide and m-fluoro-phenylisocyanate analogous to example 19 and recrystallized from ethanol.

Yield: 46%

Melting point: 191-192° C.

Structure was confirmed by elementary analysis ($C_{20}H_{15}FN_2O_4S$: C,H,N,S) and UV-, IR- and NMR-spectroscopy.

EXAMPLE 21

3,4-Dihydro-2-methyl-3-oxo-2H-naphtho[2,3-e]-1,2-thiazine-4-(4-fluoro) carboxanilide 1,1-dioxide

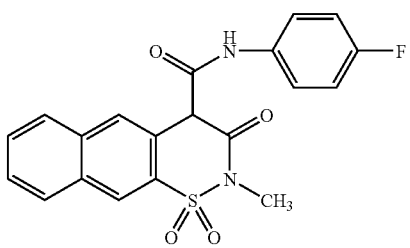

Prepared from 3,4-dihydro-2-methyl-3-oxo-2H-naphtho[2,3-e]-1,2-thiazine 1,1-dioxide and p-fluoro-phenylisocyanate analogous to example 19 and recrystallized from ethanol.

Yield: 52%

Melting point: 235-237° C.

Structure was confirmed by elementary analysis ($C_{20}H_{15}FN_2O_4S$: C,H,N,S) and UV-, IR- and NMR-spectroscopy.

EXAMPLE 22

3,4-Dihydro-2-methyl-3-oxo-2H-naphtho[2,3-e]-1,2-thiazine-4-(2-chloro) carboxanilide 1,1-dioxide

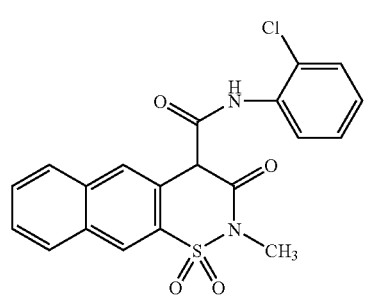

Prepared from 3,4-dihydro-2-methyl-3-oxo-2H-naphtho[2,3-e]-1,2-thiazine 1,1-dioxide and o-chloro-phenylisocyanate analogous to example 19 and recrystallization from ethylacetate Yield: 52%

Structure was confirmed by elementary analysis ($C_{20}H_{15}ClN_2O_4S$: C,H,N,S) and UV-, IR- and NMR-spectroscopy.

EXAMPLE 23

3,4-Dihydro-2-methyl-3-oxo-2H-naphtho[2,3-e]-1,2-thiazine-4-(2,5-dichloro) carboxanilide 1,1-dioxide

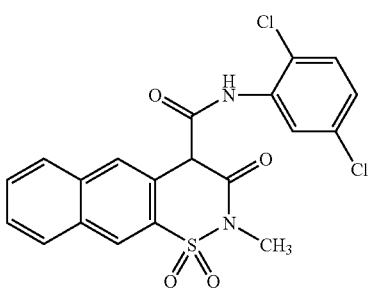

Prepared from 3,4,6,7,8,9-hexahydro-2-methyl-3-oxo-2H-naphtho[2,3-e]-1,2-thiazine 1,1-dioxide and 2,5-dichloro-phenylisocyanate analogous to example 19 and recrystallization from ethanol.

Yield: 63%

Structure was confirmed by elementary analysis ($C_{20}H_{18}Cl_2N_2O_4S$: C,H,N,S) and UV-, IR- and NMR-spectroscopy.

EXAMPLE 24

3,4-Dihydro-2-methyl-3-oxo-2H-naphtho[2,3-e]-1,2-thiazine-4-(3-chloro-4-methyl) carboxanilide 1,1-dioxide

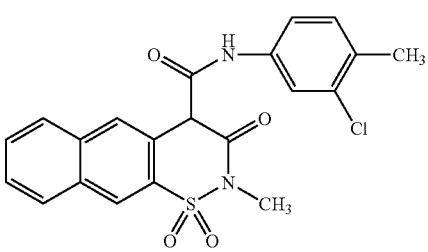

Prepared from 3,4-dihydro-2-methyl-3-oxo-2H-naphtho[2,3-e]-1,2-thiazine 1,1-dioxide and 3-methyl-4-chloro-phenylisocyanate analogous to example 19 and recrystallization from ethylacetate.

Yield: 65%

Structure was confirmed by elementary analysis ($C_{21}H_{17}ClN_2O_4S$: C,H,N,S) and UV-, IR- and NMR-spectroscopy.

EXAMPLE 25

3,4-Dihydro-2-methyl-3-oxo-2H-naphtho[2,3-e]-1,2-thiazine-4-(4-bromo)carboxanilide 1,1-dioxide

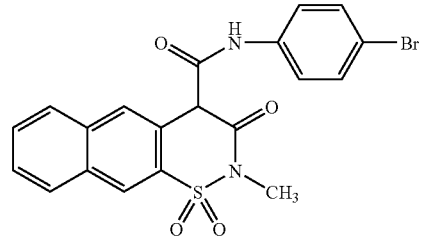

Prepared from 3,4-dihydro-2-methyl-3-oxo-2H-naphtho[2,3-e]-1,2-thiazine 1,1-dioxide and 4-bromo-phenylisocyanate analogous to example 19 and recrystallization from ethanol.

Yield: 76%

Structure was confirmed by elementary analysis ($C_{20}H_{15}BrN_2O_4S$: C,H,N,S) and UV-, IR- and NMR-spectroscopy.

EXAMPLE 26

3,4-Dihydro-2-methyl-3-oxo-2H-naphtho[2,3-e]-1,2-thiazine-4-(3-trifluoromethyl) carboxanilide 1,1-dioxide

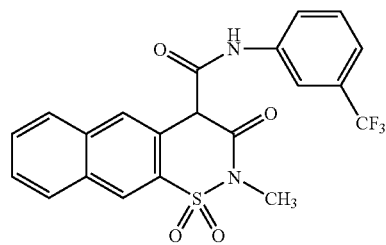

Prepared from 3,4-dihydro-2-methyl-3-oxo-2H-naphtho[2,3-e]-1,2-thiazine 1,1-dioxide and 3-trifluoro-phenylisocyanate analogous to example 19 and recrystallization from cyclohexane/ethylacetate.
Yield: 41%
Melting point: 148-150° C.
Structure was confirmed by elementary analysis ($C_{21}H_{15}F_3N_2O_4S$: C,H,N,S) and UV- and IR-spectroscopy.

EXAMPLE 27

3,4-Dihydro-2-methyl-3-oxo-2H-naphtho[2,3-e]-1,2-thiazine-4-(4-nitro)carboxanilide 1,1-dioxide

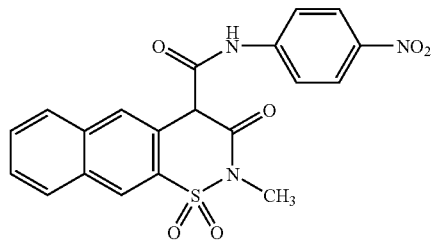

Prepared from 3,4-dihydro-2-methyl-3-oxo-2H-naphtho[2,3-e]-1,2-thiazine 1,1-dioxide and 4-nitro-phenylisocyanate analogous to example 19 and recrystallization from ethanol.
Yield: 49%
Structure was confirmed by elementary analysis ($C_{20}H_{15}N_3O_6S$: C,H,N,S).

EXAMPLE 28

3,4-Dihydro-2-ethyl-3-oxo-2H-naphtho[2,3-e]-1,2-thiazine-4-(4-chloro)carboxanilide 1,1-dioxide

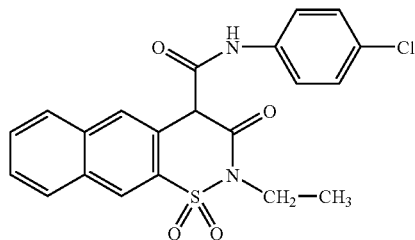

Prepared from 3,4-dihydro-2-ethyl-3-oxo-2H-naphtho[2,3-e]-1,2-thiazine 1,1-dioxide and 4-chloro-phenylisocyanate analogous to example 19 and recrystallization from ethanol.
Yield: 57%
Melting point: 206-208° C.
Structure was confirmed by elementary analysis ($C_{21}H_{17}ClN_2O_4S$: C,H,N,S) and UV-, IR- and NMR-spectroscopy.

Preparation of the Starting Material:
A solution of 7 g (31.6 mmol) 3-methyl-naphthalene-2-sulphonamide 1.27 g (31.6 mmol) sodium hydroxide and 9.83 g (63 mmol) ethyliodine in 500 ml ethanol was stirred for 72 hrs. The solvent was removed using an evaporator and the resulting residue was filtered on a silica gel column using methylenchloride and ethanol as solvent. Recrystallization from cyclohexane/ethylacetate resulted in 3.5 g (45%) 3-methyl-naphthalene-2-(N-ethyl)sulphonamide (melting point: 208-209° C.). 3.5 g (12 mmol) 2-methyl-naphthalene-3-(N-ethyl)sulfonamide were transformed into 3-(N-ethyl-sulfamoyl)-naphthalene-2-acetic acid (melting point: 168-170° C.) as described in example 1.

This naphthalene-2-acetic acid (1.4 g, 4 mmol) was 12 hrs refluxed in 250 mL xylene with the addition of 0.2 g p-toluene-sulfonic acid. The reaction mixture was cooled, filtered, washed with water and concentrated. Recrystallization from cyclohexane/ethylacetate to give 1.1 g (83%) 3,4-dihydro-2-ethyl-3-oxo-2H-naphtho[2,3-e]-1,2-thiazine 1,1-dioxide, melting point 170-171° C.

EXAMPLE 29

3,4-Dihydro-2,6-dimethyl-3-oxo-2H-thieno[2,3-e]-1,2-thiazine-4-carboxanilide 1,1-dioxide

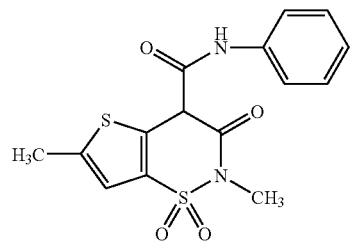

To a suspension of 0.78 g (32.5 mmol) sodium hydride in 50 mL tetrahydrofurane was added at −5° C. under $N_2$ a solution of 5 g (21.6 mmol) 3,4-dihydro-2,6-dimethyl-3-oxo-2H-thieno[2,3-e]-1,2-thiazine 1,1-dioxide in 50 mL tetrahydrofurane. After termination of the hydrogen formation 6.5 g (55 mmol) phenylisocyanate dissolved in 50 mL tetrahydrofurane were added at −5° C. After stirring at room temperature the resulting mixture was quenched with ice/water and by addition of dilute HCl and then extracted with $CH_2Cl_2$ (2 times). The combined $CH_2Cl_2$ extracts were washed, dried and concentrated to give 6 g crude product. This material was recrystallized from ethanol to give 5.2 g 3,4-dihydro-2,6-dimethyl-3-oxo-2H-thieno[2,3-e]-1,2-thiazine-4-carboxanilide 1,1-dioxide.
Yield: 69%
Melting point: 182-184° C.
Structure was confirmed by elementary analysis ($C_{15}H_{14}N_2O_4S_2$: C,H,N,S) and IR- and NMR-spectroscopy.

Preparation of the Starting Material:
2,5-dimethylthiophene was transformed to 2,5-dimethyl-thiophene-3-(N-methyl)sulfonamide (melting point: 70-71° C.) analogous to example 19. Subsequent reaction with butyllithium and carbon dioxide yielded 5-methyl-3-(N-methyl)aminosulfonyl-thiophene 2-acetic acid (melting point: 109° C.) and cyclization with p-toluene sulfonic acid 3,4-dihydro-2,6-dimethyl-3-oxo-2H-thieno[2,3-e]-1,2-thiazine 1,1-dioxide.
Melting point: 119-120° C.
Structure was confirmed by elementary analysis ($C_8H_9NO_3S_2$: C,H,N,S) and IR- and NMR-spectroscopy.

EXAMPLE 30

3,4-Dihydro-2,6-dimethyl-3-oxo-2H-thieno[2,3-e]-1.2-thiazine-4-(4-methyl) carboxanilide 1,1-dioxide

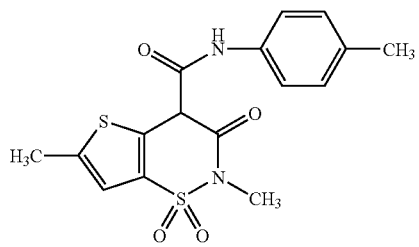

Prepared from 3,4-dihydro-2,6-dimethyl-3-oxo-2H-thieno[2,3-e]-1,2-thiazine 1,1-dioxide and 4-methyl-phenylisocyanate analogous to example 29 and recrystallization from ethanol.

Yield: 58%

Melting point: 200-201° C.

Structure was confirmed by elementary analysis ($C_{16}H_{16}N_2O_4S_2$: C,H,N,S) and IR- and NMR-spectroscopy.

EXAMPLE 31

3,4-Dihydro-2,6-dimethyl-3-oxo-2H-thieno[2,3-e]-1.2-thiazine-4-(4-fluoro) carboxanilide 1,1-dioxide

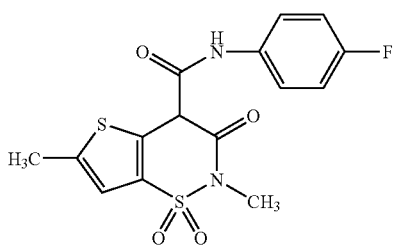

Prepared from 3,4-dihydro-2,6-dimethyl-3-oxo-2H-thieno[2,3-e]-1,2-thiazine 1,1-dioxide and 4-fluoro-phenylisocyanate analogous to example 29 and recrystallization from ethanol.

Yield: 56%

Melting point: 191-193° C.

Structure was confirmed by elementary analysis ($C_{15}H_{13}FN_2O_4S_2$: C,H,N,S) and IR- and NMR-spectroscopy.

EXAMPLE 32

3,4-Dihydro-2,6-dimethyl-3-oxo-2H-thieno[2,3-e]-1.2-thiazine-4-(2,4-difluoro) carboxanilide 1,1-dioxide

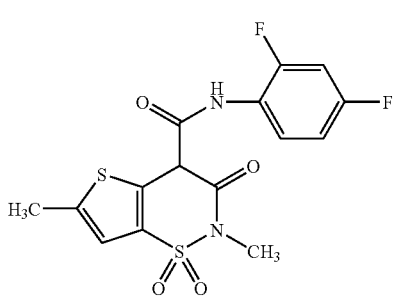

Prepared from 3,4-dihydro-2,6-dimethyl-3-oxo-2H-thieno[2,3-e]-1,2-thiazine 1,1-dioxide and 2,4-difluoro-phenylisocyanate analogous to example 29 and recrystallization from benzene/petroleum ether.

Yield: 72%

Melting point: 144-145° C.

Structure was confirmed by elementary analysis ($C_{15}H_{13}F_2N_2O_4S_2$: C,H,N,S) and IR- and NMR-spectroscopy.

EXAMPLE 33

3,4-Dihydro-2,6-dimethyl-3-oxo-2H-thieno[2,3-e]-1.2-thiazine-4-(3,4-dichloro) carboxanilide 1,1-dioxide

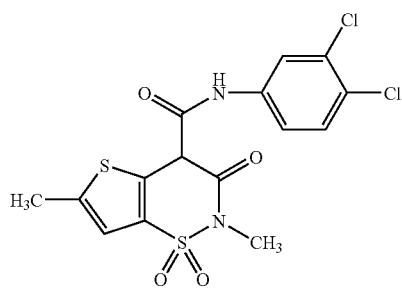

Prepared from 3,4-dihydro-2,6-dimethyl-3-oxo-2H-thieno[2,3-e]-1,2-thiazine 1,1-dioxide and 2,4-dichloro-phenylisocyanate analogous to example 29 and recrystallization from ethanol.

Yield: 19%

Melting point: 179-180° C.

Structure was confirmed by elementary analysis ($C_{15}H_{13}Cl_2N_2O_4S_2$: C,H,N,S).

EXAMPLE 34

3,4-Dihydro-2,6-dimethyl-3-oxo-2H-thieno[2,3-e]-1.2-thiazine-4-(3-chloro-4-methyl) carboxanilide 1,1-dioxide

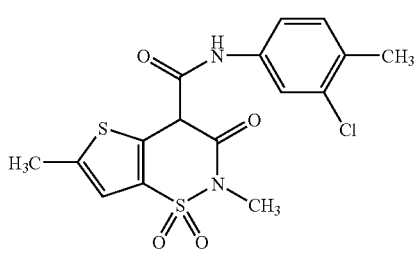

Prepared from 3,4-dihydro-2,6-dimethyl-3-oxo-2H-thieno[2,3-e]-1,2-thiazine 1,1-dioxide and 3-chloro-4-methylphenylisocyanate analogous to example 29 and recrystallization from isopropanol.

Yield: 42%

Melting point: 186-188° C.

Structure was confirmed by elementary analysis ($C_{16}H_{15}ClN_2O_4S_2$: C,H,N,S) and IR- and NMR-spectroscopy.

EXAMPLE 35

3,4-Dihydro-2,6-dimethyl-3-oxo-2H-thieno[2,3-e]-1.2-thiazine-4-(4-bromo) carboxanilide 1,1-dioxide

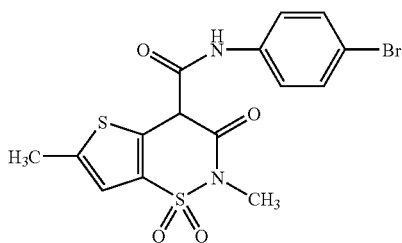

Prepared from 3,4-dihydro-2,6-dimethyl-3-oxo-2H-thieno[2,3-e]-1,2-thiazine 1,1-dioxide and 4-bromophenylisocyanate analogous to example 29 and recrystallization from benzene/petroleum ether.

Yield: 22%

Melting point: 138-140° C.

Structure was confirmed by elementary analysis ($C_{15}H_{13}BrN_2O_4S_2$: C,H,N,S) and IR- and NMR-spectroscopy.

EXAMPLE 36

3,4-Dihydro-2,6-dimethyl-3-oxo-2H-thieno[2,3-e]-1.2-thiazine-4-(3-trifluoromethyl) carboxanilide 1,1-dioxide

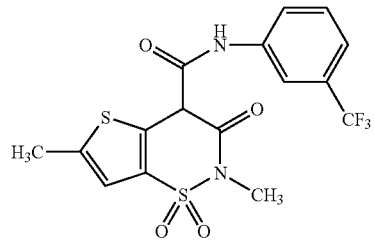

Prepared from 3,4-dihydro-2,6-dimethyl-3-oxo-2H-thieno[2,3-e]-1,2-thiazine 1,1-dioxide and 3-trifluoromethylphenylisocyanate analogous to example 29 and recrystallization from benzene/petroleum ether.

Yield: 50%

Melting point: 103-104° C.

Structure was confirmed by elementary analysis ($C_{16}H_{13}F_3N_2O_4S_2$: C,H,N,S) and IR- and NMR-spectroscopy.

EXAMPLE 37

3,4-Dihydro-2,6-dimethyl-3-oxo-2H-thieno[2,3-e]-1.2-thiazine-4-(4-trifluoromethyl) carboxanilide 1,1-dioxide

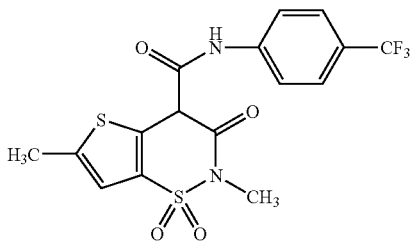

Prepared from 3,4-dihydro-2,6-dimethyl-3-oxo-2H-thieno[2,3-e]-1,2-thiazine 1,1-dioxide and 4-trifluoromethylphenylisocyanate analogous to example 29 and recrystallization from cyclohexane/chloroform.

Yield: 50%

Melting point: 103-104° C.

Structure was confirmed by elementary analysis ($C_{16}H_{13}F_3N_2O_4S_2$: C,H,N,S) and IR- and NMR-spectroscopy.

EXAMPLE 38

3,4-Dihydro-2,6-dimethyl-3-oxo-2H-thieno[2,3-e]-1.2-thiazine-4-(4-methoxy) carboxanilide 1,1-dioxide

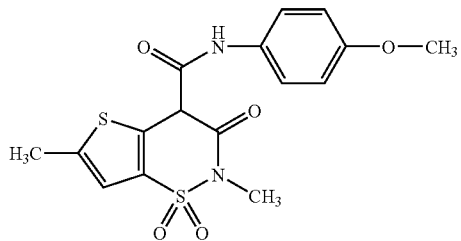

Prepared from 3,4-dihydro-2,6-dimethyl-3-oxo-2H-thieno[2,3-e]-1,2-thiazine 1,1-dioxide and 4-methoxyphenylisocyanate analogous to example 29 and recrystallization from ethanol.

Yield: 61%

Melting point: 176-178° C.

Structure was confirmed by elementary analysis ($C_{16}H_{16}N_2O_5S_2$: C,H,N,S) and IR- and NMR-spectroscopy.

EXAMPLE 39

3,4-Dihydro-2,6-dimethyl-3-oxo-2H-thieno[2,3-e]-1.2-thiazine-4-(4-nitro) carboxanilide 1,1-dioxide

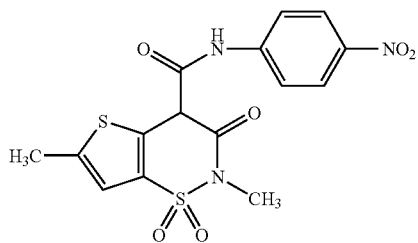

Prepared from 3,4-dihydro-2,6-dimethyl-3-oxo-2H-thieno[2,3-e]-1,2-thiazine 1,1-dioxide and 4-nitrophenylisocyanate analogous to example 29.
Yield: 52%

EXAMPLE 40

3,4-Dihydro-2,6-dimethyl-3-oxo-2H-thieno[2,3-e]-1.2-thiazine-4-(4-nitro) carboxanilide 1,1-dioxide Cyclohexylamine Salt Prepared from 3,4-dihydro-2,6-dimethyl-3-oxo-2H-thieno[2,3-e]-1,2-thiazine-4-(4-nitro)carboxanilide 1,1-dioxide and cyclohexylamine and recrystallization from water/ethanol.
Yield: 95%
Melting point: 208-209° C.
Structure was confirmed by elementary analysis ($C_{21}H_{26}N_4O_6S_2$: C,H,N,S) and IR- and NMR-spectroscopy.

EXAMPLE 41

3,4-Dihydro-2,6-dimethyl-3-oxo-2H-furo[2,3-e]-1.2-thiazine-4-(4-methyl) carboxanilide 1,1-dioxide

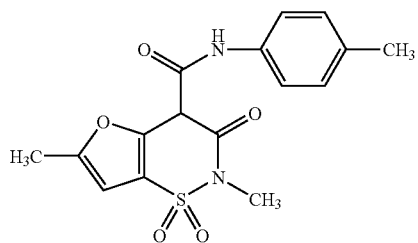

To a suspension of 0.54 g (22 mmol) sodium hydride in 50 mL tetrahydrofurane was added at −5° C. under $N_2$ a solution of 4 g (18.6 mmol) 3,4-dihydro-2,6-dimethyl-3-oxo-2H-furo[2,3-e]-1,2-thiazine 1,1-dioxide in 50 mL tetrahydrofurane. After termination of the hydrogen formation 6.5 g (55 mmol) 4-methylphenylisocyanate dissolved in 50 mL tetrahydrofurane were added at −5° C. After stirring at room temperature the resulting mixture was quenched with ice/water and by addition of dilute HCl and then extracted with $CH_2Cl_2$ (2 times). The combined $CH_2Cl_2$ extracts were washed, dried and concentrated to give 5.7 g crude product. This material was recrystallized from benzene to give 4 g 3,4-dihydro-2,6-dimethyl-3-oxo-2H-furo[2,3-e]-1,2-thiazine-4-(4-methyl)carboxanilide 1,1-dioxide.
Yield: 62%
Melting point: 210-212° C.
Structure was confirmed by elementary analysis ($C_{16}H_{16}N_2O_5S$: C,H,N,S) and IR- and NMR-spectroscopy.

Preparation of the Starting Material:
2,5-dimethylfurane was transformed to 2,5-dimethylfurane-3-(N-methyl)sulfonamide analogous to example 19. Subsequent reaction with n-butyllithium and carbon dioxide yielded 5-methyl-3-(N-methyl)aminosulfonyl-furane 2-acetic acid (melting point: 112-113° C.) and cyclization with phosphorous pentachloride 3,4-dihydro-2,6-dimethyl-3-oxo-2H-furo[2,3-e]-1,2-thiazine 1,1-dioxide.
Melting point: 132-133° C.
Structure was confirmed by elementary analysis ($C_8H_9NO_3S$: C,H,N,S) and IR- and NMR-spectroscopy.

EXAMPLE 42

3,4-Dihydro-2,6-dimethyl-3-oxo-2H-furo[2,3-e]-1.2-thiazine-4-(4-bromo) carboxanilide 1,1-dioxide

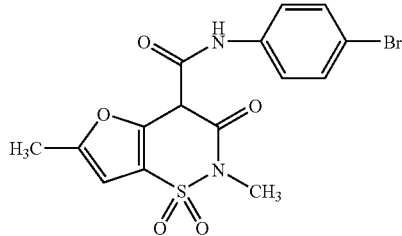

Prepared from 3,4-dihydro-2,6-dimethyl-3-oxo-2H-furo[2,3-e]-1,2-thiazine 1,1-dioxide and 4-bromophenylisocyanate analogous to example 41 and recrystallization from cyclohexane.
Yield: 72%
Melting point: 180-181° C.
Structure was confirmed by elementary analysis ($C_{15}H_{13}BrN_2O_5S$: C,H,N,S) and IR- and NMR-spectroscopy.

EXAMPLE 43

3,4-Dihydro-2,6-dimethyl-3-oxo-2H-thieno[3,2-e]-1.2-thiazine-4-carboxanilide 1,1-dioxide

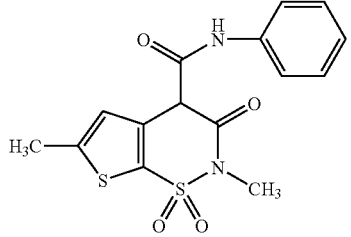

To a suspension of 0.82 g (34 mmol) sodium hydride in 50 mL tetrahydrofurane was added at −5° C. under $N_2$ a solution of 5.3 g (23 mmol) 3,4-dihydro-2,6-dimethyl-3-oxo-2H-thieno[3,2-e]-1,2-thiazine 1,1-dioxide in 50 mL tetrahydrofurane. After termination of the hydrogen formation 6.5 g (55 mmol) phenylisocyanate dissolved in 50 mL tetrahydrofurane were added at −5° C. After stirring at room temperature the resulting mixture was quenched with ice/water and by addition of dilute HCl and then extracted with $CH_2Cl_2$ (2 times). The combined $CH_2Cl_2$ extracts were washed, dried and concentrated to give 6 g crude product. This material was recrystallized from ethanol to give 4.8 g 3,4-dihydro-2,6-dimethyl-3-oxo-2H-thieno[3,2-e]-1,2-thiazine-4-carboxanilide 1,1-dioxide.

Yield: 60%

Melting point: 184-185° C.

Structure was confirmed by elementary analysis ($C_{15}H_{14}N_2O_4S_2$: C,H,N,S) and IR- and NMR-spectroscopy.

Preparation of the Starting Material:

2,4-dimethylthiophene was transformed to 3,5-dimethyl-thiophene-2-(N-methyl)sulfonamide analogous to example 19. Subsequent reaction with butyllithium and carbon dioxide yielded 5-methyl-2-(N-methyl)aminosulfonyl-thiophene 3-acetic acid (melting point: 138° C.) and cyclization with p-toluene sulfonic acid 3,4-dihydro-2,6-dimethyl-3-oxo-2H-thieno[3,2-e]-1,2-thiazine 1,1-dioxide.

Melting point: 83-84° C.

Structure was confirmed by elementary analysis ($C_8H_9NO_3S_2$: C,H,N,S) and IR- and NMR-spectroscopy.

EXAMPLE 44

3,4-Dihydro-2,6-dimethyl-3-oxo-2H-thieno[3,2-e]-1.2-thiazine-4-(4-methyl) carboxanilide 1,1-dioxide

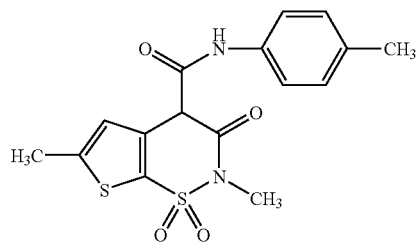

Prepared from 3,4-dihydro-2,6-dimethyl-3-oxo-2H-thieno[3,2-e]-1,2-thiazine 1,1-dioxide and 4-methyl-phenyl-isocyanate analogous to example 43 and recrystallization from ethanol.

Yield: 60%

Melting point: 185° C.

Structure was confirmed by elementary analysis ($C_{16}H_{16}N_2O_4S_2$: C,H,N,S) and IR- and NMR-spectroscopy.

EXAMPLE 45

3,4-Dihydro-2,6-dimethyl-3-oxo-2H-thieno[3,2-e]-1.2-thiazine-4-(2-fluoro) carboxanilide 1,1-dioxide

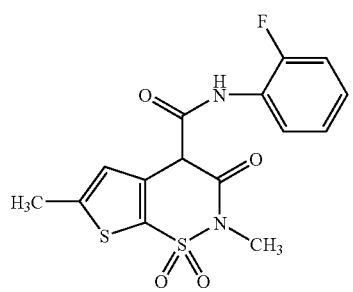

Prepared from 3,4-dihydro-2,6-dimethyl-3-oxo-2H-thieno[3,2-e]-1,2-thiazine 1,1-dioxide and 2-fluoro-phenyl-isocyanate analogous to example 43 and recrystallization from ethanol.

Yield: 95%

Melting point: 159-160° C.

Structure was confirmed by elementary analysis ($C_{15}H_{13}FN_2O_4S_2$: C,H,N,S) and IR- and NMR-spectroscopy.

EXAMPLE 46

3,4-Dihydro-2,6-dimethyl-3-oxo-2H-thieno[3,2-e]-1.2-thiazine-4-(4-fluoro) carboxanilide 1,1-dioxide

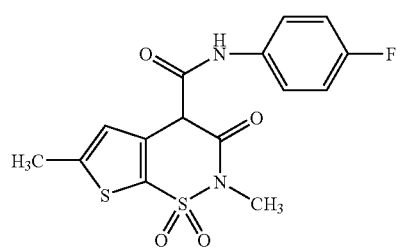

Prepared from 3,4-dihydro-2,6-dimethyl-3-oxo-2H-thieno[3,2-e]-1,2-thiazine 1,1-dioxide and 4-fluoro-phenyl-isocyanate analogous to example 43 and recrystallization from ethanol.

Yield: 96%

Melting point: 173-174° C.

Structure was confirmed by elementary analysis ($C_{15}H_{13}FN_2O_4S_2$: C,H,N,S) and IR- and NMR-spectroscopy.

EXAMPLE 47

3,4-Dihydro-2,6-dimethyl-3-oxo-2H-thieno[3,2-e]-1.2-thiazine-4-(4-bromo) carboxanilide 1,1-dioxide

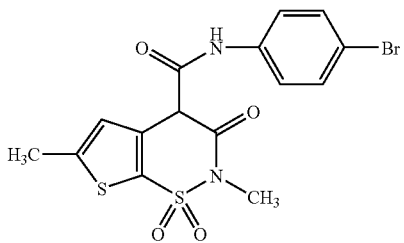

Prepared from 3,4-dihydro-2,6-dimethyl-3-oxo-2H-thieno[3,2-e]-1,2-thiazine 1,1-dioxide and 4-bromo-phenyl-isocyanate analogous to example 43 and recrystallization from ethyl acetate.

Yield: 77%

Melting point: 180-182° C.

Structure was confirmed by elementary analysis ($C_{15}H_{13}BrN_2O_4S_2$: C,H,N,S) and IR- and NMR-spectroscopy.

EXAMPLE 48

3,4-Dihydro-2,6-dimethyl-3-oxo-2H-thieno[3,2-e]-1.2-thiazine-4-(3-trifluoromethyl) carboxanilide 1,1-dioxide

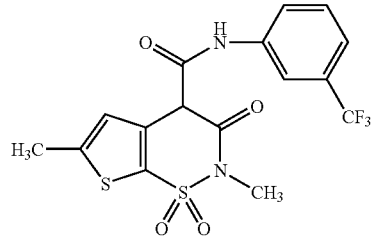

Prepared from 3,4-dihydro-2,6-dimethyl-3-oxo-2H-thieno[3,2-e]-1,2-thiazine 1,1-dioxide and 3-trifluoromethyl-phenylisocyanate analogous to example 43 and recrystallization from isopropanol.

Yield: 65%

Melting point: 163-164° C.

Structure was confirmed by elementary analysis ($C_{16}H_{13}F_3N_2O_4S_2$: C,H,N,S) and IR- and NMR-spectroscopy.

EXAMPLE 49

3,4-Dihydro-2,6-dimethyl-3-oxo-2H-thieno[3,2-e]-1.2-thiazine-4-(4-trifluoromethyl) carboxanilide 1,1-dioxide

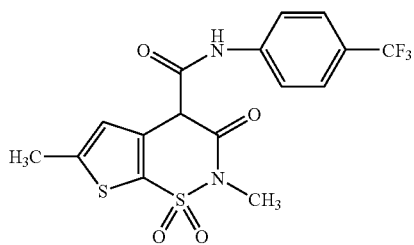

Prepared from 3,4-dihydro-2,6-dimethyl-3-oxo-2H-thieno[3,2-e]-1,2-thiazine 1,1-dioxide and 4-trifluoromethyl-phenylisocyanate analogous to example 43 and recrystallization from ethanol.

Yield: 69%

Melting point: 190° C.

Structure was confirmed by elementary analysis ($C_{16}H_{13}F_3N_2O_4S_2$: C,H,N,S) and IR- and NMR-spectroscopy.

EXAMPLE 50

3,4-Dihydro-2,6-dimethyl-3-oxo-2H-thieno[2,3-e]-1.2-thiazine-4-(2-fluoro) carboxanilide 1,1-dioxide

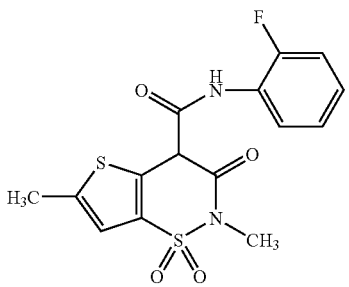

Prepared from 3,4-dihydro-2,6-dimethyl-3-oxo-2H-thieno[2,3-e]-1,2-thiazine 1,1-dioxide and 2-fluorophenyl-isocyanate analogous to example 29 and recrystallization from ethanol.

Yield: 64%

Melting point: 169-170° C.

Structure was confirmed by elementary analysis ($C_{15}H_{13}FN_2O_4S_2$: C,H,N,S) and IR- and NMR-spectroscopy.

Examples of Pharmaceutical Formulations

| A) | Tablets | per tablet |
|---|---|---|
| | active substance | 50 mg |
| | lactose | 170 mg |
| | corn starch | 260 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance | 407 mg |
| | corn starch | 210 mg |
| | lactose | 65 mg |
| | microcrystalline cellulose | 40 mg |
| | polyvinylpyrrolidone | 20 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) | Coated tablets | per coated tablet |
|---|---|---|
| | Active substance | 5 mg |
| | Corn starch | 41.5 mg |
| | Lactose | 30 mg |
| | Polyvinylpyrrolidone | 3 mg |
| | Magnesium stearate | 0.5 mg |
| | | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) | Capsules | per capsule |
|---|---|---|
| | Active substance | 25 mg |
| | Corn starch | 283.5 mg |
| | Magnesium stearate | 1.5 mg |
| | | 310 mg |

The substance and corn starch are mixed and moistened with water. The moist mass is screened and dried. The dry granules are screened and mixed with magnesium stearate. The finished mixture is packed into size 1 hard gelatine capsules.

| E) | Ampoule solution | |
|---|---|---|
| | active substance | 0.5 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 0.5 mg, 2.5 mg and 5.0 mg of active substance.

| F) | Suppositories | |
|---|---|---|
| | Active substance | 30 mg |
| | Solid fat | 1670 mg |
| | | 1700 mg |

The solid fat is melted. The ground active substance is homogenously dispersed at 40° C. It is cooled to 38° C. and poured into slightly chilled suppository moulds.

The invention claimed is:

1. A compound selected from the formulas IIa, IIb

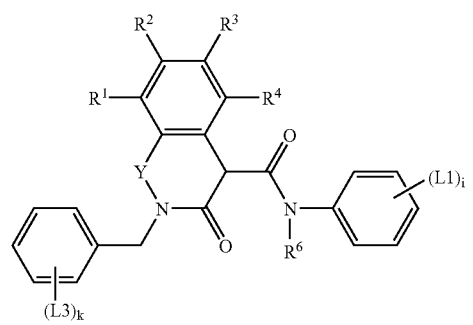

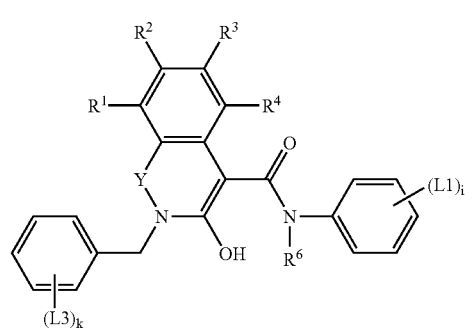

wherein

Y is —($SO_2$)-;

R1, R4 are each independently selected from the group consisting of H, F, Cl, Br, CN, CF3, C1-4-alkyl and C1-4-alkoxy; and R2, R3 are each independently selected from the group consisting of H, F, Cl, Br, CN, CF3, C1-4-alkyl and C1-4-alkoxy;

R6 is H or C1-4-alkyl;

L1 is independently selected from the group consisting of C1-4-alkyl, C1-3-alkoxy, F, Cl, Br, CN, NO2 and CF3;

L3 of formula IIa is selected from the group consisting of C1-4-alkyl, F, Cl, Br, CN and CF3;

L3 of formula IIb is selected from the group consisting of C2-4-alkyl, F, Cl, Br, CN and CF3; and i is 0, 1, 2, 3, 4 or 5;

k is 1, 2, 3, 4 or 5;

or a pharmaceutically acceptable salt thereof.

2. A compound according to claim 1 wherein the compound is selected from the formula II.1a and II.1b

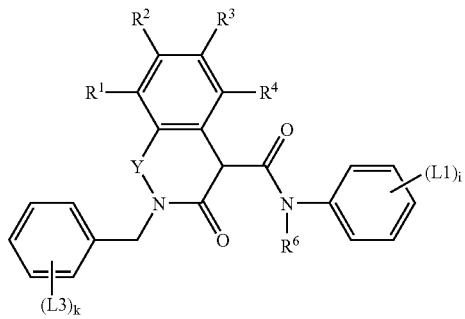
II.1a

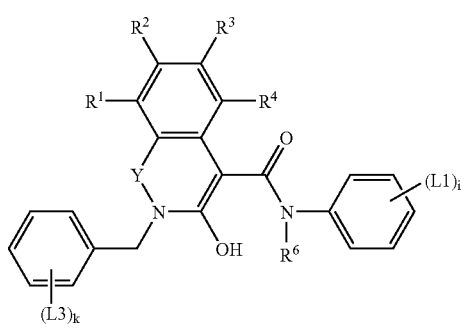
II.1b wherein the group Y, the substitutes R1, R4, R6, L1 and L3 and the index i and k are defined as in claim 1, and R2, R3 are each independently selected from the group consisting of H, F, Cl, Br, CN, CF3, C1-4-alkyl and C1-4-alkoxy; or or a pharmaceutically acceptable salt thereof.

3. A compound according to claim 1, selected from the group consisting of

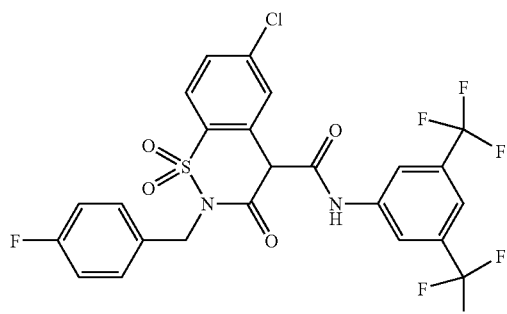
(15)

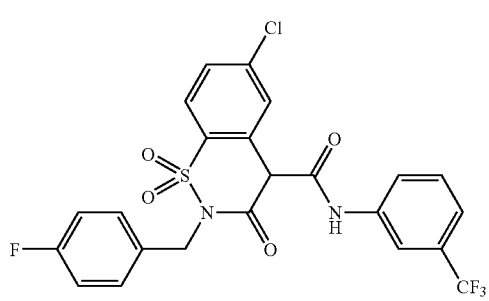
(36)

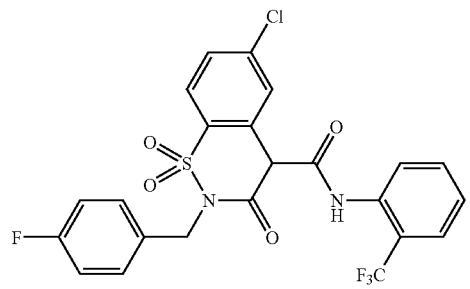
(37)

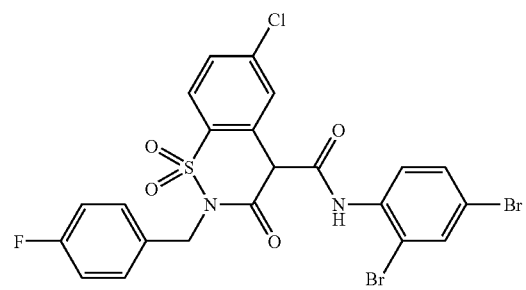
(38)

or a pharmaceutically acceptable salt thereof.

4. A compound selected from the formulas IIa, IIb

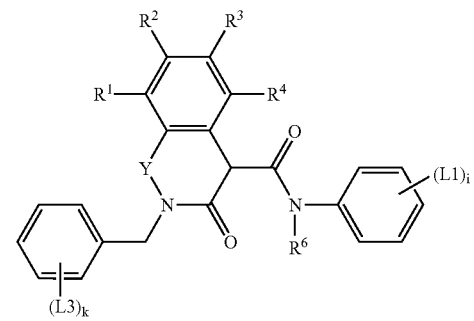
IIa

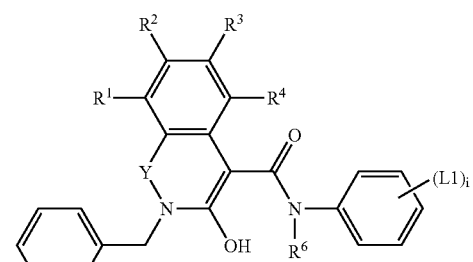
IIb wherein
- ---- represents a single or a double bond, such that the ring containing the groups V and W is a phenyl ring;
- V is defined as —CR1=;
- W is defined as =CR4-;
- Y is —(SO2)-;
- R1, R4 are each independently selected from the group consisting of H, F, Cl, Br, CN, CF3, C1-4-alkyl and C1-4-alkoxy; and R2, R3 are each independently selected from the group consisting of H, F, Cl, Br, CN, CF3, C1-4-alkyl and C1-4-alkoxy;
R6 is H or C1-4-alkyl;
L1 is independently selected from the group consisting of C1-4-alkyl, C1-3-alkoxy, F, Cl, Br, CN, NO2 and CF3;
L3 is each independently selected from the group consisting of C1-4-alkyl, F, Cl, Br, CN and CF3;
i is 0, 1, 2, 3, 4 or 5;
k is 1, 2, 3, 4 or 5;
wherein the compound is selected from the group consisting of

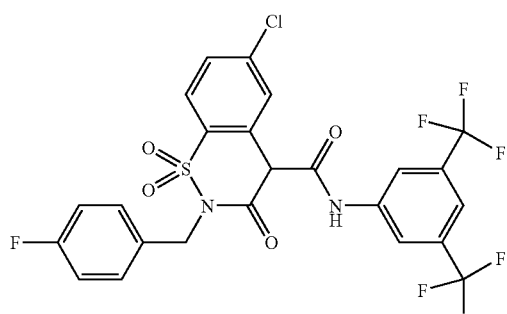

(15)

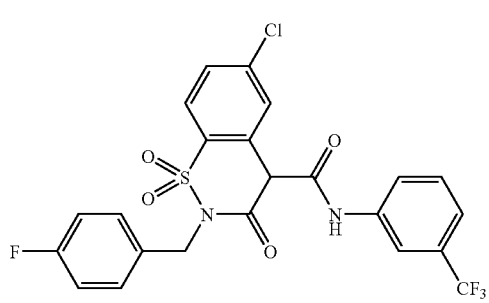

(36)

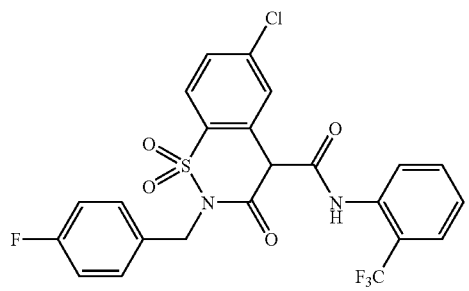

(37)

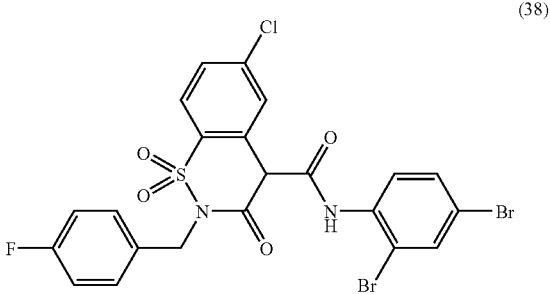

(38)

or a pharmaceutically acceptable salt thereof.

* * * * *

UNITED STATES PATENT AND TRADEMARK OFFICE
CERTIFICATE OF CORRECTION

PATENT NO. : 7,375,220 B2 Page 1 of 1
APPLICATION NO. : 11/132815
DATED : May 20, 2008
INVENTOR(S) : Klaus Bornemann et al.

It is certified that error appears in the above-identified patent and that said Letters Patent is hereby corrected as shown below:

Column 86, line 59, cancel the text beginning with "----represents a single" to and ending "defined as =CR4-;" in column 86, line 62.

Column 87, line 7, cancel text "each independently".

Signed and Sealed this

Seventeenth Day of February, 2009

JOHN DOLL
*Acting Director of the United States Patent and Trademark Office*